United States Patent
McKeown et al.

(10) Patent No.: US 10,240,210 B2
(45) Date of Patent: *Mar. 26, 2019

(54) METHODS OF STRATIFYING PATIENTS FOR TREATMENT WITH RETINOIC ACID RECEPTOR-ALPHA AGONISTS

(71) Applicant: Syros Pharmaceuticals, Inc., Cambridge, MA (US)

(72) Inventors: Michael Robert McKeown, Boston, MA (US); Christopher Fiore, Cambridge, MA (US); Matthew Lucas Eaton, Cambridge, MA (US); Emily Payton Lee, Cambridge, MA (US); Christian Fritz, Cambridge, MA (US)

(73) Assignee: Syros Pharmaceuticals, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/828,719

(22) Filed: Dec. 1, 2017

(65) Prior Publication Data

US 2018/0155796 A1 Jun. 7, 2018

Related U.S. Application Data

(63) Continuation of application No. 15/582,311, filed on Apr. 28, 2017, now Pat. No. 9,868,994, which is a continuation of application No. PCT/US2017/026657, filed on Apr. 7, 2017.

(60) Provisional application No. 62/320,352, filed on Apr. 8, 2016.

(51) Int. Cl.
*A61K 31/192* (2006.01)
*C12Q 1/6886* (2018.01)
*A61K 45/06* (2006.01)

(52) U.S. Cl.
CPC .......... *C12Q 1/6886* (2013.01); *A61K 31/192* (2013.01); *A61K 45/06* (2013.01); *C12Q 2600/106* (2013.01); *C12Q 2600/158* (2013.01)

(58) Field of Classification Search
CPC .................................................. A61K 31/192
See application file for complete search history.

(56) References Cited

U.S. PATENT DOCUMENTS

| | | |
|---|---|---|
| 8,030,031 B2 | 10/2011 | Kopreski |
| 8,669,058 B2 | 3/2014 | Liew |
| 9,868,994 B2 | 1/2018 | McKeown et al. |
| 2010/0099084 A1 | 4/2010 | Albitar |
| 2014/0051760 A1 | 2/2014 | Miller et al. |
| 2014/0272956 A1 | 9/2014 | Huang et al. |
| 2016/0355888 A1 | 12/2016 | Chen et al. |
| 2017/0292165 A1 | 10/2017 | McKeown et al. |

FOREIGN PATENT DOCUMENTS

| | | |
|---|---|---|
| WO | WO-03/025171 A2 | 3/2003 |
| WO | WO-2013/185105 A1 | 12/2013 |
| WO | WO-2015/085172 A2 | 6/2015 |
| WO | WO-2015/101618 A1 | 7/2015 |
| WO | WO-2016/144976 A1 | 9/2016 |
| WO | WO-2016/161107 A1 | 10/2016 |
| WO | WO-2017/091762 A1 | 6/2017 |
| WO | WO-2017/177167 A1 | 10/2017 |

OTHER PUBLICATIONS

Alsafadi, S. et al., Retinoic acid receptor alpha amplifications and retinoic acid sensitivity in breast cancers, Clin Breast Cancer, 13(5):401-408 (2013).
Asleson, A. et al., Amplication of the RARA gene in acute myeloid leukemia: significant finding or coincidental observation?, Cancer Genetics and Cytogenetics, 202:33-37 (2010).
Baljevic, M. et al., Telomere Length Recovery: A Strong Predictor of Overall Survival in Acute Promyelocytic Leukemia, Acta Haematol, 136:210-218 (2016).
Bruyere, H. et al., Concomitant and successive amplifications of MYC in APL-like leukemia, Cancer Genetics and Cytogenetics, 197:75-80 (2010).
Cao, Y. et al., Oridonin stabilizes retinoic acid receptor alpha through ROS-activated NF-kB signaling, BMC Cancer, 15:248, 12 pages (2015).
Elias, S. et al., Immune evasion by oncogenic proteins in acute myeloid leukemia, Blood, 123(10):1535-1543 (2014).
Fang, Y. et al., Inhibition of All-Trans-Retinoic Acid-Induced Proteasome Activation Potentiates the Differentiating Effect of Retinoid in Acute Myeloid Leukemia Cells, Molecular Carcinogenesis, 50:24-35 (2011).
Fang, Y. et al., PML-RARa modulates the vascular signature of extracellular vesicles released by acute promyelocytic leukemia cells, Angiogenesis, 19:25-38 (2016).
Fu, Y. et al., Clinical significance of lymphoid enhancer-binding factor 1 expression in acute myeloid leukemia, Leukemia & Lymphoma, 55(2):371-377 (2014).
Gao, Y. et al., PML(NLS-) Inhibits Cell Apoptosis and Promotes Proliferation in HL-60 Cells, Int. J. Med. Sci., 10(5):498-507 (2013).
Garattini, E. et al., Retinoids and breast cancer: From basic studies to the clinic and back again, Cancer Treatment Reviews, 40:739-749 (2014).
Garattini, E. et al., Retinoids and breast cancer: new clues to increase their activity and selectivity, Breast Cancer Res, 14(5):111 2 pages, (2012).
Glynn, R.W. et al., 17q12-21—The pursuit of targeted therapy in breast cancer, Cancer Treatment Reviews, 36:224-229 (2010).
Gruver, A. et al., Modified Array-based Comparative Genomic Hybridization Detects Cryptic and Variant PML-RARA Rearrangements in Acute Promyelocytic Leukemia Lacking Classic Translocations, Diagn Mol Pathol., 22:10-21 (2013).

(Continued)

*Primary Examiner* — James D. Anderson
(74) *Attorney, Agent, or Firm* — Brenda Herschbach Jarrell; Janet M. Tse; Choate, Hall & Stewart LLP

(57) ABSTRACT

Described herein are methods that define cellular populations that are sensitive to RARA agonists and identify patient populations that will benefit from treatment with RARA agonists. The methods may comprise administering RARA agonists to patient populations.

27 Claims, 21 Drawing Sheets

(56) References Cited

OTHER PUBLICATIONS

Hasan, S. et al., Analysis of t(15;17) Chromosomal Breakpoint Sequences in Therapy-Related Versus De Novo Acute Promyelocytic Leukemia: Association of DNA Breaks with Specific DNA Motifs at PML and RARA Loci, Genes, Chromosomes & Cancer, 49:726-732 (2010).
Hashimoto, Y. et al., Development of Reverse Transcription Loop-Mediated Isothermal Amplification for Simple and Rapid Detection of Promyelocytic Leukemia-Retinoic Acid Receptor α mRNA, Yonago Acta medica, 59:262-269 (2016).
Hu, X. et al., Effect of Recombinant Adenovirus Carrying NLS-RARα Gene on the Proliferation of HL-60 Cell and the Differentiation of HL-60 Cells Induced by ATRA and Mechanism, J. Sichuan Univ. (Med Sci Edi), 44(6):897-901 (2013) English Abstract.
Hu, X. et al., NLS-RARα Promotes Proliferation and Inhibits Differentiation in HL-60 Cells, Int. J. Med. Sci., 11:247-254 (2014).
Humbert, M. et al., The tumor suppressor gene DAPK2 is induced by the myeloid transcription factors PU.1 and C/EBPα during granulocytic differentiation but repressed by PML-RARα in APL, Journal of Leukocyte Biology, 95(1):83-93 (2014).
International Search Report for PCT/US2016/025256, 3 pages (dated Aug. 8, 2016).
International Search Report for PCT/US2017/026657, 7 pages (dated Aug. 28, 2017).
Iwasaki, J. et al., FIP1L1 presence in FIP1L1-RARA or FIP1L1-PDGFRA differentially contributes to the pathogenesis of distinct types of leukemia, Ann Hematol, 93:1473-1481 (2014).
Jeziskova, I. et al., A Case of a Novel PML/RARA Short Fusion Transcript with Truncated Transcription Variant 2 of the RARA Gene, Mol Diagn Ther., 14(2):113-117 (2010).
Jo, S. et al., Korean red ginseng extract induces proliferation to differentiation transition of human acute promyelocytic leukemia cells via MYC-SKP2-CDKN1B axis, Journal of Ethnopharmacology, 150:700-707 (2013).
Johnson, D. and Redner, R., An ATRActive future for differentiation therapy in AML, Blood Reviews, 29:263-268 (2015).
Kunter, G. et al., A truncation mutant of Csf3r cooperates with PML-RARα to induce acute myeloid leukemia in mice, Exp Hematol., 39(12):1136-1143 (2011).
Lai, C. et al., Unusual acute promyelocytic leukemia following de novo renal transplant: case report and literature review, Clinical Nephrology, 75-Suppl. 1:S27-S31 (2011).
Laursen, K. et al., Epigenetic regulation by RARα maintains ligand-independent transcriptional activity, Nucleic Acids Research, 40(1):102-115 (2012).
Lewis, C. et al., Microgranular variant of acute promyelocytic leukemia with normal conventional cytogenetics, negative PML/RARA FISH and positive PML/RARA transcripts by RT-PCR, Cancer Genetics, 204:522-523 (2011).
Li, Z. et al., FTO Plays an Oncogenic Role in Acute Myeloid Leukemia as a N6-Methyladenosine RNA Demethylase, Cancer Cell, 31:127-141 (2017).
Liu, Y. et al., Tetra-arsenic tetra-sulfide (As4S4) promotes apoptosis in retinoid acid-resistant human acute promyelocytic leukemic NB4-R1 cells through downregulation of SET protein, Tumor Biol., 10 pages (2013).
Luo, H. et al., Effect of siRNA Targeting PML-RARα Fusion Gene on Activity of the Acute Promyelocytic Leukemia Cell Line NB4, Journal of Biological Engineering, 31(4):850-854 (2014) English Abstract.
Marchwicka, A. et al., Regulation of vitamin D receptor expression by retinoic acid receptor alpha in acute myeloid leukemia cells, Journal of Steroid Biochemistry & Molecular Biology, 159:121-130 (2016).
Martin-Subero, J.I., et al., Amplification of ERBB2, RARA and TOP2A genes in a myelodysplastic syndrome transforming to acute myeloid leukemia, Cancer Genetics and Cytogenetics, 127:174-176 (2001).
Menezes, J. et al., FIP1L1/RARA with breakpoint at FIP1L1 intron 13: a variant translocation in acute promyelocytic leukemia, Haematologica, 96(10):1565-1566 (2011).
Morikawa, K. et al., All-trans retinoic acid displays multiple effects on the growth, lipogenesis and adipokine gene expression of AML-I preadipocyte cell line, Cell Biology International, 37:36-46 (2013).
Occhionorelli, M. et al., the self-association coiled-coil domain of PML is sufficient for the oncogenic conversion of the retinoic acid receptor (RAR) alpha, Leukemia, 25:814-820 (2011).
Oh, S.J. et al., Acute Promyelocytic Leukemia with a RARE PML Exon 4/RARA Exon 3 Fusion Transcript Variant, Acta Haematologica, 130:176-180 (2013).
Paroni, G. et al., Synergistic antitumor activity of lapatinib and retinoids on a novel subtype of breast cancer with coamplification of ERBB2 and RARA, Oncogene, 31:3431-3443 (2012).
Perri, M. et al., BCL-xL/MCL-1 inhibition and RARγ antagonism work cooperatively in human HL60 leukemia cells, Exp Cell Res., 327(2):183-191 (2014).
Pogosova-Agadjanyan, E. et al., The Prognostic Significance of IRF8 Transcripts in Adult Patients with Acute Myeloid Leukemia, PLOS ONE, 8(8):e70812, 13 pages (2013).
Polampalli, S. et al., Role of RT-PCR and FISH in diagnosis and monitoring of acute promyelocytic leukemia, Indian Journal of Cancer, 48(1):60-67 (2011).
Pu, L. et al., The First Switched Time of PML/RARα Fusion Gene in Patients with Acute Promyelocytic Leukemia and Its Clinical Significance, Journal of Experimental Hematology, 23(6):1551-1555 (2015) English Abstract.
Qi, X. et al., The PML Gene of the PML-RARα V-Form Fusion Transcript Breaks within Exon 6, Acta Haematol, 126:216-219 (2011).
Saeed, S. et al., Chromatin accessibility, p300, and histone acetylation define PML-RARα and AML1-ETO binding sites in acute myeloid leukemia, Blood, 120(15):3058-3068 (2012).
Saito, A. et al., DIC Complicating APL Successfully Treated With Recombinant Thrombomodulin Alfa, J Pediatr Hematol Oncol, 38(6):e189-e190 (2016).
Sanford, D. et al., Tamibarotene in patients with acute promyelocytic leukaemia relapsing after treatment with all-trans retinoic acid and arsenic trioxide, British Journal of Haematology, 171:471-477 (2015).
Seshire, A. et al., Direct interaction of PU.1 with oncogenic transcription factors reduces its serine phosphorylation and promoter binding, Leukemia, 26:1338-1347 (2012).
Shigeto, S. et al., Rapid diagnosis of acute promyelocytic leukemia with the PML-RARA fusion gene using a combination of droplet-reverse transcription-polymerase chain reaction and instant-quality fluorerscence in situ hybridization, Clinica Chimica Acta, 453:38-41 (2016).
Shimomura, Y. et al., New variant of acute promyelocytic leukemia with IRF2BP2-RARA fusion, Cancer Sci., 107:1165-1168 (2016).
Soriani, S. et al., PML/RAR-α fusion transcript and polyploidy in acute promyelocytic leukemia without t(15;17), Leukemia Research, 34:e261-e263 (2010).
Sueki, A. et al., Rapid detection of PML-RARA fusion gene by novel high-speed droplet-reverse transcriptase-polymerase chain reaction: Possibility for molecular diagnosis without lagging behind the morphological analyses, Clinica Chimica Acta, 415:276-278 (2013).
Takahashi, H. et al., Induced differentiation of human myeloid leukemia cells into M2 macrophages by combined treatment with retinoic acid and 1?,25-dihydroxyvitamin D3, PLoS One, 9(11):e113722, 9 pages, (2014).
Tamura, T. et al., Regulation of myelopoiesis by the transcription factor IRF8, Int J. Hematol, 101:342-351 (2015).
Tian, Y. et al., Arsenic Sulfide Promotes Apoptosis in Retinoid Acid Resistant Human Acute Promyelocytic Leukemic NB4-R1 Cells through Downregulation of SET Protein, PLOS One, 9(1):e83184, 8 pages (2014).
Valleron, W. et al., Specific small nucleolar RNA expression profiles in acute leukemia, Leukemia, 26:2052-2060 (2012).

(56) References Cited

OTHER PUBLICATIONS

Vourtsis, D. et al., Effect on all-trans-retinoic acid conjugate with spermine on viability of human prostate cancer and endothelial cells in vitro and angiogenesis in vivo, European Journal of Pharmacology, 698:122-130 (2013).

Walz, C. et al., Atypical mRNA fusions in PML-RARA positive, RARA-PML negative acute promyelocytic leukemia, Genes Chromosomes Cancer, 49(5):471-479 (2010).

Welch, J. et al., PML-RARA can increase hematopoietic self-renewal without causing a myeloproliferative disease in mice, The Journal of Clinical Investigation, 121(4):1636-1645 (2011).

Written Opinion for PCT/US2016/025256, 8 pages (dated Aug. 8, 2016).

Written Opinion for PCT/US2017/026657, 12 pages (dated Aug. 28, 2017).

Xu, Y. et al., All-trans retinoic acid is capable of inducing folate receptor β expression in KG-1 cells, Tumor Biol., 31:589-595 (2010).

Yamamoto, K. et al., Persistent Hypoplastic Acute Promyelocytic Leukemia with a Novel Chromosomal Abnormality of 46, XY, t(15;17), t(9;11)(q13;p13), J Clin Exp Hematop, 55(2):71-76 (2015).

Yamamoto, Y. et al., BCOR as a novel fusion partner of retinoic acid receptor alpha in a t(X;17)(p11;q12) variant of acute promyelocytic leukemia, Blood, 116(20):4274-4283 (2010).

Yuan, C. et al., A112, a tamibarotene dimethylaminoethyl ester, may inhibit human leukemia cell growth more potently than tamibarotene, Leuk Lymphoma, 53(2):295-304 (2012).

Zhang, Y. et al., Arsenic trioxide suppresses transcription of hTERT through down-regulation of multiple transcription factors in HL-60 leukemia cells, Toxicol Lett., 232(2):481-489 (2015).

Zhu, X. et al., The significance of low PU.1 expression in patients with acute promyelocytic leukemia, Journal of Hematology & Oncology, 5:22, 6 pages (2012).

Zou, D. et al., Regulation of the hematopoietic cell kinase (HCK) by PML/RARα and PU.1 in acute promyelocytic leukemia, Leukemia Research, 36:219-223 (2012).

METHODS OF STRATIFYING PATIENTS FOR TREATMENT WITH RETINOIC ACID RECEPTOR-ALPHA AGONISTS

CROSS-REFERENCE TO RELATED APPLICATIONS

This application is a continuation of U.S. application Ser. No. 15/582,311 filed Apr. 28, 2017, now U.S. Pat. No. 9,868,994, which is a continuation of International Application No. PCT/US17/26657 filed Apr. 7, 2017, which claims the benefit of and priority to U.S. provisional patent application Ser. No. 62/320,352, filed Apr. 8, 2016, the disclosures of each of which are hereby incorporated by reference in their entireties.

BACKGROUND OF THE INVENTION

Retinoids are a class of compounds structurally related to vitamin A, comprising natural and synthetic compounds. Several series of retinoids have been found clinically useful in the treatment of dermatological and oncological diseases. Retinoic acid and its other naturally occurring retinoid analogs (9-cis retinoic acid, all-trans 3,4-didehydro retinoic acid, 4-oxo retinoic acid and retinol) are pleiotropic regulatory compounds that modulate the structure and function of a wide variety of inflammatory, immune and structural cells. They are important regulators of epithelial cell proliferation, differentiation, and morphogenesis in lungs. Retinoids exert their biological effects through a series of hormone nuclear receptors that are ligand inducible transcription factors belonging to the steroid/thyroid receptor super family.

The retinoid receptors are classified into two families, the retinoic acid receptors (RARs) and the retinoid X receptors (RXRs), each consisting of three distinct subtypes ($\alpha$, $\beta$, and $\gamma$). Each subtype of the RAR gene family encodes a variable number of isoforms arising from differential splicing of two primary RNA transcripts. All-trans retinoic acid is the physiological hormone for the retinoic acid receptors and binds with approximately equal affinity to all the three RAR subtypes, but does not bind to the RXR receptors for which 9-cis retinoic acid is the natural ligand. Retinoids have anti-inflammatory effects, alter the progression of epithelial cell differentiation, and inhibit stromal cell matrix production. These properties have led to the development of topical and systemic retinoid therapeutics for dermatological disorders such as psoriasis, acne, and hypertrophic cutaneous scars. Other applications include the control of acute promyelocytic leukemia, adeno- and squamous cell carcinoma, and hepatic fibrosis.

A limitation in the therapeutic use of retinoids has stemmed from the relative toxicity observed with the naturally occurring retinoids, all-trans retinoic acid and 9-cis retinoic acid. These natural ligands are non-selective in terms of RAR subtype and therefore have pleiotropic effects throughout the body, which are often toxic.

Various retinoids have been described that interact selectively or specifically with the RAR or RXR receptors or with specific subtypes ($\alpha$, $\beta$, $\gamma$) within a class. RARA specific agonists have held high promise for the treatment of cancers and many have entered human clinical trials. However, only one RARA specific agonist, tamibarotene, has ever been approved for the treatment of cancer. Moreover, tamibarotene is only approved in Japan and only for the treatment of acute promyelocytic leukemia, despite trials in the US and Europe. The disconnect between the theoretical efficacy of RARA agonists in cancer and the dearth of regulatory approvals for such agents raises the question of why such agonists are not effective and safe in humans. Therefore, there is a need to better understand why RARA agonists have not met their therapeutic potential.

Recent advances in genomic technology and the understanding of gene regulatory circuits has led to the discovery of super enhancers. Whereas many genes in a given tissue or cancer type may be regulated by the presence of enhancers in proximity to the gene coding region, a small minority of these represent a highly asymmetric and disproportionately large loading of transcriptional marks and machinery relative to all other active genes. Recent discoveries suggest that such enhancers are tied to genes of special relevance to the function and survival of the cell harboring them. As such, an association of a super enhancer with a gene indicates the relative significance of said gene to the survival of that cell.

SUMMARY OF THE INVENTION

The present disclosure provides technologies for detecting one or more IRF8 biomarkers (e.g., presence, level, form, and/or activity of one or more IRF8 gene components or products, including for example IRF8 super enhancer strength, ordinal rank, or prevalence rank and IRF8 mRNA level or prevalence rank). The present disclosure demonstrates that cells (e.g., cancer cells or cells from a subject suffering from non-APL AML or MDS) containing one or more IRF8 biomarkers, wherein the IRF8 biomarker is or comprises expression of one or more of elevated IRF8 mRNA levels or a super enhancer associated with an IRF8 gene are more susceptible to the effects of a RARA agonist, such as tamibarotene.

The various embodiments, aspects and alternatives of this invention solve the problem of defining which cellular populations are sensitive to agonists of retinoic acid receptor alpha ("RARA"), identifying patient populations that will benefit from treatment with RARA agonists (e.g., stratifying patients for treatment with a RARA agonist; separating RARA agonist responders from non-responders) and providing treatment therapies directed at such patient populations. The solution is based, at least in part, upon our discovery that elevated expression of one or more IRF8 biomarkers in certain cancer cells is indicative that such cells will be substantially more responsive" than similar cells that do not have an elevated IRF8 biomarker to treatment with a RARA agonist (e.g., tamibarotene).

In some embodiments, the present disclosure relates to a method of treating cancer (e.g., non-APL AML or MDS) in a subject (e.g., a human) based on the level of IRF8 mRNA in the subject's cancer cells, wherein the method comprises a step of administering to the subject an amount of a RARA agonist (e.g., tamibarotene) effective to treat the disease. In some aspects of these embodiments, the level of IRF8 mRNA in the subject's cancer cells is equal to or above a pre-determined threshold level.

In some embodiments, the present disclosure relates to a method of treating cancer, wherein the method comprises a step of administering tamibarotene to a subject having a cancer, wherein the cancer is determined to have an IRF8 biomarker, wherein the IRF8 biomarker is or comprises expression of one or more of elevated IRF8 mRNA levels or a super enhancer associated with an IRF8 gene.

In some embodiments, the present disclosure relates to a method comprising a step of administering therapy to a subject determined not to express one or more of elevated RARA mRNA levels or a super enhancer associated with a RARA gene; and not to express one or more of elevated IRF8 mRNA levels or a super enhancer associated with an IRF8 gene, wherein the therapy does not include administration of tamibarotene.

In some embodiments, the present disclosure relates to a method of treating cancer, the method comprising a step of administering therapy to a subject determined (a) not to express one or more of elevated RARA mRNA levels or not to have a super enhancer associated with a RARA gene whose strength and/or ordinal rank is above a pre-determined threshold; and (b) to express one or more of elevated IRF8 mRNA levels or a super enhancer associated with an IRF8 gene, wherein the therapy is tamibarotene.

In some embodiments, the present disclosure relates to a method of treating cancer, the method comprising a step of administering therapy to a subject determined not to express one or more of elevated RARA mRNA levels or a super enhancer associated with a RARA gene; and to express one or more of elevated IRF8 mRNA levels or a super enhancer associated with an IRF8 gene, wherein the therapy is tamibarotene.

In some embodiments, the present disclosure relates to a method of treating cancer, the method comprising steps of receiving information related to IRF8 mRNA level in a subject suffering from a cancer; and administering to the subject tamibarotene if the information indicates the IRF8 mRNA level or super enhancer level is equal to or above that of a reference. In some aspects, a reference is a pre-determined threshold. In some aspects, a pre-determined threshold is a cutoff value or a prevalence cutoff.

In some embodiments, the present disclosure relates to a method of treating cancer, the method comprising steps of receiving information related to the presence of a super enhancer associated with an IRF8 gene in a subject suffering from a cancer; and administering to the subject tamibarotene if the information indicates that a super enhancer is associated with an IRF8 gene.

In some embodiments, the present disclosure relates to a method of predicting the efficacy of a RARA agonist in a treatment of a cancer comprising the steps of determining if the cancer comprises a cell having IRF8 mRNA level that is equal to or above that of a reference, wherein the IRF8 mRNA level is equal to or above that of a reference is predictive of RARA agonist efficacy in the treatment. In some aspects, a reference is a pre-determined threshold. In some aspects, a pre-determined threshold is a cutoff value or a prevalence cutoff.

In some embodiments, the present disclosure relates to a method of predicting the efficacy of a RARA agonist in a treatment of a cancer comprising the steps of determining if, in a subject suffering from a cancer, the cancer comprises a cell that has a super enhancer associated with an IRF8 gene, wherein the presence of a super enhancer associated with an IRF8 gene indicates efficacious treatment of the cancer with a RARA agonist.

In some embodiments, the present disclosure relates to a method comprising steps of obtaining a biological sample comprising cancer cells from a subject suffering from cancer; and detecting in the biological sample one or more of IRF8 mRNA level is equal to or above that of that of a reference; or a super enhancer associated with an IRF8 gene. In some aspects, a reference is a pre-determined threshold. In some aspects, a pre-determined threshold is a cutoff value or a prevalence cutoff.

In some embodiments, the present disclosure relates to a method of diagnosing, prognosing, or treating a subject suffering from a cancer comprising the steps of obtaining a sample of the cancer from the subject; and determining in the sample one or more of an IRF8 mRNA level or the presence of a super enhancer associated with an IRF8 gene in the subject.

In some embodiments, the present disclosure relates to a method of diagnosing, prognosing, or treating a subject suffering from a cancer comprising the steps of obtaining a sample of the cancer from the subject; determining in the sample IRF8 mRNA level or the presence of a super enhancer associated with an IRF8 gene in the subject; and administering a therapeutic composition comprising a RARA agonist if one or more of (a) IRF8 mRNA level is equal to or above that of that of a reference; or (b) a super enhancer associated with an IRF8 gene. In some aspects, a reference is a pre-determined threshold. In some aspects, a pre-determined threshold is a cutoff value or a prevalence cutoff.

In some embodiments, the present disclosure relates to a method comprising detecting one or more of RARA mRNA level or the strength or ordinal rank of a super enhancer associated with a RARA gene in a biological sample obtained from a subject with a cancer; and detecting one or more of IRF8 mRNA level or a super enhancer associated with an IRF8 gene in the biological sample if the biological sample does not express one or more of elevated RARA mRNA level equal to above that of a reference or a super enhancer associated with a RARA gene which has a strength or ordinal rank that is equal to or above a pre-determined threshold. In some aspects, a reference is a pre-determined threshold. In some aspects, a pre-determined threshold is a cutoff value or a prevalence cutoff.

In some embodiments, the present disclosure relates to a method comprising detecting one or more of RARA mRNA level or the strength or ordinal rank of a super enhancer associated with a RARA gene in a biological sample obtained from a subject with a cancer; and detecting one or more of IRF8 mRNA level or a super enhancer associated with an IRF8 gene in the biological sample if the biological sample does express one or more of elevated RARA mRNA level equal to above that of a reference or a strength or ordinal rank of a super enhancer associated with a RARA gene which is equal to or above a pre-determined threshold.

In some embodiments, the present disclosure relates to a method comprising detecting one or more of IRF8 mRNA level or a super enhancer associated with an IRF8 gene in a biological sample obtained from a subject with a cancer; and detecting one or more of RARA mRNA level or the strength or ordinal rank of a super enhancer associated with a RARA gene in the biological sample if the biological sample does not express one or more of elevated IRF8 mRNA level equal to above that of a reference or a super enhancer associated with an IRF8 gene.

In some embodiments, the present disclosure relates to a method comprising detecting one or more of IRF8 mRNA level or a super enhancer associated with an IRF8 gene in a biological sample obtained from a subject with a cancer; and detecting one or more of RARA mRNA level or the strength or ordinal rank of a super enhancer associated with a RARA gene in the biological sample if the biological sample does express one or more of elevated IRF8 mRNA level equal to above that of a reference or a super enhancer associated with an IRF8 gene.

In some embodiments, the present disclosure relates to a method of diagnosing and treating a human subject suffering from a disease selected from non-APL AML and MDS, the method comprising:

a. diagnosing whether the subject has a tamibarotene-sensitive form of the disease based on a level of IRF8 mRNA previously determined to be present in a sample of diseased cells from the subject; and b. administering to the subject an amount of tamibarotene effective to treat the disease.

In some aspects of these embodiments, the level of IRF8 mRNA is equal to or above a pre-determined threshold.

In some aspects of any of the foregoing embodiments which comprise the treatment of a subject with tamibarotene, the subject is administered a combination of tamibarotene and a second therapeutic agent.

In some embodiments, the present disclosure relates to a method of treating a cancer selected from non-APL or MDS in a subject based upon a level of RARA mRNA and or a level of IRF8 mRNA in the subject's cancer cells, wherein the treatment comprises administering to the subject a combination of tamibarotene and a second therapeutic agent. In some aspects of these embodiments, the subject has a RARA mRNA level equal to or above a threshold value. In some aspects of these embodiments, the subject has an IRF8 mRNA level equal to or above a threshold value. In some aspects of these embodiments, the subject has both a RARA mRNA level equal to or above a threshold value and an IRF8 mRNA level equal to or above a threshold value. In some aspects of these embodiments, the subject is suffering from non-APL AML.

BRIEF DESCRIPTION OF THE DRAWINGS

FIG. 11 also depicts the % $CD45^+$ cells in different organs and biological fluids, as well as the time of survival of the mouse models.

FIG. 12 also depicts the % $CD45^+$ cells in different organs and biological fluids in those models, as well as the time of survival in those models.

DEFINITIONS

Figure 1:
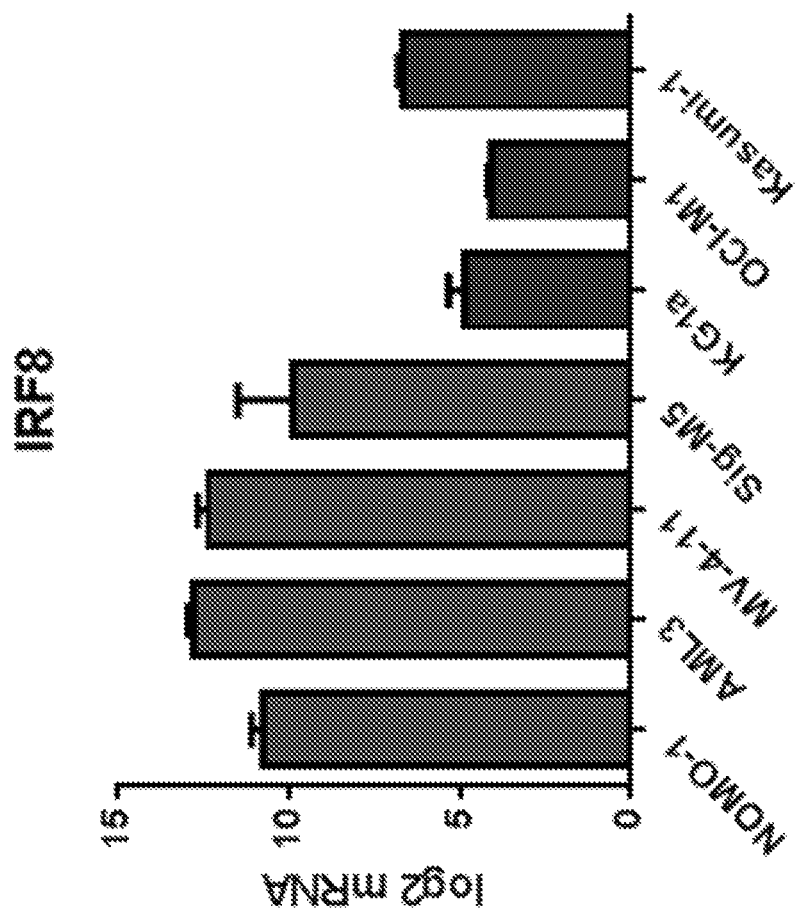
FIG. 1 depicts IRF8 mRNA levels in seven different AML cell lines. Cell lines indicated by the red bars demonstrate substantial responsiveness to tamibarotene treatment. Cell lines indicated by the blue bars demonstrate little or no responsiveness to tamibarotene treatment.

In this application, unless otherwise clear from context, (i) the term "a" may be understood to mean "at least one"; (ii) the term "or" may be understood to mean "and/or"; (iii) the terms "comprising" and "including" may be understood to encompass itemized components or steps whether presented by themselves or together with one or more additional components or steps; and (iv) the terms "about" and "approximately" may be understood to permit standard variation as would be understood by those of ordinary skill in the art; and (v) where ranges are provided, endpoints are included.

Those skilled in the art will appreciate that one or more chemical compounds whose structure is depicted herein may have one or more isomeric (e.g., enantiomeric, diastereomeric, and geometric (or conformational)) and/or tautomeric forms; for example, R and S configurations for each asymmetric center, Z and E double bond isomers, and Z and E conformational isomers. In some embodiments, teachings included herein may be applicable to and/or encompass any and all such forms. Therefore, unless otherwise stated, single stereochemical isomers as well as enantiomeric, diastereomeric, and geometric (or conformational) mixtures of the present compounds may all be within the scope of the invention. Similarly, unless otherwise stated, all tautomeric forms of the compounds of the invention are within the scope of the invention. Furthermore, those skilled in the art will appreciate that, in some embodiments, chemical structures depicted herein may encompass compounds that differ only in the presence of one or more isotopically enriched atoms. For example, compounds whose structure is identical to that depicted except for replacement of hydrogen by deuterium or tritium, or replacement of a carbon by a $^{13}$C- or $^{14}$C-enriched carbon, are within the scope of this invention. In certain embodiments, such compounds may be useful, for example, as analytical tools, as probes in biological assays, and/or as therapeutic agents in accordance with the present invention.

Agonist: As used herein, the term "agonist" may be used to refer to an agent, condition, or event whose presence, level, degree, type, or form correlates with increased level or activity of another agent (i.e., the agonized agent). In general, an agonist may be or include an agent of any chemical class including, for example, small molecules, polypeptides, nucleic acids, carbohydrates, lipids, metals, and/or any other entity that shows the relevant activating activity. In some embodiments, an agonist may be direct (in which case it exerts its influence directly upon its target); in some embodiments, an agonist may be indirect (in which case it exerts its influence by other than binding to its target; e.g., by interacting with a regulator of the target, so that level or activity of the target is altered).

Agonist Therapy: As used herein, the term "agonist therapy" refers to administration of an agonist that agonizes a particular target of interest to achieve a desired therapeutic effect. In some embodiments, agonist therapy involves administering a single dose of an agonist. In some embodiments, agonist therapy involves administering multiple doses of an agonist. In some embodiments, agonist therapy involves administering an agonist according to a dosing regimen known or expected to achieve the therapeutic effect, for example, because such result has been established to a designated degree of statistical confidence, e.g., through administration to a relevant population.

Antagonist: As used herein, the term "antagonist" may be used to refer to an agent, condition, or event whose presence, level, degree, type, or form correlates with decreased level or activity of another agent (e.g., the inhibited agent, or target). In general, an antagonist may be or include an agent of any chemical class including, for example, small molecules, polypeptides, nucleic acids, carbohydrates, lipids, metals, and/or any other entity that shows the relevant inhibitory activity. In some embodiments, an antagonist may be direct (in which case it exerts its influence directly upon its target); in some embodiments, an antagonist may be indirect (in which case it exerts its influence by other than binding to its target; e.g., by interacting with a regulator of the target, so that level or activity of the target is altered).

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Acute Promyelocytic Leukemia: As used herein, the term "Acute Promyelocytic Leukemia" or "APL" refers to a subtype of acute myelogenous leukemia ("AML") characterized by a genetic translocation between human chromosomes 15 and 17. Accordingly, the term "Non-APL AML" refers to any subtype of AML that is not characterized by such a genetic translocation.

Biological sample: As used herein, the term "biological sample" refers to any sample obtained from an individual suffering from a disease to be treated by the methods of this invention, including tissue samples (such as tissue sections and needle biopsies of a tissue); cell samples (e.g., cytological smears (such as Pap or blood smears) or samples of cells obtained by microdissection); bone marrow samples (either whole, complete cell fractions thereof, or subpopulations of cells therein); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucus, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample. In some aspects, a biological sample from a subject suffering from non-APL AML or MDS is a bone marrow aspirate. In other aspects, a biological sample from a subject suffering from non-APL AML or MDS is a fractionated whole blood sample. In more specific aspects, a biological sample from a subject suffering from non-APL AML or MDS is a PBMC fraction from the subject's whole blood (a "PBMC sample"). In still more specific aspects, a PBMC sample from a subject suffering from non-APL AML or MDS is further enriched for specific blasts using various enrichment techniques such as antibody-linked bead enrichment protocols, fluorescent label cell sorting, or other techniques known in the art (an "enriched PBMC sample"). In some embodiments, as will be clear from context, the term "sample" refers to a preparation that is obtained by processing (e.g., by removing one or more components of and/or by adding one or more agents to) a primary sample. Such a "processed sample" may comprise, for example nucleic acids or proteins extracted from a sample or obtained by subjecting a primary sample to techniques such as amplification or reverse transcription of mRNA, isolation and/or purification of certain components, etc.

Biomarker: As used herein, the term "biomarker" refers to an entity whose presence, level, or form, correlates with a particular biological event or state of interest, so that it is considered to be a "marker" of that event or state. To give but a few examples, in some embodiments, a biomarker may be or comprises a marker for a particular disease state or stage, or for likelihood that a particular disease, disorder or condition may develop. In some embodiments, a biomarker may be or comprise a marker for a particular disease or therapeutic outcome, or likelihood thereof. Thus, in some embodiments, a biomarker is predictive, in some embodiments, a biomarker is prognostic, in some embodiments, a biomarker is diagnostic, of the relevant biological event or state of interest. A biomarker may be an entity of any chemical class. For example, in some embodiments, a biomarker may be or comprise a nucleic acid, a polypeptide, a lipid, a carbohydrate, a small molecule, an inorganic agent (e.g., a metal or ion), or a combination thereof. In some embodiments, a biomarker is a cell surface marker. In some embodiments, a biomarker is intracellular. In some embodiments, a biomarker is found outside of cells (e.g., is secreted or is otherwise generated or present outside of cells, e.g., in a body fluid such as blood, urine, tears, saliva, cerebrospinal fluid, etc. In some embodiments, term refers to a gene expression product that is characteristic of a particular tumor, tumor subclass, stage of tumor, etc. Alternatively or additionally, in some embodiments, a presence or level of a particular marker correlates with activity (or activity level) of a particular signaling pathway, for example that may be characteristic of a particular class of tumors. The statistical significance of the presence or absence of a biomarker may vary depending upon the particular biomarker. In some embodiments, detection of a biomarker is highly specific in that it reflects a high probability that the tumor is of a particular subclass. Such specificity may come at the cost of sensitivity (e.g., a negative result may occur even if the tumor is a tumor that would be expected to express the biomarker). In some embodiments, a biomarker may be or comprise an IRF8 biomarker (e.g., presence, level, form, and/or activity of one or more IRF8 gene components or products, including for example IRF8 super enhancer strength, ordinal rank, or prevalence rank and IRF8 mRNA level or prevalence rank). In some embodiments, a biomarker may include a RARA biomarker (e.g., one or more RARA biomarkers (e.g., presence, level, form, and/or activity of one or more RARA gene components or products, including for example RARA super enhancer strength, ordinal rank, or prevalence rank and RARA mRNA level or prevalence rank). In some embodiments a biomarker refers to a combination of one or more biomarkers, such as IRF8 and RARA.

Cancer: As used herein, the term "cancer" refers to a malignant neoplasm or tumor (*Stedman's Medical Dictionary*, 25th ed.; Hensly ed.; Williams & Wilkins: Philadelphia, 1990). The terms "neoplasm" and "tumor" are used herein interchangeably and refer to an abnormal mass of tissue wherein the growth of the mass surpasses and is not coordinated with the growth of a normal tissue. A "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites. In some embodiments a cancer is any malignant neoplasm or tumor wherein an IRF8 biomarker is correlated with responsiveness to a RARA agonist such as tamibarotene. In some embodiments a cancer is acute myelocytic leukemia (AML). In some embodiments a cancer is non-APL AML.

Combination therapy: As used herein, the term "combination therapy" refers to those situations in which a subject is simultaneously exposed to two or more therapeutic regimens (e.g., two or more therapeutic agents). In some embodiments, two or more agents or may be administered simultaneously; in some embodiments, such agents may be administered sequentially; in some embodiments, such agents are administered in overlapping dosing regimens. In some embodiments, "administration" of combination therapy may involve administration of one or more agents to a subject receiving the other agents in the combination. For clarity, combination therapy does not require that individual agents be administered together in a single composition (or even necessarily at the same time), although in some embodiments, two or more active agents, entities, or moieties may be administered together in a combination composition, or even in a combination compound (e.g., as part of a single chemical complex or covalent entity).

Cutoff value: As used herein, the terms "cutoff" and "cutoff value" means a value measured in an assay that defines the dividing line between two subsets of a population (e.g., responders and non-responders). Thus, a value that is equal to or higher than the cutoff value defines one subset of the population; and a value that is lower than the cutoff value defines the other subset of the population.

Diagnostic information: As used herein, "diagnostic information" or "information for use in diagnosis" is information that is useful in determining whether a patient has a disease, disorder or condition and/or in classifying a disease, disorder or condition into a phenotypic category or any category having significance with regard to prognosis of a disease, disorder or condition, or likely response to treatment (either treatment in general or any particular treatment) of a disease, disorder or condition. Similarly, "diagnosis" refers to providing any type of diagnostic information, including, but not limited to, whether a subject is likely to have or develop a disease, disorder or condition, state, staging or characteristic of a disease, disorder or condition as manifested in the subject, information related to the nature or classification of a tumor, information related to prognosis and/or information useful in selecting an appropriate treatment. Selection of treatment may include the choice of a particular therapeutic agent or other treatment modality such as surgery, radiation, etc., a choice about whether to withhold or deliver therapy, a choice relating to dosing regimen (e.g., frequency or level of one or more doses of a particular therapeutic agent or combination of therapeutic agents), etc.

Dosage form or unit dosage form: Those skilled in the art will appreciate that the term "dosage form" may be used to refer to a physically discrete unit of an active agent (e.g., a therapeutic or diagnostic agent) for administration to a subject. Typically, each such unit contains a predetermined quantity of active agent. In some embodiments, such quantity is a unit dosage amount (or a whole fraction thereof) appropriate for administration in accordance with a dosing regimen that has been determined to correlate with a desired or beneficial outcome when administered to a relevant population (i.e., with a therapeutic dosing regimen). Those of ordinary skill in the art appreciate that the total amount of a therapeutic composition or agent administered to a particular subject is determined by one or more attending physicians and may involve administration of multiple dosage forms.

Dosing regimen: Those skilled in the art will appreciate that the term "dosing regimen" may be used to refer to a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which is separated in time from other doses. In some embodiments, individual doses are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount In some embodiments, a dosing regimen is correlated with a desired or beneficial outcome when administered across a relevant population (i.e., is a therapeutic dosing regimen).

Effective amount: As used herein, an "effective amount" of a compound described herein, such as of Formula (I) refers to an amount sufficient to elicit the desired biological response, i.e., treating the condition. As will be appreciated by those of ordinary skill in this art, the effective amount of a compound described herein, such as of Formula (I) may vary depending on such factors as the desired biological endpoint, the pharmacokinetics of the compound, the condition being treated, the mode of administration, and the age and health of the subject. An effective amount encompasses therapeutic and prophylactic treatment. For example, in treating cancer, an effective amount of an inventive compound may reduce the tumor burden or stop the growth or spread of a tumor.

Enhancer: As used herein, the term "enhancer" refers to a region of genomic DNA acting to regulate genes up to 1 Mbp away. An enhancer may overlap, but is often not composed of, gene coding regions. An enhancer is often bound by transcription factors and designated by specific histone marks.

Hydrate: As used herein, the term "hydrate" refers to a compound which is associated with water. Typically, the number of the water molecules contained in a hydrate of a compound is in a definite ratio to the number of the compound molecules in the hydrate. Therefore, a hydrate of a compound may be represented, for example, by the general formula $Rx H_2O$, wherein R is the compound and wherein x is a number greater than 0. A given compound may form more than one type of hydrates, including, e.g., monohydrates (x is 1), lower hydrates (x is a number greater than 0 and smaller than 1, e.g., hemihydrates ($R.0.5 H_2O$)), and polyhydrates (x is a number greater than 1, e.g., dihydrates ($R.2 H_2O$) and hexahydrates ($R.6 H_2O$)).

IRF8 gene: As used herein, the term "IRF8 gene" refers to a genomic DNA sequence that encodes an interferon consensus sequence-binding protein or splice variant thereof and specifically excludes gene fusions that comprise all or a portion of the IRF8 gene. In some embodiments, the IRF8 gene is located at chr16:85862582-85990086 in genome build hg19.

"Improve," "increase" or "reduce": As used herein or grammatical equivalents thereof, indicate values that are relative to a reference measurement, such as a measurement in the same individual prior to initiation of a treatment described herein, or a measurement in a control individual (or multiple control individuals) in the absence of the treatment described herein. In some embodiments, a "control individual" is an individual afflicted with the same form of disease or injury as an individual being treated.

Messenger RNA transcript: As used herein, the term "messenger RNA transcript" or mRNA refers to the RNA transcription product from the DNA sequence that include one or more of the gene coding region.

Ordinal rank: As used herein, the term "ordinal rank" of a specified value means the rank order of that value as compared to a set of other values. For example, an ordinal rank of 100 in terms of the strength of a super enhancer associated with a RARA gene in a test cell as compared to other super enhancers in the test cell means that 99 other super enhancers in the test cell had greater strength than the super enhancer associated with a RARA gene.

Patient: As used herein, the term "patient" or "subject" refers to any organism to which a provided composition is or may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. A human includes pre and post-natal forms. In some embodiments, a patient is suffering from or susceptible to one or more disorders or conditions. In some embodiments, a patient displays one or more symptoms of a disorder or condition. In some embodiments, a patient has been diagnosed with one or more disorders or conditions Pharmaceutically acceptable salt: As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, MALAT1e, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p toluenesulfonate, undecanoate, valerate salts, and the like. Salts derived from appropriate bases include alkali metal, alkaline earth metal, ammonium and $N^+(C_{1-4}$ alkyl$)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

Population: As used herein, the term "population" or "population of samples" means a sufficient number (e.g., at least 30, 40, 50 or more) of different samples that reasonably reflects the distribution of the value being measured in a larger group. Each sample in a population of samples may be a cell line, a biological sample obtained from a living being (e.g., a biopsy or bodily fluid sample), or a sample obtained from a xenograft (e.g., a tumor grown in a mouse by implanting a cell line or a patient sample), wherein each sample is from a living being suffering from or from a cell line or xenograft representing, the same disease, condition or disorder.

Prevalence cutoff: As used herein, the term "prevalence cutoff" for a specified value (e.g., the strength of a super enhancer associated with an IRF8 gene) means the prevalence rank that defines the dividing line between two subsets of a population (e.g., responders and non-responders). Thus, a prevalence rank that is equal to or higher (e.g., a lower percentage value) than the prevalence cutoff defines one subset of the population; and a prevalence rank that is lower (e.g., a higher percentage value) than the prevalence cutoff defines the other subset of the population.

Prevalence rank: As used herein, the term "prevalence rank" for a specified value (e.g., the strength of a super enhancer associated with an IRF8 gene) means the percentage of a population that are equal to or greater than that specific value. For example a 35% prevalence rank for the strength of a super enhancer associated with an IRF8 gene in a test cell means that 35% of the population have an IRF8 gene enhancer with a strength equal to or greater than the test cell.

Prognostic and predictive information: As used herein, the terms "prognostic information" and "predictive information" are used to refer to any information that may be used to indicate any aspect of the course of a disease or condition either in the absence or presence of treatment. Such information may include, but is not limited to, the average life expectancy of a patient, the likelihood that a patient will survive for a given amount of time (e.g., 6 months, 1 year, 5 years, etc.), the likelihood that a patient will be cured of a disease, the likelihood that a patient's disease will respond to a particular therapy (wherein response may be defined in any of a variety of ways). Prognostic and predictive information are included within the broad category of diagnostic information.

Rank ordering: As used herein, the term "rank ordering" means the ordering of values from highest to lowest or from lowest to highest.

RARA gene: As used herein, the term "RARA gene" refers to a genomic DNA sequence that encodes a functional retinoic acid receptor-α and specifically excludes gene fusions that comprise all or a portion of the RARA gene. In some embodiments, the RARA gene is located at chr17: 38458152-38516681 in genome build hg19.

Reference: as used herein describes a standard or control relative to which a comparison is performed. For example, in some embodiments, an agent, animal, individual, population, sample, sequence, or value of interest is compared with a reference or control agent, animal, individual, population, sample, sequence or value. In some embodiments, a reference or control is tested and/or determined substantially simultaneously with the testing or determination of interest. In some embodiments, a reference or control is a historical reference or control, optionally embodied in a tangible medium. Typically, as would be understood by those skilled in the art, a reference or control is determined or characterized under comparable conditions or circumstances to those under assessment. Those skilled in the art will appreciate when sufficient similarities are present to justify reliance on and/or comparison to a particular possible reference or control.

Response: As used herein, a response to treatment may refer to any beneficial alteration in a subject's condition that occurs as a result of or correlates with treatment. Such alteration may include stabilization of the condition (e.g., prevention of deterioration that would have taken place in the absence of the treatment), amelioration of, delay of onset of, and/or reduction in frequency of one or more symptoms of the condition, and/or improvement in the prospects for cure of the condition, etc. In some instances, a response may be a subject's response; in some instances a response may be a tumor's response.

Solvate: As used herein, the term "solvate" refers to forms of the compound that are associated with a solvent, usually by a solvolysis reaction. This physical association may include hydrogen bonding. Conventional solvents include water, methanol, ethanol, acetic acid, DMSO, THF, diethyl ether, and the like. The compounds described herein, such as of Formula (I) may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolable solvates. Representative solvates include hydrates, ethanolates, and methanolates.

Strength: As used herein, the term "strength" when referring to a portion of an enhancer or a super enhancer, as used herein means the area under the curve of the number of H3K27Ac or other genomic marker reads plotted against the length of the genomic DNA segment analyzed. Thus, "strength" is an integration of the signal resulting from measuring the mark at a given base pair over the span of the base pairs defining the region being chosen to measure.

Subject: As used herein, a "subject" to which administration is contemplated is a human (e.g., a male or female of any age group, e.g., a pediatric subject (e.g., infant, child, adolescent) or adult subject (e.g., young adult, middle-aged adult, or senior adult)).

Super Enhancer: As used herein, the term "super enhancer" refers to a subset of enhancers that contain a disproportionate share of histone marks and/or transcriptional proteins relative to other enhancers in a particular cell. Because of this, a gene regulated by a super enhancer is predicted to be of high importance to the function of that cell. Super enhancers are typically determined by rank ordering all of the enhancers in a cell based on strength and determining using available software such as ROSE (https://bitbucket.org/young_computation/rose), the subset of enhancers that have significantly higher strength than the median enhancer in the cell (see, e.g., U.S. Pat. No. 9,181,580, which is herein incorporated by reference.

Threshold: As used herein, the terms "threshold" and "threshold level" mean a level that defines the dividing line between two subsets of a population (e.g., responders and non-responders). A threshold or threshold level may be a prevalence cutoff or a cutoff value.

Treatment: As used herein, the terms "treatment," "treat," and "treating" refer to reversing, alleviating, delaying the onset of, or inhibiting the progress of a "pathological condition" (e.g., a disease, disorder, or condition, or one or more signs or symptoms thereof) described herein. In some embodiments, "treatment," "treat," and "treating" require that signs or symptoms of the disease disorder or condition have developed or have been observed. In other embodiments, treatment may be administered in the absence of signs or symptoms of the disease or condition (e.g., in light of a history of symptoms and/or in light of genetic or other susceptibility factors). Treatment may also be continued after symptoms have resolved, for example, to delay or prevent recurrence.

As used herein, the terms "condition," "disease," and "disorder" are used interchangeably.

DETAILED DESCRIPTION OF CERTAIN EMBODIMENTS OF THE INVENTION

RARA and IRF8

The retinoic acid receptor subtype alpha (RARA) is a nuclear hormone receptor that acts as a transcriptional repressor when unbound or bound by an antagonist, and as a gene activator in the agonist-bound state. The natural ligand of RARA is retinoic acid, also known as all-trans retinoic acid (ATRA), which is produced from vitamin A.

Super-enhancers (SEs) are large, highly-active chromatin regions that regulate key cell identity genes, including oncogenes in malignant cells. Using a gene control platform, we identified SEs genome-wide in 60 primary AML patient samples to enable the discovery of novel tumor vulnerabilities. One of the SEs that exhibited a differential presence among patient samples was associated with the RARA gene encoding RARA.

Studies have demonstrated good correlations between tamibarotene responsiveness and either or both of RARA super enhancer strength and mRNA levels. However, for each of these potential RARA biomarkers, there was a middle range within which tamibarotene responsiveness was mixed. The present disclosure provides insights and technologies that help resolve such equivocal responsiveness results, and provides various compositions and methods useful in, among other things, characterizing, identifying, selecting, or stratifying patients based on likely responsiveness to tamibarotene therapy. For example, the present disclosure provides technologies that embody, define and/or utilize one or more IRF8 biomarkers (e.g., presence, level, form, and/or activity of one or more IRF8 gene components or products, including for example IRF8 super enhancer strength, ordinal rank, prevalence rank, or IRF8 mRNA levels), and demonstrates their usefulness in cancer therapy.

Using various AML cell lines and patient samples previously analyzed for strength and ordinal of RARA enhancers, RARA mRNA levels and responsiveness to tamibarotene, we looked for additional biomarkers that would correlate with responsiveness to tamibarotene. Interferon response factor 8 (IRF8) mRNA levels were found to be upregulated in similar patient populations as RARA. IRF8 is an interferon responsive transcription factor known to be critical to hematopoiesis and whose signaling loss causes aberrant expansion of immature myeloid cells. In AML, IRF8 overexpression is observed and may correlate with poor clinical outcome. Despite this upregulation, IRF8 signaling is actually impaired by repressive transcriptional cofactors and potentially RARA when it is in a SE-driven repressive state. Furthermore, interferon-α itself, the upstream signaling ligand for IRFs, exhibits pro-differentiation effects in AML, and signaling cross-talk with the RARA pathway.

The present disclosure describes genome-wide expression and enhancer level analysis of a panel of AML patient tumor samples and cell lines to examine the correlation of IRF8 gene enhancer strength, IRF8 mRNA levels, and sensitivity to tamibarotene. The panel of AML cell lines was previously tested for and shown to have a correlation between its sensitivity to the anti-proliferative effects of the RARA agonist tamibarotene and both RARA enhancer strength and RARA mRNA levels. In this application we demonstrate that IRF8 mRNA levels are also elevated in AML cell lines and AML patient samples that have elevated RARA mRNA levels and that there is a correlation between IRF8 mRNA levels and responsiveness to a RARA agonist, such as tamibarotene. We also demonstrate that there is a correlation between IRF8 enhancer strength (e.g., the presence of super-enhancer associated with IRF8), IRF8 mRNA levels, RARA mRNA levels and responsiveness to tamibarotene. Thus, IRF8 enhancer strength or IRF8 mRNA levels may be used alone, or in conjunction with RARA enhancer strength or RARA mRNA levels to identify patients that will be responsive to treatment with a RARA agonist, such as tamibarotene.

IRF8 and RARA Super-Enhancer Identification and Determination of Threshold Levels The identification of an enhancer or super enhancer may be achieved by various methods known in the art, for example as described in Cell 2013, 155, 934-947 and PCT/US2013/066957, both of which are incorporated herein by reference. In some embodiments, the identification of a super enhancer is achieved by obtaining cellular material and DNA from a cancer sample in a patient (e.g., from a biopsy). The important metrics for enhancer measurement occur in two dimensions—the length of the DNA over which genomic markers (e.g., H3K27Ac) are contiguously detected—and the compiled incidence of genomic marker at each base pair along that span of DNA constituting the magnitude. The measurement of the area under the curve ("AUC") resulting from integration of length and magnitude analysis determines the strength of the enhancer. It is the strength of the IRF8 or RARA super enhancer relative to a control that is used in one aspect of the present invention to determine whether or not a subject will be responsive to a RARA agonist (e.g., tamibarotene). It will be readily apparent to those of skill in the art, in view of the instant specification, that if the length of DNA over which the genomic markers is detected is the same for both IRF8 or RARA and the control, then the ratio of the magnitude of the IRF8 or RARA super enhancer relative to the control will be equivalent to the strength and may also be used to determine whether or not a subject will be responsive to a RARA agonist. In some embodiments, the strength of the IRF8 or RARA enhancer in a cell is normalized before comparing to other samples. Normalization is achieved by comparison to a region in the same cell known to comprise a ubiquitous super-enhancer or enhancer that is present at similar levels in all cells. One example of such a ubiquitous super-enhancer region is the MALAT1 super-enhancer locus (chr11:65263724-65266724) (genome build hg19).

It has been determined through H3K27Ac ChIP-seq methods that there is a super-enhancer locus associated with the RARA gene at chr17:38458152-38516681 (genome build hg19) and that there is a super-enhancer locus associated with the IRF8 gene at chr16:85862582-85990086 (genome build hg19).

ChIP-sequencing, also known as ChIP-seq, is used to analyze protein interactions with DNA. ChIP-seq combines chromatin immunoprecipitation (ChIP) with massively parallel DNA sequencing to identify the binding sites of DNA-associated proteins. It can be used to map global binding sites precisely for any protein of interest. Previously, ChIP-on-chip was the most common technique utilized to study these protein—DNA relations. Successful ChIP-seq is dependent on many factors including sonication strength and method, buffer compositions, antibody quality, and cell number.; see, e.g., T. Furey, Nature Reviews Genetics 13, 840-852 (December 2012); M. L. Metzker, Nature Reviews Genetics 11, 31-46 (January 2010); and P. J Park, Nature Reviews Genetics 10, 669-680 (October 2009)). Genomic markers other that H3K27Ac that can be used to identify super enhancers using ChIP-seq include, P300, CBP, BRD2, BRD3, BRD4, components of the mediator complex (J Loven, et al., Cell, 153(2):320-334, 2013), histone 3 lysine 4 monomethylated (H3K4me1), or other tissue specific enhancer tied transcription factors (E Smith & A Shilatifard, Nat Struct Mol Biol, 21(3):210-219, 2014) (S Pott & Jason Lieb, Nature Genetics, 47(1):8-12, 2015).

In some embodiments, H3K27Ac or other marker ChIP-seq data super-enhancer maps of the entire genome of a cell line or a patient sample already exist. In some embodiments, one would simply determine whether the strength, or ordinal rank of the enhancer or super-enhancer in such maps at the chr17:38458152-38516681 (genome build hg19) locus was equal to or above the pre-determined threshold level. In some embodiments, one would simply determine whether the strength, or ordinal rank of the enhancer or super-enhancer in such maps at the chr16:85862582-85990086 (genome build hg19) locus was equal to or above the pre-determined threshold level.

It should be understood that the specific chromosomal location of IRF8, RARA, and MALAT1 may differ for different genome builds and/or for different cell types. However, one of skill in the art, in view of the instant specification, can determine such different locations by locating in such other genome builds specific sequences corresponding to the RARA and/or MALAT1 loci in genome build hg 19.

Other methods for identifying super enhancers include chromatin immunoprecipitation (J E Delmore, et al., Cell, 146(6)904-917, 2011) and chip array (ChIP-chip), and chromatin immunoprecipitation followed by qPCR (ChIP-qPCR) using the same immunoprecipitated genomic markers and oligonucleotide sequences that hybridize to the chr17:38458152-38516681 (genome build hg19) RARA locus or chr16:85862582-85990086 (genome build hg19) IRF8 locus. In the case of ChIP-chip, the signal is typically detected by intensity fluorescence resulting from hybridization of a probe and input assay sample as with other array based technologies. For ChIP-qPCR, a dye that becomes fluorescent only after intercalating the double stranded DNA generated in the PCR reaction is used to measure amplification of the template.

In some embodiments, determination of whether a cell has an IRF8 super enhancer strength equal to or above a requisite threshold level is achieved by comparing IRF8 enhancer strength in a test cell to the corresponding IRF8 strength in a population of cell samples, wherein each of the cell samples is obtained from a different source (e.g., a different subject, a different cell line, a different xenograft) reflecting the same disease to be treated. In some aspects of these embodiments, only primary tumor cell samples from subjects are used to determine the threshold level. In some aspects of these embodiments, at least some of the samples in the population will have been tested for responsiveness to a specific RARA agonist in order to establish: a) the lowest IRF8 enhancer strength of a sample in the population that responds to that specific RARA agonist ("lowest responder"); and, optionally, b) the highest IRF8 enhancer strength of a sample in the population that does not respond to that specific RARA agonist ("highest non-responder"). In these embodiments, a cutoff of IRF8 enhancer strength above which a test cell would be considered responsive to that specific RARA agonist is set: i) equal to or up to 5% above the IRF8 enhancer strength in the lowest responder in the population; or ii) equal to or up to 5% above the IRF8 enhancer strength in the highest non-responder in the population; or iii) a value in between the IRF8 enhancer strength of the lowest responder and the highest non-responder in the population.

It should be understood that in the above embodiments that not all of the samples in a population necessarily are to be tested for responsiveness to a RARA agonist, but all samples are measured for IRF8 enhancer strength and/or IRF8 mRNA levels. In some embodiments, the samples are rank ordered based on IRF8 enhancer strength. The choice of which of the three methods set forth above to use to establish the cutoff will depend upon the difference in IRF8 enhancer strength between the lowest responder and the highest non-responder in the population and whether the goal is to minimize the number of false positives or to minimize the chance of missing a potentially responsive sample or subject. When the difference between the lowest responder and highest non-responder is large (e.g., when there are many samples not tested for responsiveness that fall between the lowest responder and the highest non-responder in a rank ordering of IRF8 enhancer strength), the cutoff is typically set equal to or up to 5% above the IRF8 enhancer strength in the lowest responder in the population. This cutoff maximizes the number of potential responders. When this difference is small (e.g., when there are few or no samples untested for responsiveness that fall between the lowest responder and the highest non-responder in a rank ordering of IRF8 enhancer strength), the cutoff is typically set to a value in between the IRF8 enhancer strength of the lowest responder and the highest non-responder. This cutoff minimizes the number of false positives. When the highest non-responder has an IRF8 enhancer strength that is greater than the lowest responder, the cutoff is typically set to a value equal to or up to 5% above the IRF8 enhancer strength in the highest non-responder in the population. This method also minimizes the number of false positives.

In some embodiments, determination of whether a cell has an IRF8 super enhancer equal to or above a requisite threshold level is achieved by comparing the ordinal of IRF8 enhancer strength in a test cell to the ordinal of IRF8 enhancer strength in a population of cell samples, wherein each of the cell samples is obtained from a different source (e.g., a different subject, a different cell line, a different xenograft). In these embodiments, at least some of the samples in the population will have been tested for responsiveness to a specific RARA agonist in order to establish: a) the lowest IRF8 enhancer strength ordinal of a sample in the population that responds to that specific RARA agonist ("lowest ordinal responder"); and, optionally, b) the highest IRF8 enhancer strength ordinal of a sample in the population that does not respond to that specific RARA agonist ("highest ordinal non-responder"). In these embodiments, a cutoff of IRF8 enhancer strength ordinal above which a test cell would be considered responsive to that specific RARA agonist is set: i) equal to or up to 5% above the IRF8 enhancer strength ordinal in the lowest ordinal responder in the population; or ii) equal to or up to 5% above the IRF8 enhancer strength ordinal in the highest ordinal non-responder in the population; or iii) a value in between the IRF8 enhancer strength ordinal of the lowest ordinal responder and the highest ordinal non-responder in the population.

It should be understood in the above embodiments, that typically not all of the samples in a population need to be tested for responsiveness to a RARA agonist, but all samples are measured for IRF8 enhancer strength and the ordinal of IRF8 enhancer strength compared to other enhancers in the same sample is established. The ordinal is typically obtained by measuring the strength of all other enhancers in the cell and determining what rank (e.g., the ordinal) in terms of strength the IRF8 enhancer has as compared to the other enhancers.

In some embodiments, the samples are rank ordered based on the ordinal of IRF8 enhancer strength. The choice of which of the three methods set forth above to use in order to establish the cutoff will depend upon the difference in ordinal of IRF8 enhancer strength between the lowest ordinal responder and the highest ordinal non-responder in the population and whether the cutoff is designed to minimize false positives or maximize the number of responders. When this difference is large (e.g., when there are many samples not tested for responsiveness that fall between the lowest ordinal responder and the highest ordinal non-responder in a rank ordering of ordinals of IRF8 enhancer strength), the cutoff is typically set equal to or up to 5% above the ordinal of IRF8 enhancer strength in the lowest ordinal responder in the population. When this difference is small (e.g., when there are few or no samples untested for responsiveness that fall between the lowest ordinal responder and the highest ordinal non-responder in a rank ordering of ordinal of IRF8 enhancer strength), the cutoff is typically set to a value in between the ordinal of IRF8 enhancer strength of the lowest ordinal responder and the highest ordinal non-responder. When the highest ordinal non-responder has an ordinal of IRF8 enhancer strength that is greater than that of the lowest responder, the cutoff is typically set to a value equal to or up to 5% above the ordinal of IRF8 enhancer strength in the highest ordinal non-responder in the population.

In some embodiments where a test cell or sample is compared to a population, the cutoff value(s) obtained for the population (e.g., IRF8 enhancer strength or IRF8 enhancer ordinal) is converted to a prevalence rank and the cutoff is expressed as a percent of the population having the cutoff value or higher, e.g., a prevalence cutoff. Without being bound by theory, applicants believe that the prevalence rank of a test sample will be similar regardless of the methodology used to determine IRF8 enhancer strength. Thus, a prevalence cutoff determined for one parameter (e.g., IRF8 enhancer strength ordinal) is portable and can be applied to another parameter (e.g., IRF8 mRNA level) to determine the cutoff value for that other parameter. This allows the determination of a cutoff value for any parameter without having to experimentally determine the correlation between levels of such parameter and responsiveness to a RARA agonist. All that needs to be determined is what level of such other parameter corresponds to the prior determined prevalence cutoff in a population.

In some embodiments, the methods discussed above can be employed to simply determine if a diseased cell from a subject has a super enhancer associated with an IRF8 gene. In these embodiments, the presence of an IRF8-associated super enhancer indicates that the subject will respond to a RARA agonist. In one aspect of these embodiments, the cell is determined to have a super enhancer associated with an IRF8 gene when the IRF8-associated enhancer has a strength that is equal to or above the enhancer associated with MALAT-1. In alternate aspects of these embodiments, the cell is determined to have a super enhancer associated with an IRF8 gene when the IRF8-associated enhancer has a strength that is at least 10-fold greater than the median strength of all of the enhancers in the cell. In other alternate aspects of these embodiments, the cell is determined to have a super enhancer associated with an IRF8 gene when the IRF8-associated enhancer has a strength that is above the point where the slope of the tangent is 1 in a rank-ordered graph of strength of each of the enhancers in the cell.

In some embodiments, the methods discussed above can be employed to additionally determine if a diseased cell from a subject expresses a super enhancer associated with a RARA gene that has a strength, ordinal rank, or prevalence rank that is equal to or above a pre-determined threshold level. In some aspects of these embodiments, a determination that either: a) the diseased cell has a super enhancer associated with a IRF8 gene (or that such super enhancer has a strength or ordinal rank that is equal to or above a pre-determined threshold level; or b) the diseased cell has a super enhancer associated with a RARA gene that has a strength or ordinal rank that is equal to or above a pre-determined threshold level indicates that the subject will respond to a RARA agonist. In other aspects of these embodiments, a determination that: a) the diseased cell has a super enhancer associated with a IRF8 gene (or that such super enhancer has a strength or ordinal rank that is equal to or above a pre-determined threshold level; and b) the diseased cell has a super enhancer associated with a RARA gene that has a strength or ordinal rank that is equal to or above a pre-determined threshold level indicates that the subject will respond to a RARA agonist.

IRF8 mRNA Level Determination

Figure 10:
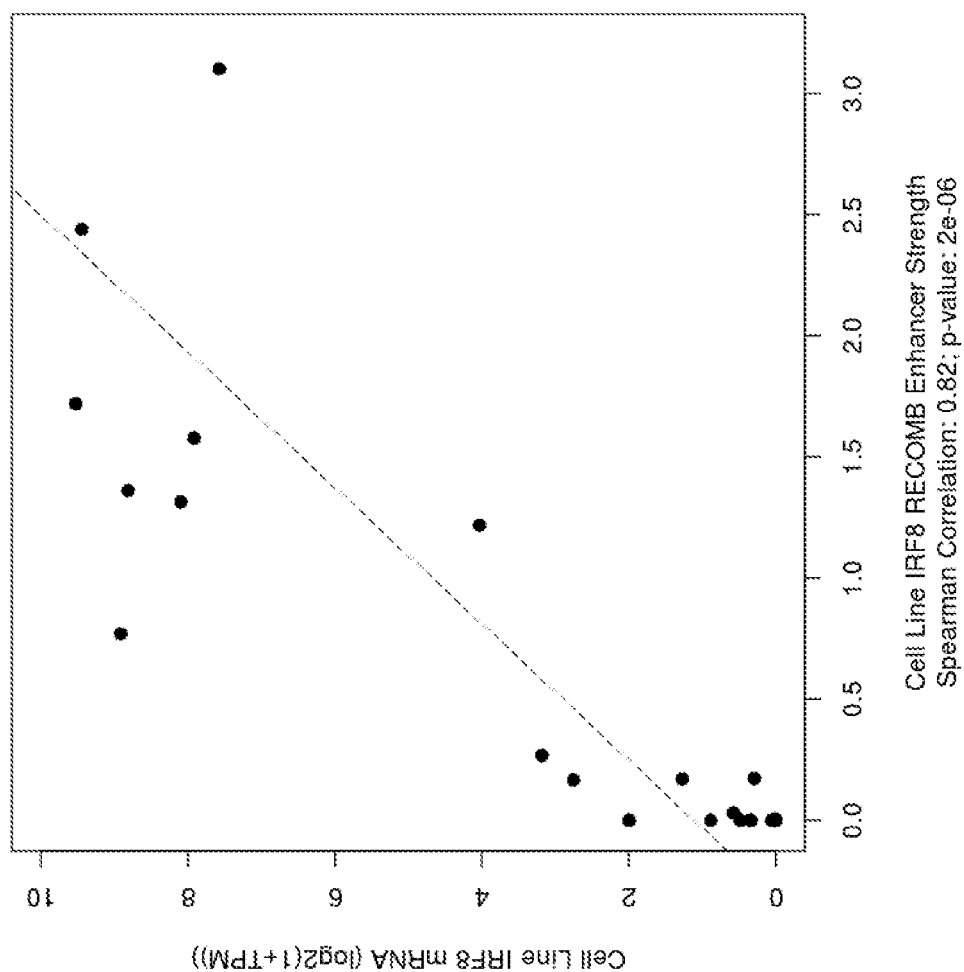
FIG. 10 shows correlation of IRF8 mRNA levels with IRF8 enhancer strength in AML cell lines. Plot of IRF8 mRNA transcript abundance by quantile normalized RNA-seq TPM (Y-axis) as a function of IRF8 RECOMB enhancer strength (X-axis) in all non-APL AML cell lines for which both RNA-seq and ChIP-seq data was available. The Spearman Rho correlation estimate is ~0.82, with a p-value ~$2 \times 10^{-6}$.

In some embodiments, IFR8 mRNA levels may be used instead of super-enhancer strength or ordinal rank to determine sensitivity to a RARA agonist. IRF8 mRNA may be quantified and correlates very well with super-enhancer strength at that locus (FIG. 10). We have determined that mRNA transcripts encoding IRF8 correlate with sensitivity to RARA agonists (FIG. 8), and thus in some embodiments, IRF8 mRNA levels can be used to identify cells that will respond to RARA agonists.

In some embodiments, sequences of one or more biomarkers (e.g., epigenetic markers such a transcript level) are assessed. In some embodiments, DNA sequencing may be used to determine the sequence of individual genes, larger genetic regions (e.g. clusters of genes or operons), full chromosomes or entire genomes. In some embodiments, RNA sequencing may be used. One of skill in the art would understand various methods available to determine sequences of individual genes, larger genetic regions (e.g. clusters of genes or operons), full chromosomes or entire genomes. In some embodiments, next-generation sequencing may be used. In some embodiments, next-generation sequencing of full genomes may be used. In some embodiments, sequencing may be utilized to quantify level of transcript.

In some embodiments, IRF8 mRNA levels in a subject (e.g., in a tumor sample, in a cancer cell sample, in a blood sample, etc.) are compared, using the same assay, to the IRF8 mRNA levels in a population of subjects having the same disease or condition to identify RARA agonist responders. In these embodiments, at least some of the samples in the population will have been tested for responsiveness to a specific RARA agonist in order to establish: a) the lowest IRF8 mRNA level of a sample in the population that responds to that specific RARA agonist ("lowest mRNA responder"); and, optionally, b) the highest IRF8 mRNA level of a sample in the population that does not respond to that specific RARA agonist ("highest mRNA non-responder"). In these embodiments, a cutoff of IRF8 mRNA level above which a test cell would be considered responsive to that specific RARA agonist is set: i) equal to or up to 5% above the IRF8 mRNA level in the lowest mRNA responder in the population; or ii) equal to or up to 5% above the IRF8 mRNA level in the highest mRNA non-responder in the population; or iii) a value in between the IRF8 mRNA level of the lowest mRNA responder and the highest mRNA non-responder in the population.

In some embodiments not all of the samples in a population need to be tested for responsiveness to a RARA agonist, but all samples are measured for IRF8 mRNA levels. In some embodiments, the samples are rank ordered based on IRF8 mRNA levels. The choice of which of the three methods set forth above to use to establish the cutoff will depend upon the difference in IRF8 mRNA levels between the lowest mRNA responder and the highest mRNA non-responder in the population and whether the cutoff is designed to minimize false positives or maximize the potential number of responders. When this difference is large (e.g., when there are many samples not tested for responsiveness that fall between the lowest mRNA responder and the highest mRNA non-responder in a rank ordering of IRF8 mRNA levels), the cutoff is typically set equal to or up to 5% above the IRF8 mRNA level in the lowest mRNA responder in the population. When this difference is small (e.g., when there are few or no samples untested for responsiveness that fall between the lowest mRNA responder and the highest mRNA non-responder in a rank ordering of IRF8 mRNA levels), the cutoff is typically set to a value in between the IRF8 mRNA levels of the lowest mRNA responder and the highest mRNA non-responder. When the highest mRNA non-responder has an IRF8 mRNA level that is greater than the lowest mRNA responder, the cutoff is typically set to a value equal to or up to 5% above the IRF8 mRNA levels in the highest mRNA non-responder in the population.

In some embodiments, the population is rank ordered based on IRF8 mRNA level. In these embodiments, the IRF8 mRNA level in each sample is measured and compared to the mRNA levels of all other mRNAs in the cell to obtain an ordinal ranking of the IRF8 mRNA level. A cutoff based on IRF8 mRNA ordinal ranking is then determined based on samples in the population tested for responsiveness to a RARA agonist in the same manner as described previously for determining an IRF8 super enhancer strength ordinal cutoff. The determined IRF8 mRNA ordinal cutoff is then used either directly or to determine a prevalence cutoff, either of which is then used to stratify additional samples for potential responsiveness to a RARA agonist.

In some embodiments, the cutoff for IRF8 mRNA levels is determined using the prevalence cutoff established based on IRF8 enhancer strength or IRF8 enhancer strength ordinal, as described above. In some aspects of these embodiments, a population is measured for mRNA levels and the prior determined prevalence cutoff is applied to that population to determine an mRNA cutoff level. In some aspects of these embodiments a rank-order standard curve of IRF8 mRNA levels in a population is created, and the predetermined prevalence cutoff is applied to that standard curve to determine the IRF8 mRNA cutoff level.

In some aspects of embodiments where a test cell or sample is compared to a population, the cutoff mRNA level value(s) obtained for the population is converted to a prevalence rank and the mRNA level cutoff is expressed as a percent of the population having the cutoff value or higher, e.g., a prevalence cutoff.

Without being bound by theory, applicants believe that the prevalence rank of a test sample and the prevalence cutoff in a population will be similar regardless of the methodology used to determine IRF8 mRNA levels.

In some aspects of these embodiments, a subject is identified as a RARA agonist responder if its IRF8 mRNA level corresponds to a prevalence rank in a population of about 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 43%, 42%, 51%, 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, or 20% as determined by IRF8 mRNA levels in the population. In some embodiments, the cutoff value is established based on the prevalence cutoff established for IRF8 enhancer strength. In some embodiments, the cutoff value is established based on the prevalence cutoff established for IRF8 enhancer strength ordinal. In some embodiments, the cutoff value is established based on IRF8 mRNA levels. In some embodiments, a cutoff value for AML, non-APL AML, or MDS patients is established based on the prevalence value determined for IRF8 enhancer strength ordinal, and that prevalence value is used to determine the cutoff value for IRF8 mRNA levels. In some embodiments, the cutoff value for AML, non-APL AML or MDS patients is determined using a prevalence cutoff of between about 20-45% (e.g., between about 20-25%, 25-30%, 25-35%, 25-40%, 20-30%, 20-35%, 20-40%, 20-45%, 21-34%, 22-34%, 25-34%, 21-25%, 22-25%, 23-25%, 24-25%, or 21-22%). In some embodiments, the cutoff value for AML, non-APL AML or MDS patients is determined using a prevalence value of 34%. In some embodiments, the cutoff value for AML, non-APL AML or MDS patients is determined using a prevalence value of 25%. In some embodiments, the cutoff value for AML, non-APL AML or MDS patients is determined using a prevalence value of 22%. In some embodiments, the cutoff value for AML, non-APL AML or MDS patients is determined using a prevalence value of 21%.

In still other embodiments, a population may be divided into three groups—responders, partial responders and non-responders and two cutoff values or prevalence cutoffs are set. The partial responder group may include responders and non-responders, as well as those population members whose response to a RARA agonist was not as high as the responder group. In these embodiments, two cutoff values or prevalence cutoffs are determined. This type of stratification may be particularly useful when in a population the highest IRF8 mRNA non-responder has an IRF8 mRNA levels that is greater than the lowest RARA mRNA responder. In this scenario the cutoff level or prevalence cutoff between responders and partial responders is set equal to or up to 5% above the IRF8 mRNA level of the highest IRF8 mRNA non-responder; and the cutoff level or prevalence cutoff between partial responders and non-responders is set equal to or up to 5% below the IRF8 mRNA level of the lowest IRF8 mRNA responder. The determination of whether partial responders should be administered a RARA agonist will depend upon the judgment of the treating physician and/or approval by a regulatory agency.

Methods of quantifying specific RNA sequences in a cell or biological sample are known in the art and include, but are not limited to, fluorescent hybridization such as utilized in services and products provided by NanoString Technologies, array based technology (Affymetrix), reverse transcriptase qPCR as with SYBR® Green (Life Technologies) or TaqMan® technology (Life Technologies), RNA sequencing (e.g., RNA-seq), RNA hybridization and signal amplification as utilized with RNAscope® (Advanced Cell Diagnostics), or northern blot.

In some aspects of these embodiments, the level of RNA transcript (either mRNA or another RARA or IRF8 transcript) in both the test cell and the control cell or all members of the population are normalized before comparison. Normalization involves adjusting the determined level of an IRF8 or RARA RNA transcript by comparison to either another RNA transcript that is native to and present at equivalent levels in both of the cells (e.g., GADPH mRNA, 18S RNA), or to a fixed level of exogenous RNA that is "spiked" into samples of each of the cells prior to super-enhancer strength determination (J Lovén et al., Cell, 151 (3):476-82 (2012); J Kanno et al., BMC Genomics 7:64 (2006); J Van de Peppel et al., EMBO Rep 4:387-93 (2003)).

Cancers and Other Diseases

The methods of the present disclosure are useful to treat any cancer that is characterized by the association of a super enhancer with IRF8 or an IRF8 mRNA level that is equal to or above a threshold level in such cancer. Super enhancer-associated IRF8 genes may be more prevalent in certain types of cancers than others. In some embodiments, super enhancer-associated IRF8 genes may be more prevalent in non-APL AML and in MDS than other cancers or pre-cancerous conditions.

In some embodiments, the disease to be treated in the methods of the invention is cancer. In some embodiments, the disease to be treated is selected from non-APL AML and MDS. In some embodiments, the disease to be treated is non-APL AML and MDS that is not characterized by a chromosomal translocation involving an IRF8 gene.

In some embodiments, the subject to be treated with a RARA agonist (e.g., tamibarotene) is suffering from relapsed or refractory non-APL AML. A subject is classified as having relapsed or refractory non-APL AML if they: a) do not demonstrate a partial response after a first cycle of induction chemotherapy; or b) do not demonstrate a complete response after a second cycle of induction chemotherapy; or c) relapse after conventional chemotherapy; or d) relapse after undergoing a single stem cell transplantation.

In some embodiments, the subject to be treated with a RARA agonist (e.g., tamibarotene) is suffering from refractory MDS. A subject is classified as having refractory MDS if they: a) are categorized as having high risk or intermediate-2 MDS (as determined using the International Prognostic Staging System ("IPPS")) and have failed to achieve any hematologic improvement (as measured by IWG 2006 criteria) after at least 4 cycles of induction therapy with hypomethylating agents (e.g., azacitidine, decitabine), or has relapsed after any duration of complete or partial response; orb) are categorized as IPSS intermediate-1 or low-risk MDS and are either transfusion dependent or have failed treatment with erythropoiesis stimulating agents (ESA).

In other embodiments, the subject to be treated with a RARA agonist (e.g., tamibarotene) is an elderly unfit subject. The term "elderly unfit" as used herein means the subject is a human at least 60 years of age and who is determined by a physician to not be a candidate for standard induction therapy.

RARA Agonists

The choice of RARA agonist with which to treat a patient identified as having a super enhancer level may be made from any RARA agonist known in the art. It is preferable that a RARA agonist utilized in the methods of the invention be specific for RARA and have significantly less (at least 10× less, at least 100× less, at least 1,000× less, at least 10,000× less, at least 100,000× less) agonistic activity against other forms of RaR, e.g., RaR-ß and RaR-γ.

In some embodiments, a RARA agonist is selected from a compound disclosed in or any compound falling within the genera set forth in any one of the following United States patents: U.S. Pat. No. 4,703,110, U.S. Pat. No. 5,081,271, U.S. Pat. No. 5,089,509, U.S. Pat. No. 5,455,265, U.S. Pat. No. 5,759,785, U.S. Pat. No. 5,856,490, U.S. Pat. No. 5,965,606, U.S. Pat. No. 6,063,797, U.S. Pat. No. 6,071,924, U.S. Pat. No. 6,075,032, U.S. Pat. No. 6,187,950, U.S. Pat. No. 6,355,669, U.S. Pat. No. 6,358,995, and U.S. Pat. No. 6,387,950, each of which is incorporated by reference.

In some embodiments, a RARA agonist is selected from any of the following known RARA agonists set forth in Table 1, or a pharmaceutically acceptable salt thereof, or a solvate or hydrate of the foregoing:

TABLE 1

Exemplary RARA Agonists useful in the invention.

| Structure | Code Name(s) |
|---|---|
| 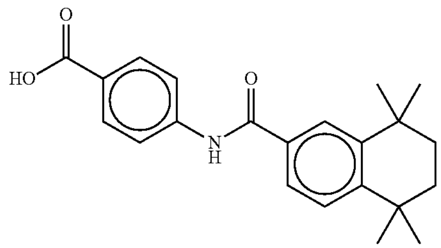 | Am-580; CD-336; Ro-40-6055 |
| 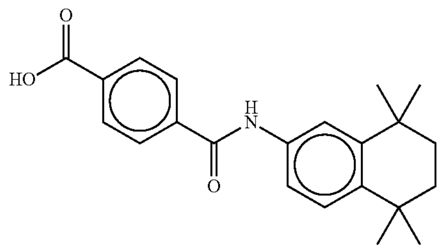 | AM-80; INNO-507; NSC-608000; OMS-0728; TM-411; TOS-80; TOS-80T; Z-208; tamibarotene |
| 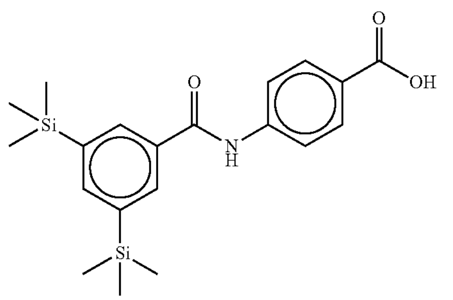 | Am-555S; TAC-101; amsilarotene |
| 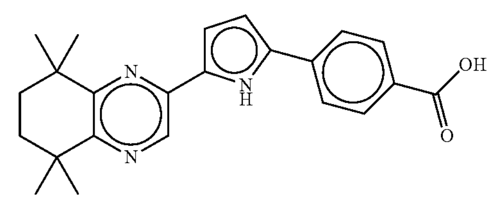 | ER-34617 |
| 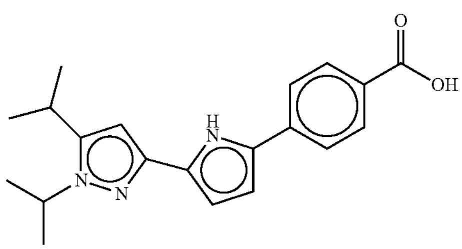 | ER-38930 |
| | |

TABLE 1-continued

Exemplary RARA Agonists useful in the invention.

| Structure | Code Name(s) |
|---|---|
| | |
| | |
| | |
| | |
| 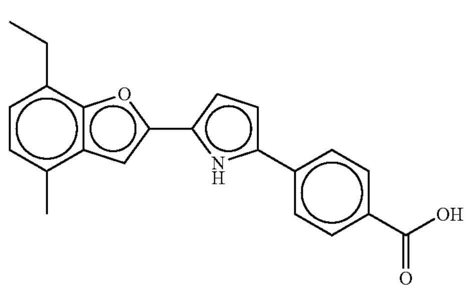 | ER-65250 |

TABLE 1-continued

Exemplary RARA Agonists useful in the invention.

| Structure | Code Name(s) |
|---|---|
| 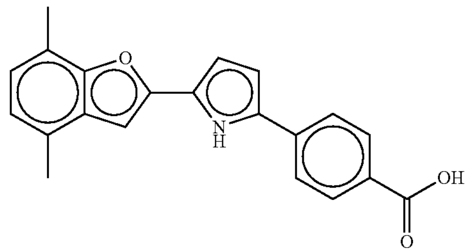 | ER-38925 |
| 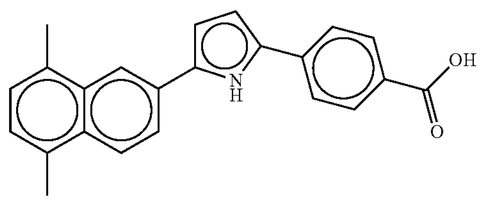 | ER-35368 |
| 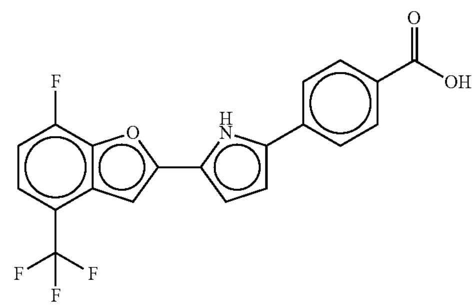 | E-6060 |
| 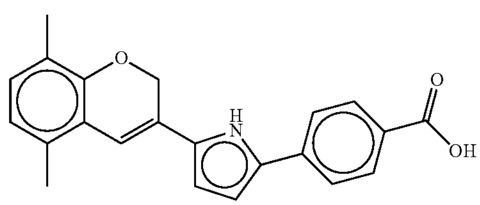 | ER-41666 |
|  | AGN-195183;<br>NRX-195183;<br>VTP-195183;<br>VTP-5183<br>IRX-5183 |
| 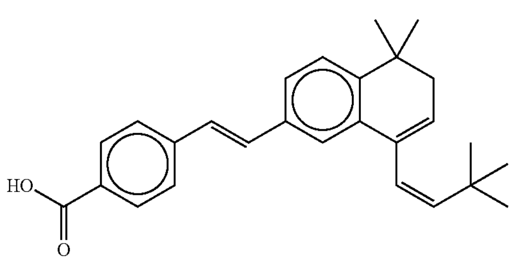 | BMS-228987 |

TABLE 1-continued
Exemplary RARA Agonists useful in the invention.
| Structure | Code Name(s) |
|---|---|
| 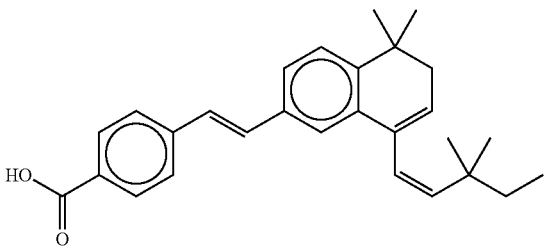 | BMS-276393 |
| 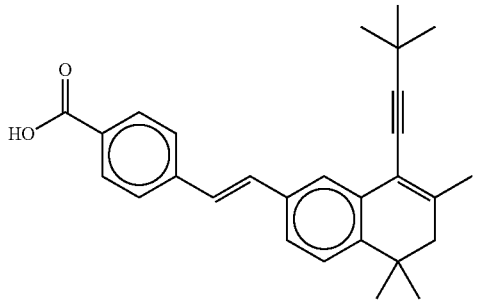 | BMS-231974 |
| 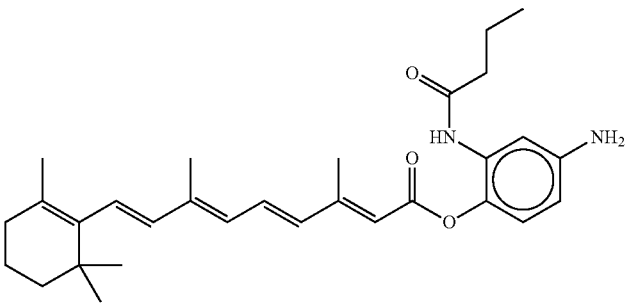 | ABPN; CBG-41 |
| 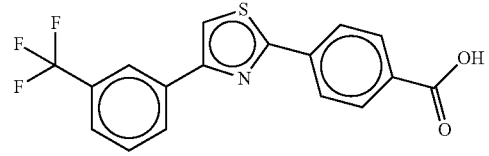 | PTB |
| 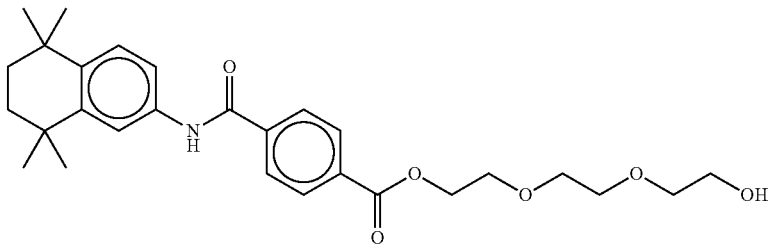 | |
| 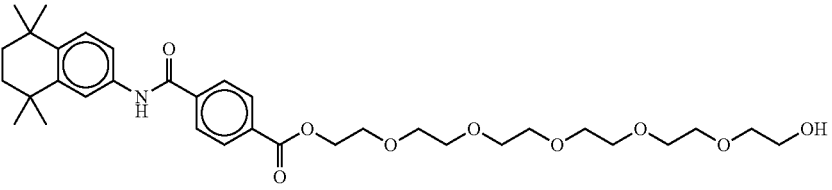 | |

TABLE 1-continued

Exemplary RARA Agonists useful in the invention.

| Structure | Code Name(s) |
|---|---|

TABLE 1-continued
Exemplary RARA Agonists useful in the invention.
| Structure | Code Name(s) |
|---|---|
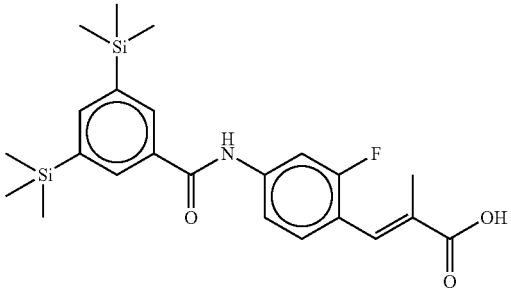
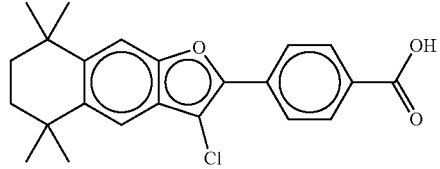
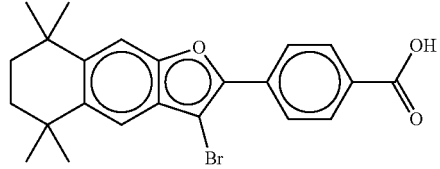
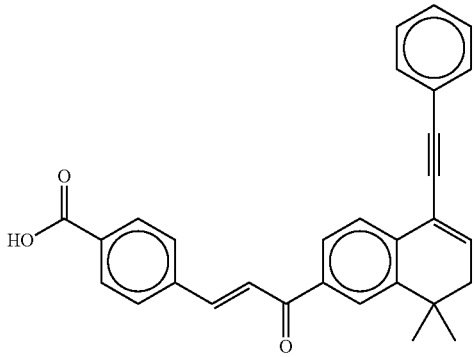
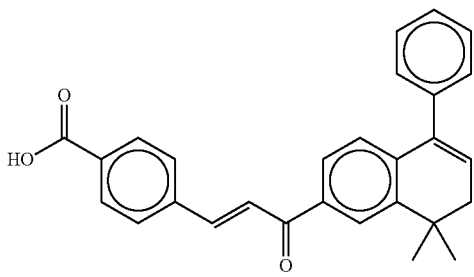

TABLE 1-continued

Exemplary RARA Agonists useful in the invention.

| Structure | Code Name(s) |
|---|---|
| | |
| | |
| | |
| 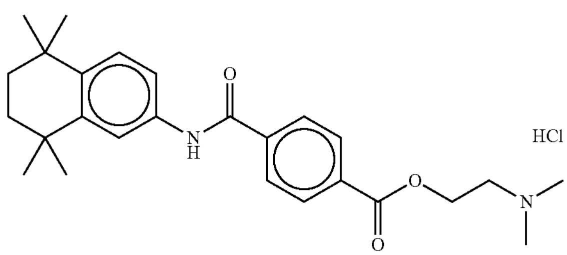 | A-112 |
| 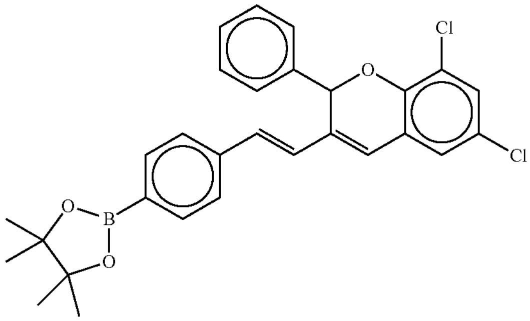 | BD-4; BJ-1 |

TABLE 1-continued

Exemplary RARA Agonists useful in the invention.

| Structure | Code Name(s) |
|---|---|
| 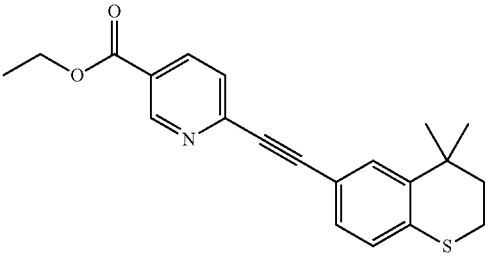 [SMILES: CCOC(=O)c1ccc(C#Cc2ccc3c(c2)C(C)(C)CCS3)nc1] | Tazarotene; AGN-190168 |
| 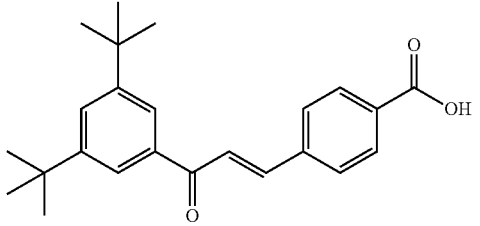 [SMILES: CC(C)(C)c1cc(C(=O)/C=C/c2ccc(C(=O)O)cc2)cc(C(C)(C)C)c1] | Ch-55 |

In some embodiments, a RARA agonist is tamibarotene.

Therapeutic Regimens

Markers and Characterization

In some embodiments, technologies provided by the present disclosure involve assessment of type of cancer from which a patient is suffering. In some embodiments, a patient is suffering from non-APL acute myelocytic leukemia (AML). In some embodiments, a patient is suffering from or myelodysplastic syndrome (MDS).

In general, the present disclosure provides technologies according to which one or more markers or characteristics of a subject is analyzed and/or assessed; in some embodiments, a therapeutic decision is made based on such analysis and/or assessment.

In some embodiments, a marker is an agent or entity whose presence, form, level, and/or activity is correlated in a relevant population with a relevant feature (e.g., type or stage of cancer). In some embodiments, the present disclosure contemplates identification, classification, and/or characterization of one or more biomarkers relevant for the treatment of non-APL AML with a RARA agonist. In some embodiments, the present disclosure contemplates identification, classification, and/or characterization of one or more biomarkers relevant for the treatment of MDS with a RARA agonist.

In some embodiments, classification of a patient as suffering from a particular type of cancer may involve assessment of stage of cancer. In some embodiments, classification of a patient as suffering from a particular type of cancer may involve assessment of disease burden in the patient (e.g. the number of cancer cells, the size of a tumor, and/or amount of cancer in the body).

In general, type of cancer may be assessed in accordance with the present invention via any appropriate assay, as will be readily appreciated by those of ordinary skill in the art. A variety of assays for cancer type are known in the art including, for example, those that utilize histological assessment (e.g., of a biopsy sample), imaging (e.g., magnetic resonance imaging (MRI), positron emission tomography (PET), computed tomography (CT) ultrasound, endoscopy, x-rays (e.g., mammogram, barium swallow, panorex), ductogram, or bone scan.

In some embodiments, RARA agonist therapy comprises assessing a level of one or more biomarkers indicative of a stage or a form of non-APL AML or MDS. In some embodiments, RARA agonist therapy comprises assessing IRF8 mRNA level and, optionally, RARA mRNA level. In some embodiments, RARA agonist therapy comprises the presence of a super enhancer associated with an IRF8 gene and, optionally, the strength or ordinal rank of a super enhancer associated with a RARA gene. In some embodiments, RARA agonist therapy comprises assessing IRF8 mRNA level or the presence of a super enhancer associated with an IRF8 gene and, optionally RARA mRNA level, the strength or ordinal rank of a super enhancer associated with a RARA gene.

Without being bound by theory, applicants believe that subsets of PBMCs that have only one of CD34 or CD117 markers can also be used effectively to determine IRF8 mRNA or super-enhancer levels. Moreover, certain IRF8 mRNA analysis techniques, such as RNAScope® do not require enriching a PBMC sample prior to analysis because those techniques provide analytical enrichment of mRNA from the desired cells based on the use of specific oligonucleotide hybridization/amplification procedures.

Patient Populations

In some embodiments, RARA agonist therapy is administered in accordance with the present disclosure to one or more patients (e.g., to a patient population) as described herein.

In some embodiments, a patient population includes one or more subjects (e.g., comprises or consists of subjects) suffering from cancer. In some embodiments, a patient population includes one or more subjects suffering from non-APL AML. In some embodiments, a patient population includes one or more subjects suffering from MDS.

In some embodiments, a patient population includes one or more subjects (e.g., comprises or consists of subjects) who received previous therapy for treatment of cancer (e.g., non-APL AML or MDS). In some embodiments, a patient population includes one or more subjects (e.g., comprises or consists of subjects) who have not received previous therapy for treatment of cancer (e.g., non-APL AML or MDS). In some embodiments, a patient population comprises or consists of patients who have not received previous therapy for treatment of non-APL AML or MDS.

In some embodiments, a patient who received previous therapy may have received previous therapy selected from the group consisting of chemotherapy, immunotherapy, radiation therapy, palliative care, surgery, and combinations thereof. In some embodiments, a patient has received a transplant. In some embodiments, a patient has received standard cytotoxic chemotherapy. In some embodiments, standard cytotoxic chemotherapy includes cytarabine and/or an anthracycline. In some embodiments, standard cytotoxic chemotherapy may include additional chemotherapy and/or hematopoietic stem cell transplantation (HSTC). In some embodiments, a patient has received hypomethylating agents. In some embodiments, a patient has received lenalidomide.

In some embodiments, a patient population includes one or more subjects (e.g., comprises or consists of subjects) who have received and/or are receiving other therapy, e.g., so that a RARA agonist therapy (e.g., tamibarotene) composition is administered in combination with the other therapy (e.g. chemotherapy agents). In some embodiments, such other therapy may comprise or consist of therapy for cancer (e.g., as described herein), pain, nausea, constipation, for treatment of one or more side effects (e.g., pruritus, hair loss, sleeplessness, etc.) associated with cancer therapy, etc., or any combination thereof. The present invention provides a method of treating non-APL AML or MDS, which comprises treating a patient identified as having non-APL AML or MDS, with a therapeutically effective amount of RARA agonist therapy (e.g., tamibarotene) or a pharmaceutically acceptable salt thereof.

In some embodiments, the present invention provides a method of preventing or delaying the onset of non-APL AML or MDS, comprising administering to a patient identified to be in need of prevention, or delaying the onset, of non-APL AML or MDS a prophylactically effective amount of a RARA agonist therapy (e.g., tamibarotene) or a pharmaceutically acceptable salt thereof.

In some embodiments, the invention provides a method for treating a patient for non-APL AML or MDS previously treated with a treatment regimen comprising chemotherapy by administering to such a patient a therapeutically effective amount of a RARA agonist therapy (e.g., tamibarotene) or a pharmaceutically acceptable salt thereof. In some embodiments, the present disclosure provides a method for treating a patient for non-APL AML or MDS where no standard therapies exist. In some embodiments, the present disclosure provides a method for treating a patient that is not suited for standard therapy.

In some embodiments, a patient may also have diseases associated with MDS, such as bone marrow failure, peripheral blood cytopenias and associated complications of anemia, infection or hemorrhage. In some embodiments, a patient may have MDS that progresses to AML.

In some embodiments, a patient or patient population may not be (e.g., may exclude) a patient who is or may be pregnant. In some embodiments, a patient or patient population may be monitored for one or more signs of pregnancy, delivery, and/or lactation prior to and/or during administration of RARA agonist therapy. In some embodiments, RARA agonist therapy may be reduced, suspended, or terminated for a patient who is determined to display one or more signs of pregnancy, delivery, and/or lactation.

In some embodiments, a patient or patient population may not be (e.g., may exclude) a patient who has a previous history of hypersensitivity to an ingredient of tamibarotene. In some embodiments, a patient or patient population may not be (e.g., may exclude) a patient who is receiving vitamin A formulations. In some embodiments, a patient or patient population may not be (e.g., may exclude) a patient who has hypervitaminosis A.

In some embodiments, a patient or patient population may not be (e.g., may exclude) an elderly patient. In some embodiments, a patient or patient population may be or include one or more elderly patients. In some embodiments, an elderly patient may be monitored more frequently to detect potential adverse events (including for example, low levels of serum albumin and/or elevated concentrations of free drug in plasma, etc) as compared with one or more younger patients. In some embodiments, RARA agonist therapy may be reduced, suspended, and/or terminated for an elderly patient determined to display one or more signs of such an adverse event.

In some embodiments, a patient or patient population may not be (e.g., may exclude) a pediatric patient. In some embodiments, a patient or patient population may be or include one or more pediatric patients. In some embodiments, a pediatric patient may be monitored more frequently to detect potential adverse events (including for example, increased intracranial pressure, etc.) as compared with one or more older patients. In some embodiments, RARA agonist therapy may be reduced, suspended, and/or terminated for a pediatric patient determined to display one or more signs of such an adverse event.

In some embodiments, RARA agonist therapy in accordance with the present disclosure is reduced, suspended or terminated for a particular patient if and when the patient develops one or more adverse reactions such as, for example headache, rash, dry skin, eczema, exfoliative dermatitis, bone pain, joint pain, fever, increased leucocyte count, decreased haemoglobin, increased AST, increased ALT, increased LDH, increased ALP, increased TG, increased TC, follicitis, folliculitis, increased CRP, and combinations thereof. Alternatively or additionally, in some embodiments, RARA agonist therapy in accordance with the present disclosure is reduced, suspended or terminated for a particular patient if and when the patient develops one or more adverse reactions such as, for example thrombosis (e.g., brain infarction, pulmonary infarction, arterial thrombosis, venous thrombosis, etc.), vasculitis, delirium, toxic epidermal necrosis (Lyell syndrome), erythema multiforme, increased intracranial pressure, and combinations thereof.

In some embodiments, the present invention provides use of a compound (e.g., tamibarotene) or a pharmaceutically acceptable salt thereof for the manufacture of a medicament useful for treating, preventing, or delaying the onset of non-APL AML or MDS. In some embodiments, the patient is suffering from cancer (e.g., non-APL AML or MDS). In some embodiments, the patient is suffering from cancer (e.g., non-APL AML or MDS) that is resistant to other therapies (e.g., chemotherapy). In some embodiments, the cancer is determined to have an IRF8 biomarker, wherein the IRF8 biomarker is or comprises expression of one or more of elevated IRF8 mRNA levels or a super enhancer associated with an IRF8 gene. In some embodiments, the cancer is determined to express or more of elevated RARA mRNA levels or a super enhancer associated with a RARA gene. In some embodiments, the cancer is determined not to express or more of elevated RARA mRNA levels or a super enhancer associated with a RARA gene.

Dose Forms and Dosing Regimens

In general, each active agent (e.g., tamibarotene) for use in accordance with the present invention is formulated, dosed, and administered in a therapeutically effective amount using pharmaceutical compositions and dosing regimens that are consistently with good medical practice and appropriate for the relevant agent(s) and subject. In principle, therapeutic compositions can be administered by any appropriate method known in the art, including, without limitation, oral, mucosal, by-inhalation, topical, buccal, nasal, rectal, or parenteral (e.g., intravenous, infusion, intratumoral, intranodal, subcutaneous, intraperitoneal, intramuscular, intradermal, transdermal, or other kinds of administration). In some embodiments, a RARA agonist (e.g., tamibarotene) will be administered orally.

In some embodiments, a dosing regimen for a particular active agent may involve intermittent or continuous administration, for example to achieve a particular desired pharmacokinetic profile or other pattern of exposure in one or more tissues or fluids of interest in the subject receiving therapy.

In some embodiments, different agents administered in combination may be administered via different routes of delivery and/or according to different schedules. Alternatively or additionally, in some embodiments, one or more doses of a first active agent is administered substantially simultaneously with, and in some embodiments via a common route and/or as part of a single composition with, one or more other active agents.

Factors to be considered when optimizing routes and/or dosing schedule for a given therapeutic regimen may include, for example, the particular indication being treated, the clinical condition of a subject (e.g., age, overall health, prior therapy received and/or response thereto, etc.) the site of delivery of the agent, the nature of the agent, the mode and/or route of administration of the agent, the presence or absence of combination therapy, and other factors known to medical practitioners. For example, in the treatment of cancer, relevant features of the indication being treated may include, among other things, one or more of cancer type, stage, location, etc.

In some embodiments, one or more features of a particular pharmaceutical composition and/or of a utilized dosing regimen may be modified over time (e.g., increasing or decreasing amount of active in any individual dose, increasing or decreasing time intervals between doses, etc.), for example in order to optimize a desired therapeutic effect or response.

In general, type, amount, and frequency of dosing of active agents in accordance with the present invention are governed by safety and efficacy requirements that apply when relevant agent(s) is/are administered to a mammal, preferably a human. In general, such features of dosing are selected to provide a particular, and typically detectable, therapeutic response as compared with what is observed absent therapy. In some embodiments, a RARA agonist (e.g., tamibarotene) will be administered continuously.

In context of the present invention, an exemplary desirable therapeutic response may involve, but is not limited to, inhibition of and/or decreased tumor growth, tumor size, metastasis, one or more of the symptoms and side effects that are associated with a tumor, as well as increased apoptosis of tumor cells, therapeutically relevant decrease or increase of one or more cell marker or circulating markers and the like. Such criteria can be readily assessed by any of a variety of immunological, cytological, and other methods that are disclosed in the literature.

In some embodiments, it may be desirable to tailor dosing regimens, and particularly to design sequential dosing regimens, based on timing and/or threshold expression levels of inducible markers, whether for particular types of tumors, particular tumors, particular patient populations (e.g., carrying genetic markers), and/or particular patients. In some such embodiments, therapeutic dosing regimens may be combined with or adjusted in light of detection methods that assess expression of one or more inducible markers prior to and/or during therapy.

In some embodiments, a RARA agonist (e.g., tamibarotene) therapy regimen comprises at least one (or includes or consists of exactly one) dose of about 1 mg/m$^2$, 2 mg/m$^2$, 3 mg/m$^2$, 4 mg/m$^2$, 5 mg/m$^2$, 6 mg/m$^2$, 7 mg/m$^2$, 8 mg/m$^2$, 9 mg/m$^2$, 10 mg/m$^2$, 11 mg/m$^2$, 12 mg/m$^2$, 13 mg/m$^2$, 14 mg/m$^2$, 15 mg/m$^2$, 16 mg/m$^2$, or a dose between any two of these values of tamibarotene. In some embodiments, a tamibarotene therapy regimen comprises a dose of 6 mg/m$^2$. In some embodiments, a tamibarotene therapy regimen comprises a dose of 4 mg/m$^2$. In some embodiments, a tamibarotene therapy regimen comprises a dose of 2 mg/m$^2$. In some embodiments, a tamibarotene therapy regimen comprises a dose of 1 mg/m$^2$.

In some embodiments, a RARA agonist (e.g., tamibarotene) therapy regimen comprises a plurality of doses of a tamibarotene composition. In some such embodiments, a tamibarotene therapy regimen comprises, for example 2, 5, 10, 20, 30, 60, 90, 180, 365 doses or a number of doses between any two of these values and/or comprises a repeated pattern of doses (e.g., at least one cycle of two daily doses, which cycle may be repeated, optionally with a period of alternative administration, or optionally no administration, separating different cycles). In some embodiments, a tamibarotene therapy regimen is administered twice a day. In some embodiments, a tamibarotene therapy regimen is administered once a day. In some embodiments, a tamibarotene therapy regimen comprises a total dose of 6 mg/m$^2$, divided as twice daily oral dosing.

In some embodiments, a RARA agonist (e.g., tamibarotene) therapy regimen may be administered to a subject or population of patients known to have consumed, or not consumed, some amount of food before, during or after the administration. The terms "before administration" and "after administration" with respect to food intake may refer to a period of time of about 1, 2, 3, 4, 5, 6, 7, 8, 9, 10, 11, 12, 14, 16, 18, 20, 22, 24, 30, 42, or 72 hours, or longer, before or after the administration. In some embodiments, the term "administering . . . with regard to food intake" implies that the subject or population of patients consumes food before the administration (e.g., fed state). In some embodiments, the term "administering . . . with regard to food intake" implies that the subject or population of patients consumes food after the administration. In some embodiments, the term "administering . . . with regard to food intake" implies that the subject or population of patients consumes food during the administration. Alternatively, in some embodiments, the term "administering . . . with regard to food intake" means the subject or population of patients is in a fasted state during administration.

In some embodiments, food intake includes high fat foods or a high fat diet. In some embodiments, a RARA agonist (e.g., tamibarotene) therapy regimen is administered to a subject in a fasted state. In some embodiments, a RARA agonist (e.g., tamibarotene) therapy regimen is administered to a subject in a fed state.

Formulations

A pharmaceutical composition, as used herein, refers to a mixture of a compound, such as tamibarotene, with other chemical components, such as carriers, stabilizers, diluents, dispersing agents, suspending agents, thickening agents, and/or excipients. The pharmaceutical composition facilitates administration of the compound to an organism. Pharmaceutical compositions containing a compound may be administered in therapeutically effective amounts by any conventional form and route known in the art including, but not limited to: intravenous, oral, rectal, aerosol, parenteral, ophthalmic, pulmonary, transdermal, vaginal, otic, nasal, and topical administration.

One may administer the compound in a local rather than systemic manner, for example, via injection of the compound directly into an organ, often in a depot or sustained release formulation. Furthermore, one may administer pharmaceutical composition containing a compound in a targeted drug delivery system, for example, in a liposome coated with organ-specific antibody. The liposomes will be targeted to and taken up selectively by the organ. In addition, the pharmaceutical composition containing a compound may be provided in the form of a rapid release formulation, in the form of an extended release formulation, or in the form of an intermediate release formulation. In some embodiments, the extended release formulation releases the compound for over 1 hour, over 2 hours, over 3 hours, over 4 hours, over 6 hours, over 12 hours, over 24 hours, or more. In some embodiments, the extended release formulation releases the compound at a steady rate for over 1 hour, over 2 hours, over 3 hours, over 4 hours, over 6 hours, over 12 hours, over 24 hours, or more.

For oral administration, a compound can be formulated readily by combining the active compounds with pharmaceutically acceptable carriers or excipients well known in the art. Such carriers permit the compounds described herein to be formulated as tablets, powders, pills, dragees, capsules, liquids, gels, syrups, elixirs, slurries, suspensions and the like, for oral ingestion by a subject to be treated. Generally, excipients such as fillers, disintegrants, glidants, surfactants, recrystallization inhibitors, lubricants, pigments, binders, flavoring agents, and so forth can be used for customary purposes and in typical amounts without affecting the properties of the compositions. In some embodiments, the excipient is one or more of lactose hydrate, corn starch, hydroxypropyl cellulose and/or magnesium stearate. In some embodiments, tamibarotene may be formulated with one or more of lactose hydrate, corn starch, hydroxypropyl cellulose and/or magnesium stearate.

The identification of acceptable formulations of tamibarotene can be achieved by various methods known in the art, for example as described in US 20100048708, which is incorporated herein by reference.

Combination Therapy

Those of ordinary skill in the art, reading the present disclosure, will readily appreciate that a RARA agonist (e.g., tamibarotene), as described herein, may in certain embodiments be combined with other anti-cancer therapies, including for example administration of chemotherapeutic agents, other immunomodulatory agents, radiation therapy, high-frequency ultrasound therapy, surgery, FDA approved therapies for treatment of cancer, etc.

In some embodiments, a RARA agonist is utilized in combination with one or more other therapeutic agents or modalities. In some embodiments, the one or more other therapeutic agents or modalities is also an anti-cancer agent or modality; in some embodiments the combination shows a synergistic effect in treating cancer.

Known compounds or treatments that show therapeutic efficacy in treating cancer may include, for example, one or more alkylating agents, anti-metabolites, anti-microtubule agents, topoisomerase inhibitors, cytotoxic antibiotics, angiogenesis inhibitors, immunomodulators, vaccines, cell-based therapies, organ transplantation, radiation therapy, surgery, etc.

In some embodiments, a RARA agonist (and/or other therapy with which it is combined) may be combined with one or more palliative (e.g., pain relieving, anti-nausea, anti-emesis, etc.) therapies, particularly when relieves one or more symptoms known to be associated with the relevant cancer, or with another disease, disorder or condition to which a particular cancer patient is susceptible or from which the particular cancer patient is suffering.

In some embodiments, agents used in combination are administered according to a dosing regimen for which they are approved for individual use. In some embodiments, however, combination with a RARA agonist (e.g., tamibarotene) permits another agent to be administered according to a dosing regimen that involves one or more lower and/or less frequent doses, and/or a reduced number of cycles as compared with that utilized when the agent is administered without a RARA agonist (e.g., tamibarotene). Alternatively or additionally, in some embodiments, an appropriate dosing regimen involves higher and/or more frequent doses, and/or an increased number of cycles as compared with that utilized when the agent is administered without a RARA agonist (e.g., tamibarotene).

In some embodiments, one or more doses of agents administered in combination are administered at the same time; in some such embodiments, agents may be administered in the same composition. More commonly, however, agents are administered in different compositions and/or at different times. In some embodiments, tamibarotene is administered sequentially and/or concurrently with other therapeutic agents (e.g., chemotherapy).

In some embodiments, the combination therapies disclosed herein are only administered if a subject has a RARA mRNA level equal to or above a threshold value. In some embodiments, the combination therapies disclosed herein are only administered if a subject has an IRF8 mRNA level equal to or above a threshold value. In some embodiments, the combination therapies disclosed herein are only administered to a subject that has both a RARA mRNA level equal to or above a threshold value and an IRF8 mRNA level equal to or above a threshold value. In some aspects of any of these embodiments, the subject is suffering from non-APL AML.

In some embodiments, the therapeutic agent to be combined with a RARA agonist (e.g. tamibarotene) is selected from a DNA methyltransferase inhibitor, a DNA synthase inhibitor, a topoisomerase inhibitor, a FLT3 inhibitor, a folate inhibitor, a BRD4 inhibitor, a Zn finger transcription factor inhibitor, a GCR inhibitor, a CDK7 inhibitor, an HDAC inhibitor, a JMJD3/JARID1B inhibitor, or an EZH2 inhibitor. In other specific aspects, that second agent is selected from a LSD1 inhibitor, a proteasome inhibitor, a DNA damage repair inhibitor, a PARP inhibitor, a mTOR inhibitor, a DOT1L inhibitor, a tubulin inhibitor, a PLK inhibitor, or an Aurora kinase inhibitor.

In some embodiments, a RARA agonist (e.g., tamibarotene) can be administered with decitabine, azacitidine, ara-C, daunorubicin, idarubicin, arsenic trioxide and/or flt3 inhibitors. In some embodiments, a RARA agonist (e.g., tamibarotene) can be administered with IDH inhibitors, BRD4 inhibitors (e.g., JQ1), HDAC inhibitors (e.g., SAHA and MC1568), HMT inhibitors (e.g., EPZ6438, UNC0638, SGC707, EPZ5676, UNC037 and PFI-2) and/or KDM inhibitors (e.g., GSKJ4, RN-1 and GSK-LSD1).

In some embodiments, the subject is suffering from AML and tamibarotene is administered in combination with a second agent selected from azacytidine, arsenic trioxide, midostaurin (only in those AML subjects characterized by high FLT3 mRNA levels), cytarabine, daunorubicin, methotrexate, idarubicin, sorafenib (only in those AML subjects characterized by high FLT3 mRNA levels), decitabine, quizartinib (only in those AML subjects characterized by high FLT3 mRNA levels), JQ1 (a BRD4 inhibitor), ATO, prednisone (only in those AML subjects characterized by high GCR mRNA levels), SAHA, and GSKJ4 (only in those AML subjects characterized by high JMJD3/JARID1B mRNA levels).

Kits

A kit comprising one or more reagents for detecting one or more IRF8 biomarkers can be provided in a kit. In some instances, the kit includes packaged pharmaceutical compositions of the present invention comprising a written insert or label with instructions to use a RARA agonist (e.g., tamibarotene) in a subject suffering from a cancer and who has been determined to have a super enhancer associated with an IRF8 gene having a strength, or ordinal rank equal to or above a threshold level, or an IRF8 mRNA level equal to or above a reference (e.g., threshold level). As described in detail above, the threshold level is determined in a population of samples from either subjects diagnosed as suffering from the same disease or cell lines or xenograft models of the same disease as that for which the pharmaceutical composition is indicated for treatment. The instructions may be adhered or otherwise attached to a vessel comprising a RARA agonist. Alternatively, the instructions and the vessel comprising a RARA agonist will be separate from one another, but present together in a single kit, package, box, or other type of container.

The instructions in the kit will typically be mandated or recommended by a governmental agency approving the therapeutic use of a RARA agonist. The instructions may comprise specific methods of determining whether a super enhancer is associated with an IRF8 gene, as well as quantification methods to determine whether an enhancer associated with an IRF8 gene is a super enhancer, quantification methods to determine IRF8 mRNA levels; and/or threshold levels of super enhancers or IRF8 mRNA at which treatment with a packaged RARA agonist is recommended and/or assumed therapeutically effective. In some aspects, the instructions direct that the composition be administered to a subject whose IRF8 mRNA level falls in at least the $30^{th}$ percentile of a population whose IRF8 mRNA levels have been measured. In some aspects of these embodiments, a subject is identified as a RARA agonist responder if its IRF8 mRNA level prevalence rank is about 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 43%, 42%, 51%, 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, or 20% in a population whose IRF8 mRNA levels have been measured. In some aspects, the instructions direct that the composition be administered to a subject whose IRF8 mRNA level as measured by a specific assay The instructions may optionally comprise dosing information, the types of cancer for which treatment with a RARA agonist was approved, physicochemical information about a RARA agonist; pharmacokinetic information about a RARA agonist, drug-drug interaction information. In some embodiments, the instructions direct that the composition be administered to a subject diagnosed as suffering from AML. In some embodiments, the instructions direct that the composition be administered to a subject diagnosed as suffering from non-APL AML. In some aspects, the instructions direct that the composition be administered to a subject diagnosed as suffering from MDS. In some aspects, the pharmaceutical composition comprises tamibarotene.

EXAMPLES

In order that the invention described herein may be more fully understood, the following examples are set forth. The synthetic and biological examples described in this application are offered to illustrate the compounds, pharmaceutical compositions, and methods provided herein and are not to be construed in any way as limiting their scope.

Example 1: IRF8 mRNA Levels in Non-APL AML Cell Lines Correlate with Responsiveness to a RARA Agonist We previously tested several AML cell lines for sensitivity to tamibarotene and demonstrated that sensitivity correlated very well with each of RARA super enhancer strength, RARA super enhancer strength ordinal and RARA mRNA level. This was done as described below.

On the day of the experiment, cells were homogenized using Accumax (EMD Millipore), counted, and adjusted to 60,000 cells/mL in appropriate growth media. Using a Biotek EL406, 50 µl of cells were distributed into white (ATPlite) or black (CyQuant) 384-well plates (Thermo). Cells were returned to 37° C. incubator to allow adhesion. After three hours, compounds were added to plates using a 20 nl 384-well pin transfer manifold on a Janus workstation. Stocks were arrayed in 10 point quadruplicate dose response in DMSO stock in 384-well compound plates. After addition of compound, plates were incubated for five or ten days in a 37° C. incubator.

Cell viability was read out using ATPlite (Perkin Elmer) or CyQuant (Life Technologies). For ATPlite, plates were removed from the incubator and brought to room temperature prior to use. Lyophilized powder of ATPlite reagent was resuspended in lysis buffer and diluted 1:2 with distilled water. 25 µL of this solution was added to each well using the Biotek liquid handler. Plates were incubated for 15 min at room temperature before the luminescence signal was read on an Envision Plate Reader (Perkin Elmer). For CyQuant, reagents were mixed as per manufacturer's instructions in PBS (Gibco). Reagent was added using a multichannel pipet and plates were replaced in incubator for 30 minutes prior to readout on an Envision Plate Reader (Perkin Elmer).

Data acquired as described was stored and grouped in Microsoft's Excel and analyzed using GraphPad Prism Software. Curve fits to calculate $EC_{50}$ and $E_{max}$ were done in GraphPad Prism version 6.0 using four parameter (Hill slope not assumed to be equal to 1) non-linear regressions with the log 10 transformed data of the compound concentrations plotted against the percent viability of the cells when normalized to DMSO only treated wells included on the plate. Edge wells were excluded.

We used an Affymetrix GeneChip® PrimeView™ Human Gene Expression Array to initially examine seven of these AML cell lines (four sensitive to tamibarotene-NOMO-1, OCI-AML3, MV-4-11, and Sig-M5; and three insensitive-KG1a, OCI-M1 and Kasumi-1) for other mRNAs that might be specifically elevated in the tamibarotene sensitive cell lines and identified IRF8 mRNA as a potential candidate. We then quantified IRF8 mRNA levels in each of these seven AML cell lines previously, as well as several other AML cell lines tested for sensitivity to tamibarotene by performing RNA-seq analysis as set forth below. The results for the first seven cell lines are shown in FIG. 1. Interestingly, NOMO-1 did not have a high RARA mRNA level, but was responsive to tamibarotene. The fact that NOMO-1 had elevated IRF8 mRNA levels helped clarify this seeming inconsistency and further validated the use of IRF8 mRNA levels to predict responsiveness to tamibarotene.

RNA Preparation:

Cell suspension was transferred to microcentrifuge tubes and washed with 1 mL of PBS. Cell pellets were re-suspended in 200 µL of TRIzol. 20 µL of miRNA Homogenate Additive from the Ambion miRVana miRNA Isolation Kit (AM1561) was added, mixed, and incubated on ice for 10 minutes. 20 µL of bromochloropropane was added, mixed, incubated at room temperature for 5 minutes, and centrifuged at 12,000×g for 10 minutes at 4° C. 62 µL of the aqueous phase was added to 78 µL of ethanol and transferred to a filter column. The isolation was continued according to Ambion's Total RNA Isolation protocol. Sample was tested for quality control on a bioanalyzer and then sent to the Whitehead Sequencing Core, (Cambridge, Mass.) for sequencing.

RNA-Seq Data Processing:

Reads were aligned to the HG19 transcriptome using rsem v1.2.21 software (rsem-calculate-expression; parameters=-p 4--samtools-sort-mem 3G--ci-memory 3072--bowtie-chunkmbs 1024--quiet--output-genome-bam--bowtie2--bowtie2-path/data/devtools/bowtie-2.0.5--strand-specific) and then mRNA quantification was done using the same rsem suite (rsem-parse-alignments, rsem-build-read-index, rsem-run-em) and reported in transcripts per million (TPM). All protein coding genes were then extracted for each sample and their scores were quantile normalized.

Figure 2:
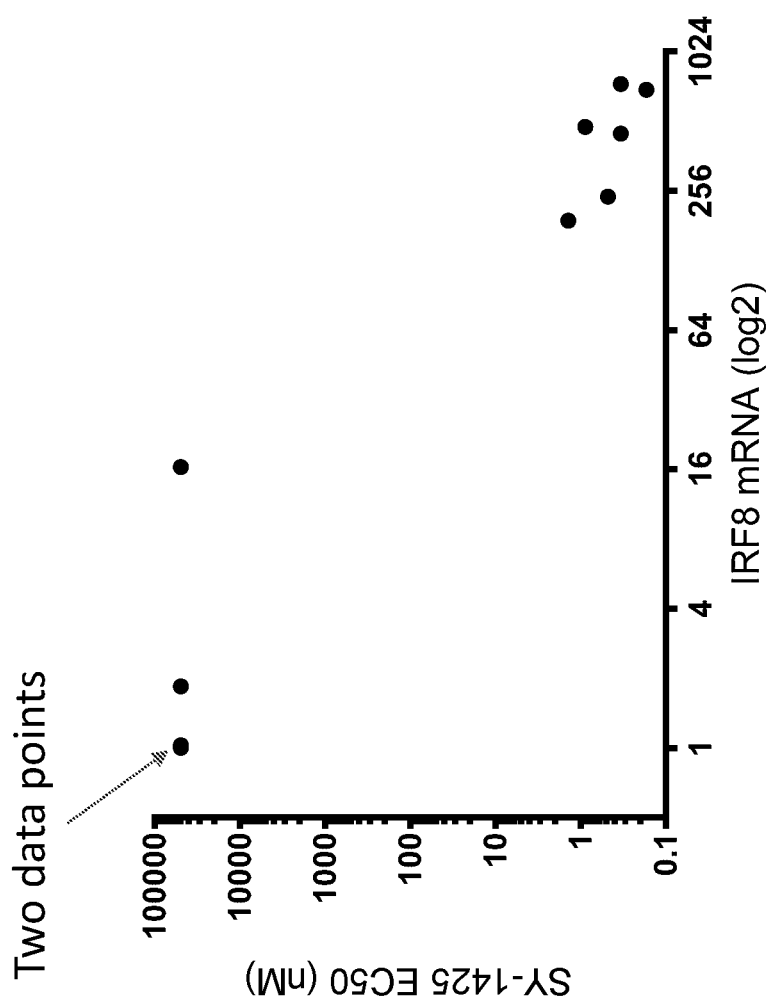
FIG. 2 shows correlation of tamibarotene anti-proliferative potency ($EC_{50}$ value, nM) with IRF8 mRNA levels as measured by RNA-seq. Note that the top-left point with IRF8 mRNA level=1 (log 10) and tamibarotene $EC_{50}$ value imputed as 50 μM (non-responsive) represents data from 2 AML cell lines with low IRF8 mRNA levels and no anti-proliferative response to tamibarotene. The correlation of tamibarotene sensitivity with IRF8 mRNA levels was highly significant (p=0.0001, Spearman's correlation, two-tailed).

We then compared sensitivity to tamibarotene to IRF8 mRNA levels as shown in FIG. 2 and Table 1.

TABLE 1

AML cell line IRF8 mRNA levels and tamibarotene anti-proliferative potency

| Cell Line | IRF8 mRNA (TPM) | Tamibarotene anti-proliferative potency ($EC_{50}$, nM) |
| --- | --- | --- |
| EOL-1 | 484.38 | 0.89 |
| Kasumi-1 | 16.34 | >50000 |
| KG-1a | 1.84 | >50000 |
| PL21 | 190.02 | 1.41 |
| MV4-11 | 699.41 | 0.17 |
| HL60* | 6.73 | 1.64 |
| OCI-AML3 | 739.29 | 0.34 |
| OCI-AML2 | 451.94 | 0.34 |
| Nomo-1 | 242.19 | 0.48 |
| OCI-M1 | 1.02 | >50000 |
| HEL | 1.00 | >50000 |

*HL60 is an APL cell line.

As can be seen from the above table, all tamibarotene-responsive cell lines, except for HL60, had an IRF8 mRNA level of greater than 190 TPM ($\log_2(7.57)$) in the assay, while non-responsive cell lines all had an IRF8 mRNA level of less than 16.5 TPM ($\log_2(4.03)$). The responsiveness of HL60 to tamibarotene without a concomitant high level of IRF8 mRNA (6.73 TPM) suggests that correlation between IRF8 mRNA level and tamibarotene sensitivity may not hold for APL and thus may be better suited to stratify subjects suffering from non-APL AML. FIG. 2 removes the data point for HL60.

Figure 14:
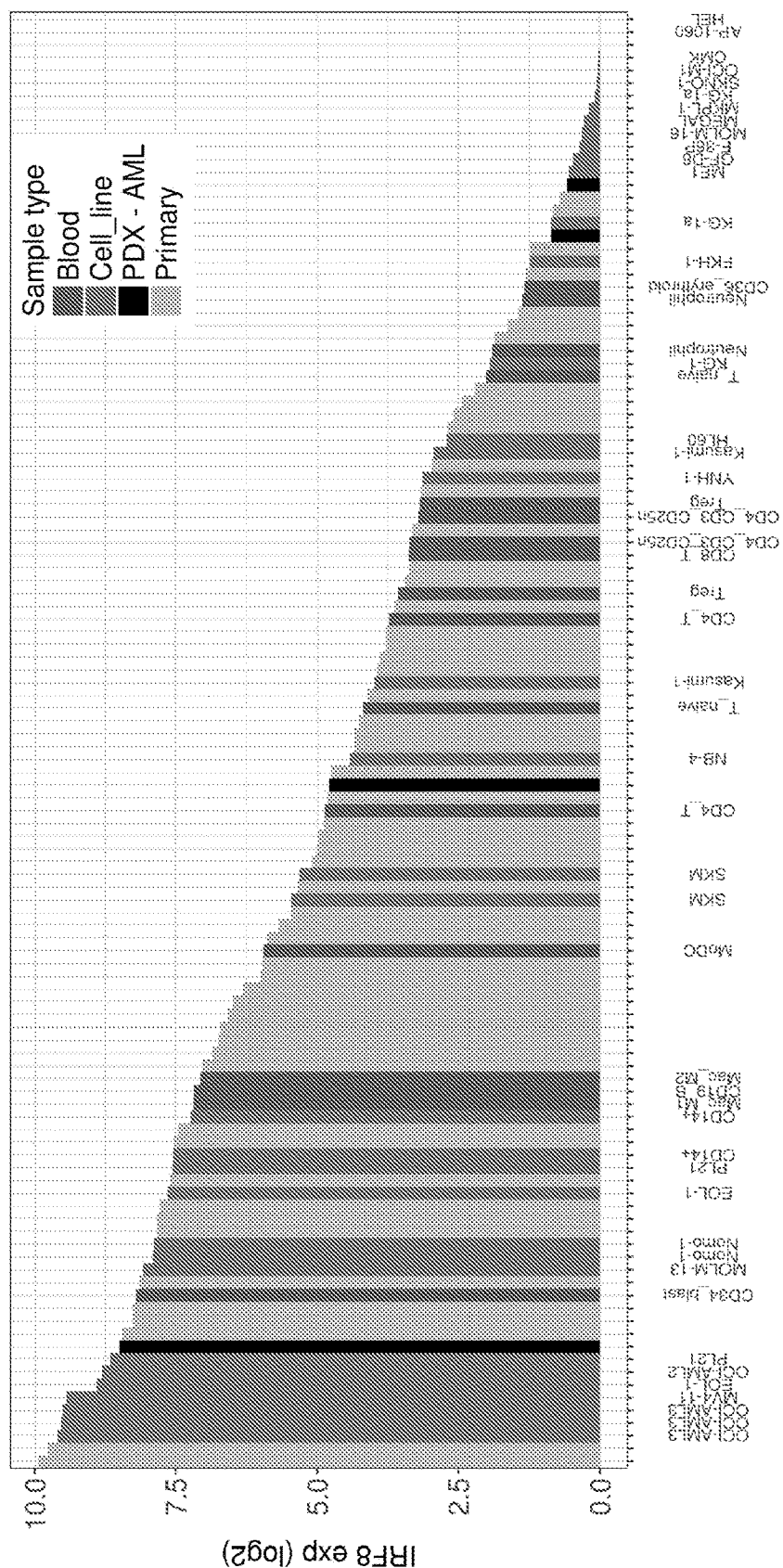
FIG. 14 depicts a rank ordering of IRF8 mRNA levels detected in a variety of AML cell lines, AML primary patient samples, normal blood cells and AML PDXs.

IRF8 mRNA levels were determined for a large number of different types of samples—normal blood cells, AML cell lines, primary AML patient samples and AML PDXs. Data obtained were plotted in rank order, and the results are presented graphically in FIG. 14. As can be seen, FIG. 14 does not show any correlation between IRF8 mRNA levels and presence of disease; and IRF8 levels appear to be distributed in a reasonably similar manner in normal cells as compared with diseased cells, cell lines and PDXs.

Figure 3:
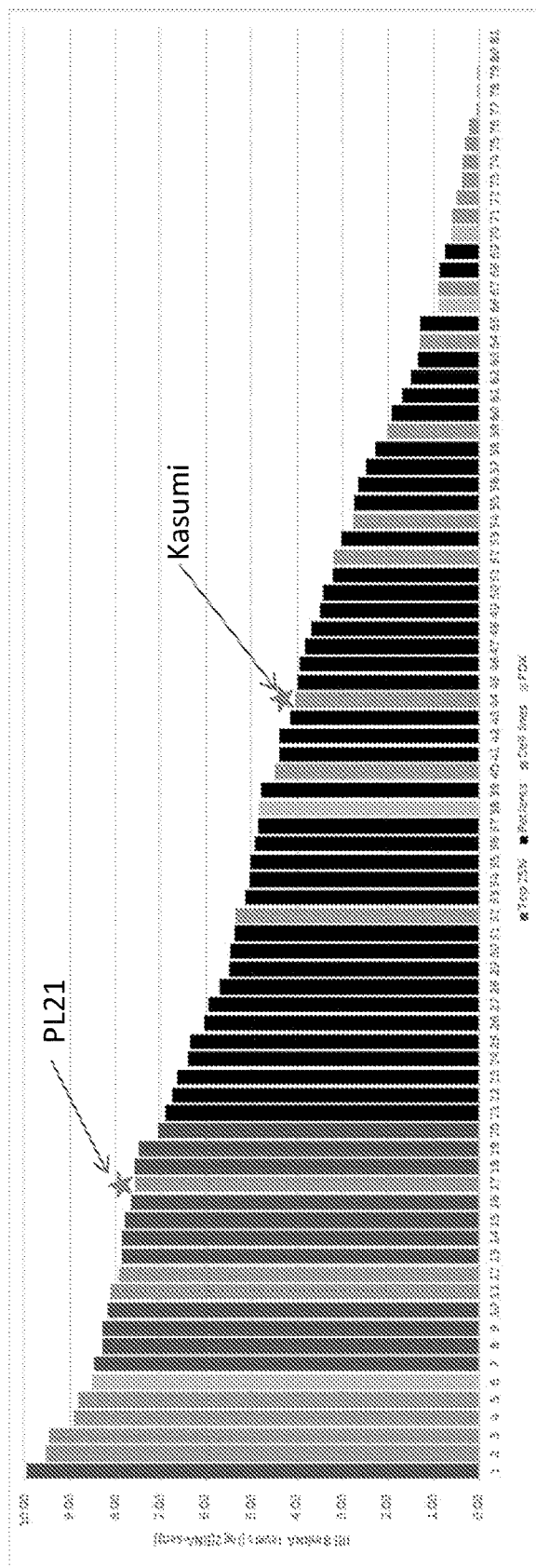
FIG. 3 depicts a rank order graph of IRF8 mRNA level in individual patient AML samples and AML cell lines as measured by RNA-Seq. The AML cell lines PL21, which was the cell line that had the lowest IRF8 mRNA level of any responsive cell line, and Kasumi, which was the cell line that had the highest IRF8 mRNA level of any cell line unresponsive to tamibarotene, are indicated. In this population, a 25% prevalence cutoff is equal to a RNA-Seq TPM value of approximately $\log_2(7)$.

Example 2: Determination of IRF8 mRNA Threshold Values for RARA Agonist Treatment The AML cell line results suggest a cutoff value of between 15.5 and 190 TPM (i.e., between $\log_2(4.03)$ and $\log_2(7.57)$ in the RNA-Seq assay. We chose a population of AML patient samples (kindly provided by Stanford University) in order to examine the distribution of IRF mRNA levels and to determine prevalence cutoffs based on the cutoff values. We added to that population AML cell lines and then generated a rank-ordered graph. FIG. 3 shows that rank-ordered distribution of IRF8 mRNA levels in the combined patient sample/AML cell line population. We determined that a prevalence cutoff of 25% corresponded to an IRF mRNA value of approximately $\log_2(7)$.

Example 3: Correlation of IRF8 mRNA and RARA mRNA Levels

Figure 4:
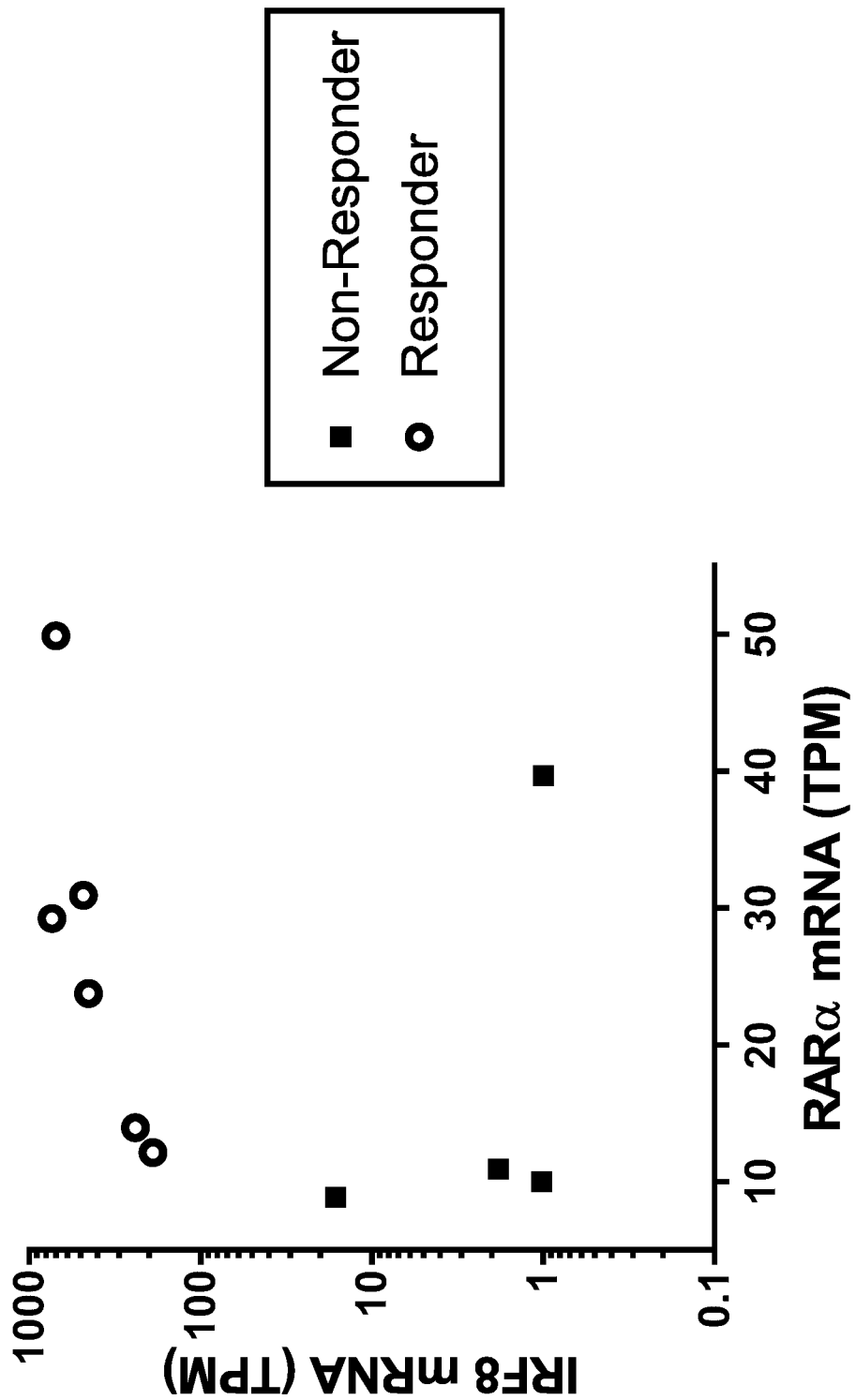
FIG. 4 depicts the correlation between IRF8 mRNA level and RARA mRNA level in non-APL AML cell lines tested for response to tamibarotene.
Figure 5:
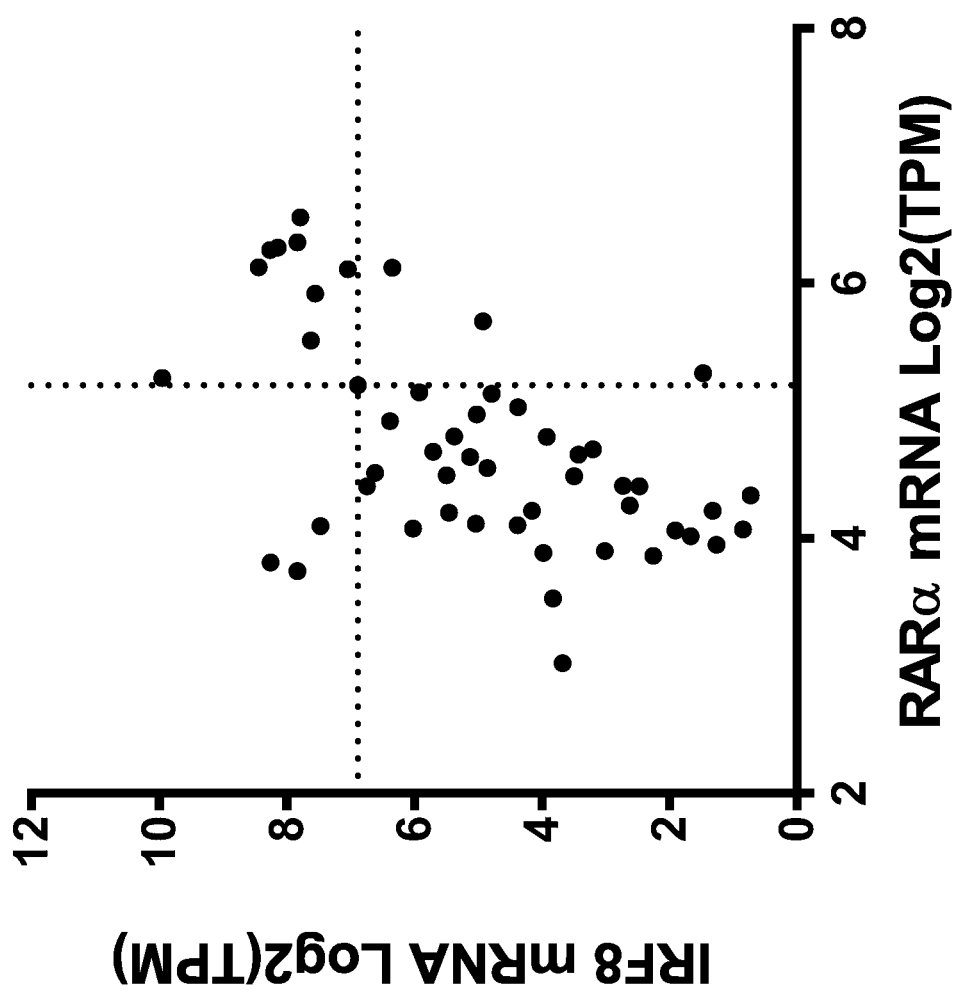
FIG. 5 depicts the correlation between IRF8 mRNA level and RARA mRNA level in a population of AML patient samples. The dotted lines represent a 25% prevalence cutoff for each mRNA

We next compared IRF8 and RARA mRNA levels in AML cell lines and patient population to determine correlation. FIG. 4 shows that some cell lines that responded to tamibarotene have relatively low RARA mRNA, but a high level of IRF8 mRNA. FIG. 5 shows that a subset of patients, too, demonstrates high IRF8 mRNA levels, but relatively low RARA mRNA levels and vice versa. This supports the idea that measuring both IRF8 and RARA mRNA in a patient and selecting that patient for treatment with a RARA agonist, such as tamibarotene, if either mRNA level is above a threshold value may optimize the treatable patient population.

Example 4: A Super Enhancer Associated with IRF8 Correlates with Responsiveness to RARA Agonist Treatment We next examined IRF8 enhancer strength in several AML cell lines and patient samples as follows.

Cell Fixation:

For cells in suspension, typically a ⅒ volume of fresh 11% formaldehyde solution was added to cell suspension, mixed and the mixture was allowed to sit at room temperature (RT) for 8 min. Then 1/20 volume of 2.5 M glycine or ½ volume of 1 M Tris pH 7.5 was added to quench formaldehyde and incubated for at least 1 min. Cells were rinsed 3 times with 20-50 mL cold 1× phosphate-buffered saline (PBS), centrifuged for 5 min at 1250×g to pellet the cells before and after each wash. Cells were then transferred to 15 mL conical tubes and centrifuged at 1250×g for 5 minutes at 4° C. The supernatant was removed, residual liquid was removed by dabbing with a Kimwipe, and then the pelleted cells were flash frozen in liquid nitrogen and stored at −80° C.

Bead Preparation:

Approximately 60 µL of Dynabeads® Protein G per 2 mL immunoprecipitate (Invitrogen) were used. Beads were washed 3 times for 5 minutes each with 1.0 mL blocking buffer (0.5% BSA w/v in PBS) in a 1.5-mL Eppendorf tube. A magnet (Invitrogen) was used to collect the beads (and allowed magnet binding for at least 1 full minute) after each wash and the supernatant was then aspirated. The washed beads were re-suspended in 250 µL blocking buffer to which 6 µg of antibody was added and the mixture was allowed to incubate with end-over-end mixing overnight (minimum 6 hours). The antibody-bound beads were washed 3 times for 5 min each with 1 mL blocking buffer and re-suspended in blocking buffer (60 µL per IP). These last washes and resuspensions were done once the cells were sonicated (see 9.1.1.3) and just prior to overnight immunoprecipitation.

Cell Lysis:

Protease inhibitors at 1× (Complete, Roche; prepared by dissolving one tablet in 1 mL $H_2O$ for 50× solution and stored in aliquots at −20° C.) were added to all lysis buffers before use. Each tube of cells (approximately $5×10^7$ cells) was re-suspended in 5-10 mL of lysis buffer 1 (LB1; 140 mM NaCl, 1 mM EDTA, 10% glycerol, 0.5% NP-40, 0.25% Triton X-100) and rocked at 4° C. for 10 minutes. The cells were centrifuged at 1250×g×5 min in tabletop centrifuge at 4° C. and the supernatant aspirated off. The cells were re-suspended in 5 mL Lysis Buffer 2 (LB2; 200 mM NaCl, 1 mM EDTA, 0.5 mM EGTA, 10 mM Tris pH 8) and incubated end-over-end at 4° C. for 10 minutes. The cells were again pelleted at 1250×g for 5 min in tabletop centrifuge at 4° C. and washed in 2-5 mL Covaris sonication buffer (10 mM Tris pH 8.0, 1 mM EDTA, 0.1% SDS). The pellet was centrifuged at 1250×g for 5 min in tabletop centrifuge at 4° C. The cells were pelleted at 1250×g for 5 min in a tabletop centrifuge at 4° C. and re-suspended at a concentration of 20-50 million cells/1 mL of Covaris sonication buffer.

Chromatin Immunoprecipitation:

Fifty µL of antibody-conjugated beads prepared as described above was added to the cleared cellular extract (as described above in Cell Lysis) solution in 1.5 ml tubes and rocked overnight at 4° C. (minimum 8 hours) to immunoprecipitate DNA-protein complexes.

Wash, Elution, and Cross-Link Reversal:

All buffers used in these steps were ice cold. A magnetic stand was used to precipitate magnetic beads, washed 3 times, 5 minutes each, with gentle end-over-end mixing with 1 mL Wash Buffer 1 (50 mM HEPES pH 7.5; 140 mM NaCl; 1 mM EDTA; 1 mM EGTA; 0.75% Triton-X; 0.1% SDS; 0.05% DOC); washed once for 5 minutes with 1 mL Wash Buffer 2 (50 mM HEPES pH 7.5; 500 mM NaCl; 1 mM EDTA; 1 mM EGTA; 0.75% Triton-X; 0.1% SDS; 0.05% DOC); and once for 5 minutes with 1 mL Wash Buffer 3 (10 mM Tris pH 8.0; 1 mM EDTA; 50 mM NaCl). All residual wash buffer was aspirated and the beads were centrifuged gently at 1250×g for 1 min; the tubes were replaced onto the magnet and all traces of buffer were removed. Elution buffer at a volume of 210 µL was added (50 mM Tris pH 8; 10 mM EDTA; 1% SDS) and eluted at 65° C. for 60 min with brief vortexing to re-suspend beads every 15 min. The beads were separated from the supernatant using the magnet and 200 µL of supernatant was removed and placed in a clean tube for reverse cross-linking. Both IP and whole cell extract fractions were reverse x-linked overnight at 65° C. (minimum 8 hours, but maximum 18 hours). Heating was then used to separately reverse cross-linked both the sample for immunoprecipitation and the whole cell extract fractions by incubating overnight at 65° C. (minimum 8 hours, but maximum 18 hours). The heating facilitated the hydrolysis of the formaldehyde cross-links.

Cleanup and Purification of DNA:

Tris-EDTA buffer (50 mM Tris pH 8; 1 mM EDTA) and 2.7 µL of 30 mg/ml RNaseA (0.2 mg/mL final concentration) at a volume of 200 was added to each sample, mixed and incubated at 37° C. for 2 hours. Then 5 µL of calcium chloride solution (300 mM $CaCl_2$ in 10 mM Tris pH 8.0) was added to each sample along with 4 of 20 mg/ml proteinase K (0.2 mg/mL final concentration), mixed and incubated at 55° C. for 60 minutes. Then 400 µL of phenol:chloroform: isoamyl alcohol at 25:24:1 ratio (Sigma Aldrich #P3803) was added to each tube, mixed on a vortex mixer on low setting (5/10) and inverted each tube to mix further.

A PhaseLock Gel™ tube (Qiagen, 3 Prime) was prepared for each sample by centrifuging the tube at room temperature for 30 seconds at 10,000 RPM. Next, the sample DNA in phenol:chloroform:isoamyl alcohol was added to the PhaseLock Gel™ tube and centrifuged at 12,000-16,000×g for 2 minutes at room temperature. Then the aqueous solution was transferred to a new 1.6 mL tube (top fraction), added 20 µL of 5 M NaCl, and 1.5 µL of 20 µg/µL glycogen (30 µg total), then added 1 mL of EtOH, and mixed by vortex or inversions. The sample was then incubated at −20° C. overnight (6-16 hours). The mixture was centrifuged at 20,000×g for 20 minutes at 4° C. to pellet the DNA, the supernatant was removed with 1 mL pipette tip, washed the pellets in 800 µL of 80% EtOH, centrifuged at 20,000×g for 20 minutes at 4° C., and removed the supernatant with 1 mL pipette tip. The sample was centrifuged again for 1 min at 20,000×g, supernatant removed, and the pellet allowed to air dry for 5-20 minutes. The pellets should not have a halo of water around them and should be glassy or flaky dry. The pellet was then dissolved in 60 µL of water, using 50 µL for sequencing.

ChIP-Seq Data Processing:

Reads for both the ChIP-seq IP and IN were aligned to the HG19 genome using Bowtie2 v.2.0.5 software (parameters=-p 4-sensitive). This resulted in genome-wide BAM files summarizing the alignment of both the IP and IN sequencing experiments.

Creating a Universal IRF8 Enhancer Score Dataset:

A universal IRF8 enhancer score dataset was generated that could apply in all downstream analyses. Peaks observed genome-wide in the aligned H3K27Ac read data with MACS v1.4 using the aligned IP BAM were designated as the ChIP-seq foreground data and the aligned IN BAM as the control background data. A stringent p value cutoff of $10^{"9}$ was used, but otherwise used the default parameters. These peaks were then merged if they had ≥12,500 base pairs between them in the human reference genome. This set of peaks is referred to as the ROSE peaks, and the rank of the highest-scoring ROSE peak overlapping the IRF8 transcript for a given sample is recorded as "IRF8 ROSE Rank" for that sample.

The set of ROSE peaks was then filtered for "blacklist regions" as defined by ENCODE (https://sites.google.com/site/anshulkundaje/projects/blacklists) and ENCODE Project Consortium (2012) to remove ChIP-seq artifacts.

The filtered set of ROSE peaks from the primary patient samples were then merged into a universal H3K27Ac enrichment map by taking the union of the coordinates of each peak from a given sample with all of the peaks that overlapped it from the other samples. This generated a universal map of H3K27Ac enrichment. Then each enriched region was quantified within this universal map within each sample (including cell lines) by, for a given region, summing the number of IP reads that mapped within the region and dividing by the number of reads mapping in the full experiment multiplied by a million ("reads per million", or RPM). A similar RPM score for the IN reads was calculated. The IN RPM was subtracted from the IP RPM to achieve the overall score for a given region within the universal map for a given sample. A negative binomial distribution was fit to the scores for a given sample using the fitdistr function in the R MASS library v7.3.45. The tail of the distribution was located as the point where the cumulative distribution function of this negative binomial crossed 0.99 (equivalent to a p value of 0.01). The overall scores for all of the sample's regions by this point were divided, so that any region of enrichment that scored in the bottom 99% of the fitted negative binomial distribution scored below 1 (deemed a "typical enhancer") and any region that scored above the 99% mark scores above 1 (deemed a "super-enhancer"). These scores are termed the "RECOMB" scores for each sample against a universal map. Each sample's RECOMB scores was then normalized against all other samples using quantile normalization, and with the floor set at 0.

Visualization of ChIP-seq Data:

The genome-wide localization of H3K27Ac was visualized using the Integrative Genomics Viewer (IGV) version 2.3.60 after converting the BAM files to IGV formatted t files using MACS2 to create a pileup (extsize 200) and the igvtools v2.3.9 software's igvtools toTDF command. The Y-axis of each track is set to begin just above the level of noise (0.25) and end at a level that approximates half the level required to view the full height of the peak over a control region centered at the MALAT1 gene.

TABLE 2

AML cell line IRF8 enhancer strength, mRNA level and tamibarotene anti-proliferative potency

| Cell Line | IRF8 enhancer (RECOMB) | IRF8 mRNA ($\log_2$) | Tamibarotene anti-proliferative potency ($EC_{50}$, nM) |
|---|---|---|---|
| EOL-1 | 0.77 | 8.96 | 0.89 |
| Kasumi-1 | 1.22 | 4.06 | >50000 |
| KG-1a | 0.00 | 0.68 | >50000 |
| PL21 | 3.10 | 7.69 | 1.41 |
| MV4-11 | 2.44 | 9.48 | 0.17 |
| HL60* | 0.17 | 2.63 | 1.64 |
| OCI-AML3 | 1.72 | 9.65 | 0.34 |
| OCI-AML2 | 1.36 | 8.88 | 0.34 |
| Nomo-1 | 1.58 | 8.04 | 0.48 |
| OCI-M1 | 0.00 | 0.04 | >50000 |
| HEL | 0.00 | 0.00 | >50000 |
| Sig-M5 | 1.53 | 8.53 | 0.46 |
| THP-1 | 1.87 | 8.73 | 0.95 |

*HL60 is an APL cell line.

Figure 6:
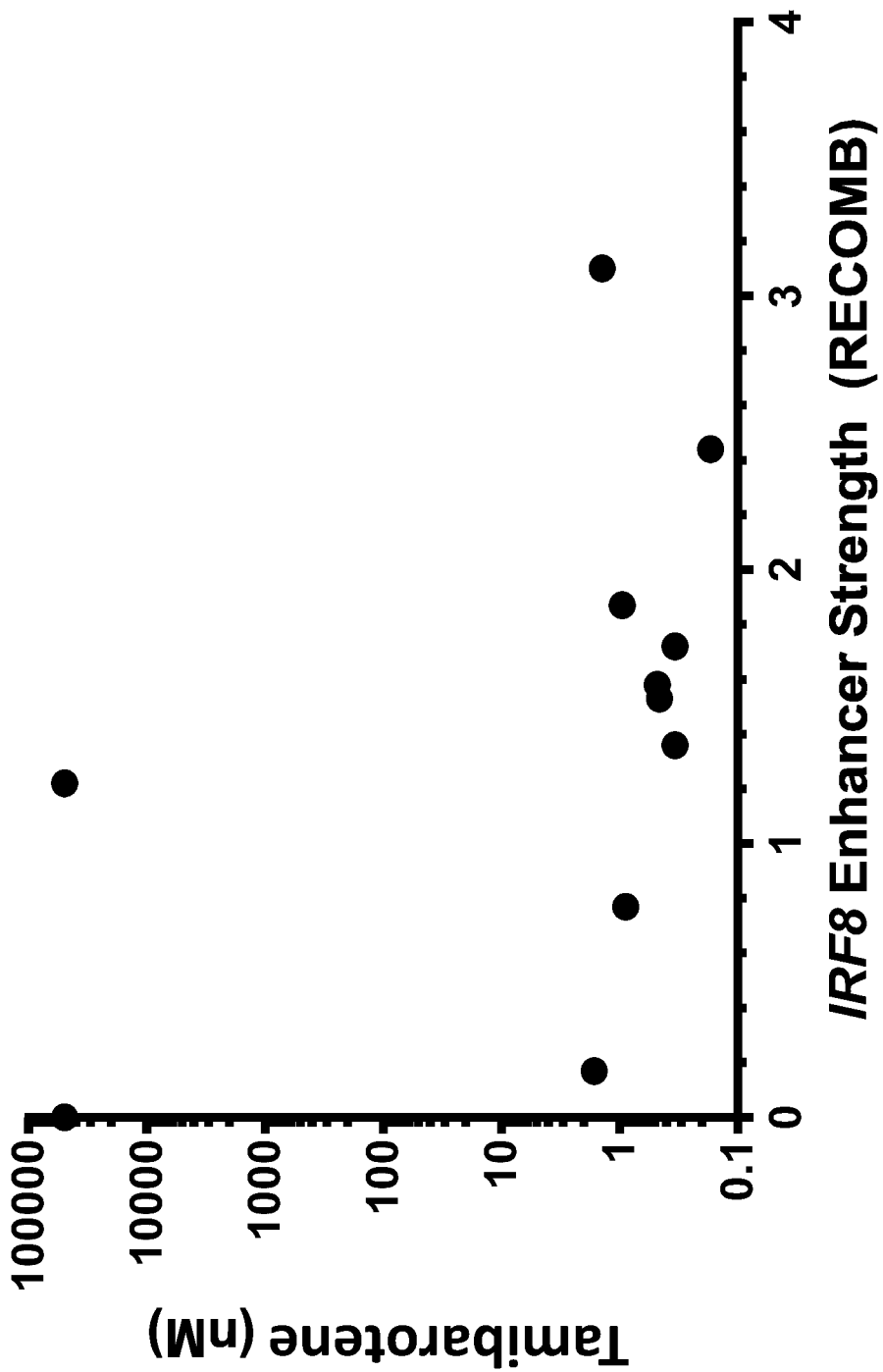
FIG. 6 shows correlation of tamibarotene anti-proliferative potency with IRF8 enhancer strength in AML cell lines. Plot of AML cell line tamibarotene sensitivity ($EC_{50}$ value, nM) as a function of IRF8 RECOMB enhancer scores. Note, top-left point with IRF8 enhancer score=0 and tamibarotene $EC_{50}$ value imputed as 50 μM (non-responsive) represents results of 3 AML cell lines with no detectable IRF8 enhancer peak and no anti-proliferative response to tamibarotene.

The data above demonstrates that an IRF8 RECOMB enhancer score of ≥1.0 (a RECOMB score of ≥1.0 defines a super enhancer) correlates well with responsiveness to tamibarotene. Excluding the HL60 APL cell line, that cutoff value produced 1 false positive (Kasumi-1) and one false negative (EOL-1) out of twelve non-APL AML cell lines tested. Raising the cutoff to a RECOMB score of ≥1.25 would eliminate the false positive, while lowering the cutoff to a RECOMB score of ≥0.75 would eliminate the false negative. This data is also presented in graph form in FIG. 6. A similar correlation between IRF8 mRNA level and responsiveness to tamibarotene was also observed, with cell lines having a IRF8 mRNA TPM($\log_2$) value of greater than 4.25 all demonstrating tamibarotene sensitivity.

Figure 7:
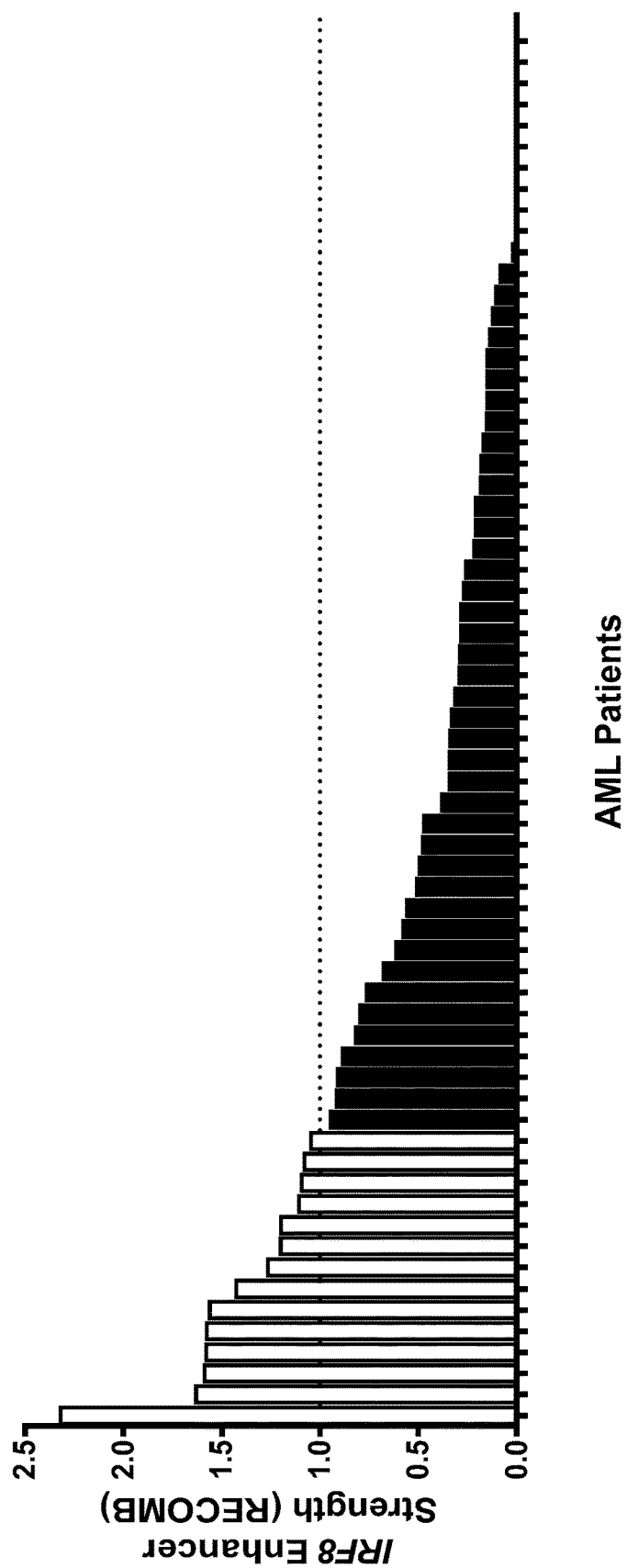
FIG. 7 depicts IRF8 enhancer strength in AML patient samples. Rank order plot of IRF8 enhancer strength under the RECOMB scoring method for 66 AML patient samples. Each bar represents the IRF8 enhancer strength for a single AML patient. The Y-axis demonstrates individual IRF8 enhancer strength as a multiple of the cutoff (defined as 1.0, indicated by dotted line) between super-enhancers (>1.0) and typical enhancers (≤1.0). Patient samples above this threshold appear in white fill while those below are in black. 14 of the 66 patient samples (21% of the population) exceed the 1.0 threshold and were deemed to have IRF8 SEs.

We then applied enhancer profiling by ChIP-seq to a subset of AML patient samples. The IRF8 locus enhancer strength varied widely among the 66 AML patient samples, with 21% (14/66) of the patients having a SE indicated by RECOMB scores surpassing 1.0 (FIG. 7). Most patient samples exhibited minimal enhancer activity, including the lowest 14% (9/66) which had no quantifiable IRF8 enhancer.

Example 5: Correlation of IRF8 mRNA and IRF8 Enhancer Strength

Quantification of IRF8 Enhancer and Correlation of ChIP-Seq and RNA-Seq Data:

The quantile-normalized RECOMB score was used across all patients for the region called as an enhancer in the universal map that overlapped IRF8: chr16:85862582-85990086. This was correlated with the quantile-normalized TPM expression estimates for the full IRF8 gene model from RSEM using Spearman correlation. Only patients with both RNA-seq and ChIP-seq were used. The same analysis was performed in cell lines, but excluded APL cell lines.

Figure 8:
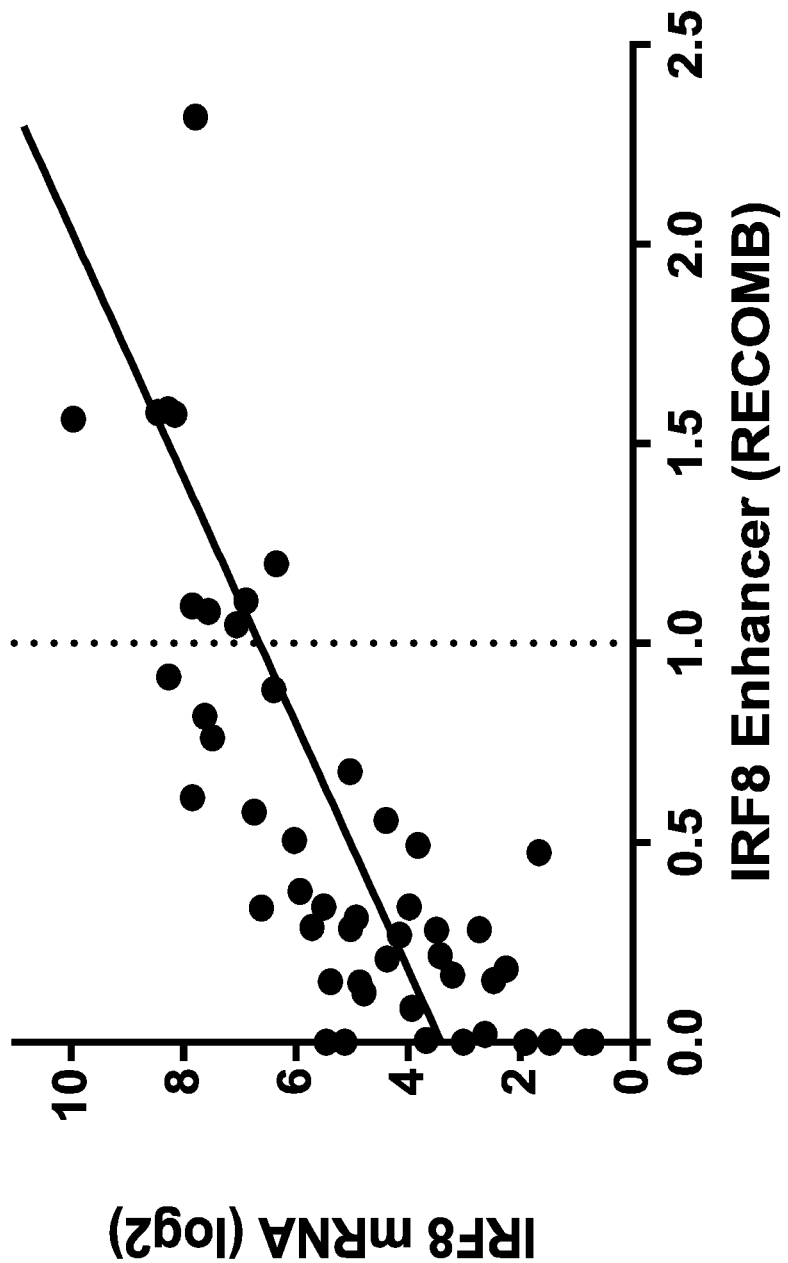
FIG. 8 shows correlation of IRF8 mRNA levels with IRF8 enhancer strength in AML patient samples. Plot of IRF8 mRNA transcript abundance by quantile normalized RNA-seq ($\log_2$ TPM; Y-axis) as a function of IRF8 RECOMB enhancer strength (X-axis) in 49 primary patient samples (those with both enhancer and expression values). The Spearman Rho correlation estimate is ~0.0.81, with a p-value of $2.2 \times 10^{-12}$.

To enable proxy estimation of IRF8 SE by IRF8 mRNA measurement, the correlation between the two was examined in the same AML patient cohort. The IRF8 mRNA measured by RNA-seq was compared with the IRF8 locus enhancer measure by RECOMB score for the H3K27ac (FIG. 8). IRF8 mRNA levels also varied widely among samples in this cohort and the IRF8 mRNA levels were highly correlated with IRF8 enhancer strength (Spearman Rho correlation estimate ~0.0.81, p-value of $2.2 \times 10^{-12}$).

Figure 9:
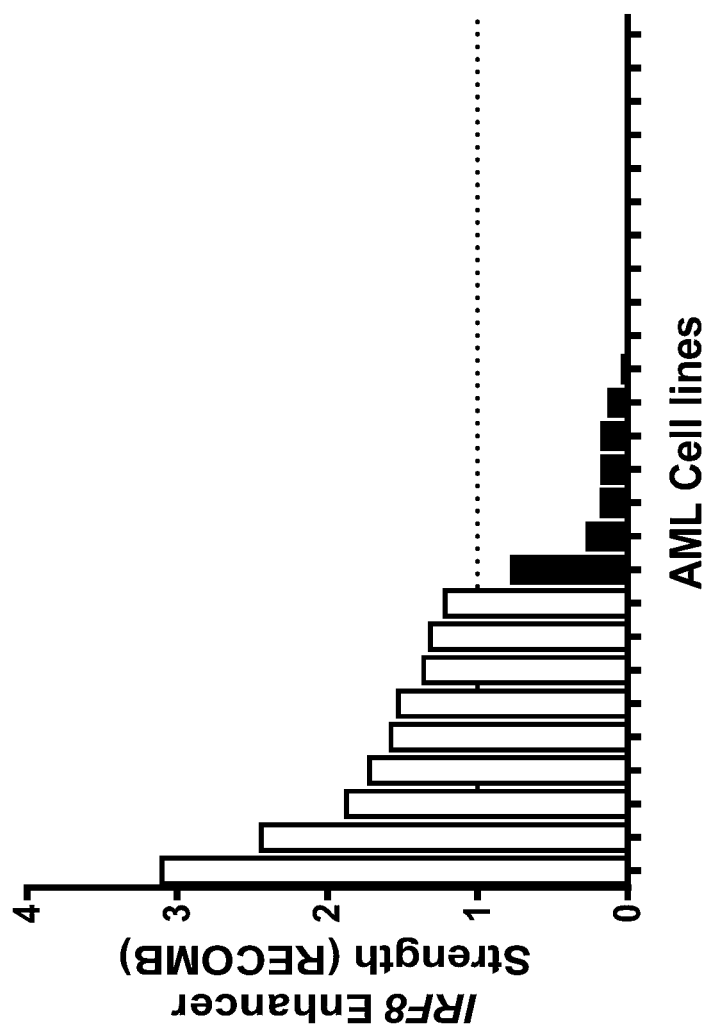
FIG. 9 shows distribution of IRF8 enhancer strength in AML cell lines. Plot of IRF8 enhancer strength under the RECOMB scoring method for 26 AML cell lines. Each bar represents the IRF8 enhancer strength for a single AML cell line. The Y-axis illustrates individual IRF8 enhancer strength as a multiple of the cutoff (defined as 1.0, indicated by dotted line) between super-enhancers (>1.0) and typical enhancers (≤1.0). Cell lines above this threshold appear in white fill, while those below are in black. Nine of the 26 AML cell lines (34% of the population) exceed the 1.0 threshold and were deemed to have IRF8 SEs.

We also profiled the value of IRF8 enhancer strength and IRF8 mRNA levels in 26 AML cell lines. Several of these cell lines were tested previously for antiproliferative sensitivity to tamibarotene (see Table 2). As observed in AML patient samples, AML cell lines exhibited a broad distribution of IRF8 enhancer strengths (FIG. 9). IRF8 enhancer strength and IRF8 mRNA levels also varied widely in 26 AML cell lines, 9 (34%) of which had IRF8 RECOMB values of ≥1.0.

As with the ANIL patient samples, the AML cell lines exhibited a strong correlation of IRF8 mRNA levels with the IRF8 enhancer strength (FIG. 10; Spearman Rho correlation estimate ~0.0.82, p-value of $2 \times 10^{-6}$), thus supporting IRF8 mRNA as a proxy measure of IRF8 enhancer strength.

Example 6: Response of PDX Models to Tamibarotene and Correlation with IRF8 mRNA Levels Different AML patient sample (AM8096, AM5512, AM7577 and AM7440)-derived xenograft models in BALB/c nude immunocompromised mice are prepared by Crown Biosciences (Beijing, China) essentially as follows.

Approximately $2 \times 10^6$ cells from each patient sample are suspended in 100 μL PBS and injected into separate mice (n=3 for each different patient sample and for the control) by IV tail injection. For AM5512, AM7577 and AM7440 xenografts, tumor burden is considered high enough to start treatment when the concentration of human CD45$^+$ cells reaches ~1-5% in the animal's peripheral blood. Human CD45$^+$ cells are detected in mouse blood (obtained via eye bleeds) using a fluorescence activated cell sorter and FITC anti-human CD45 (Biolegend, Cat#304037). For AM8096 xenografts, treatment is begun 40 days after injection of cells.

Tamibarotene is administered orally in pH 8 adjusted PBS, 1% DMSO on a daily schedule at a final dose of 6 mg per kg body weight in a 10 ml/kg volume. Mice in the vehicle arm are given the same schedule, volume, and formulation, but lacking tamibarotene. Human CD45$^+$ cell levels in peripheral blood from the treated animals and control animals are measured once a week.

Figure 11:
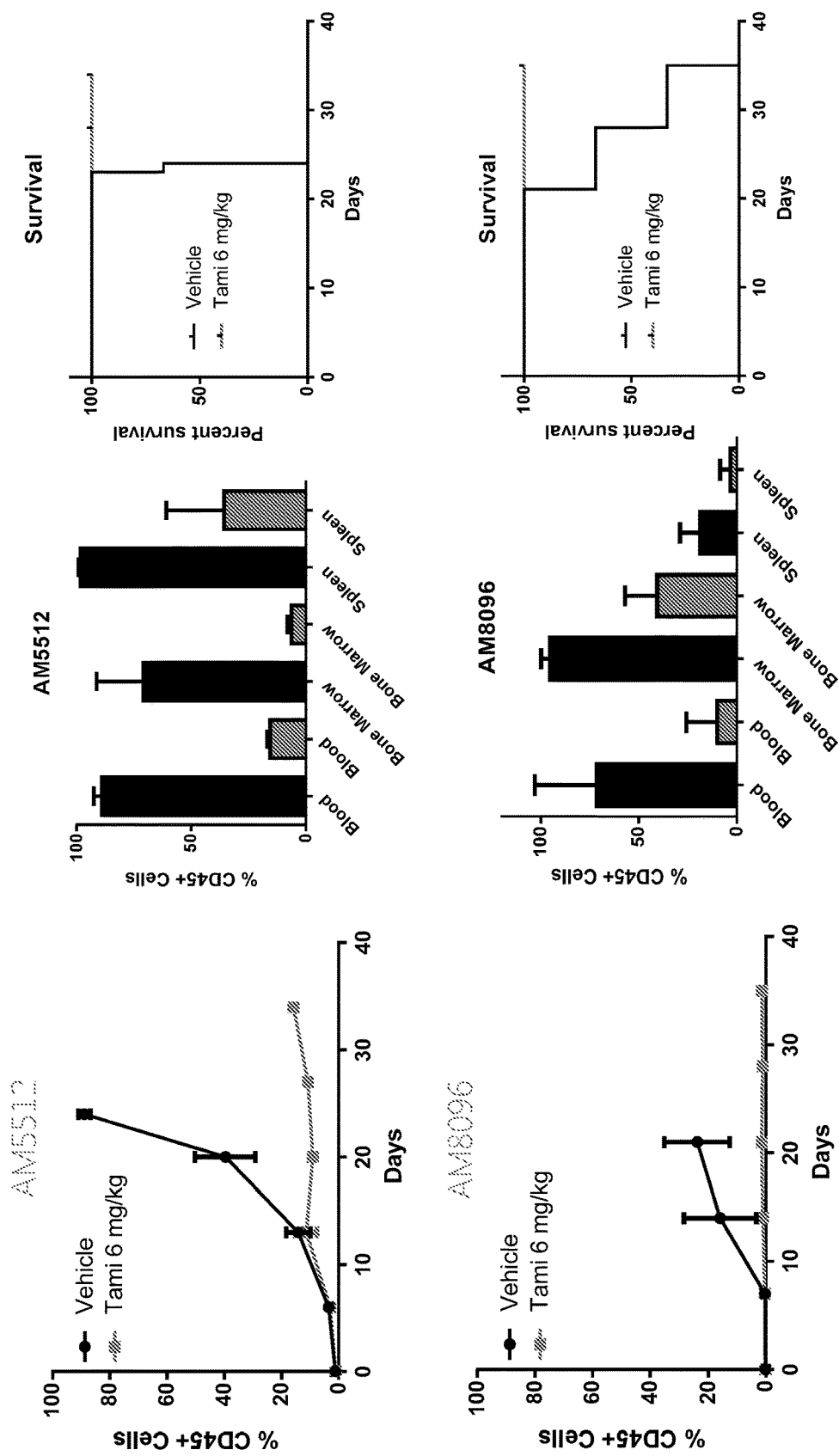
FIG. 11 depicts the response, as measured by % $CD45^+$ cells, to daily dosing of tamibarotene in two different patient-derived mouse xenograft AML models.
Figure 12:
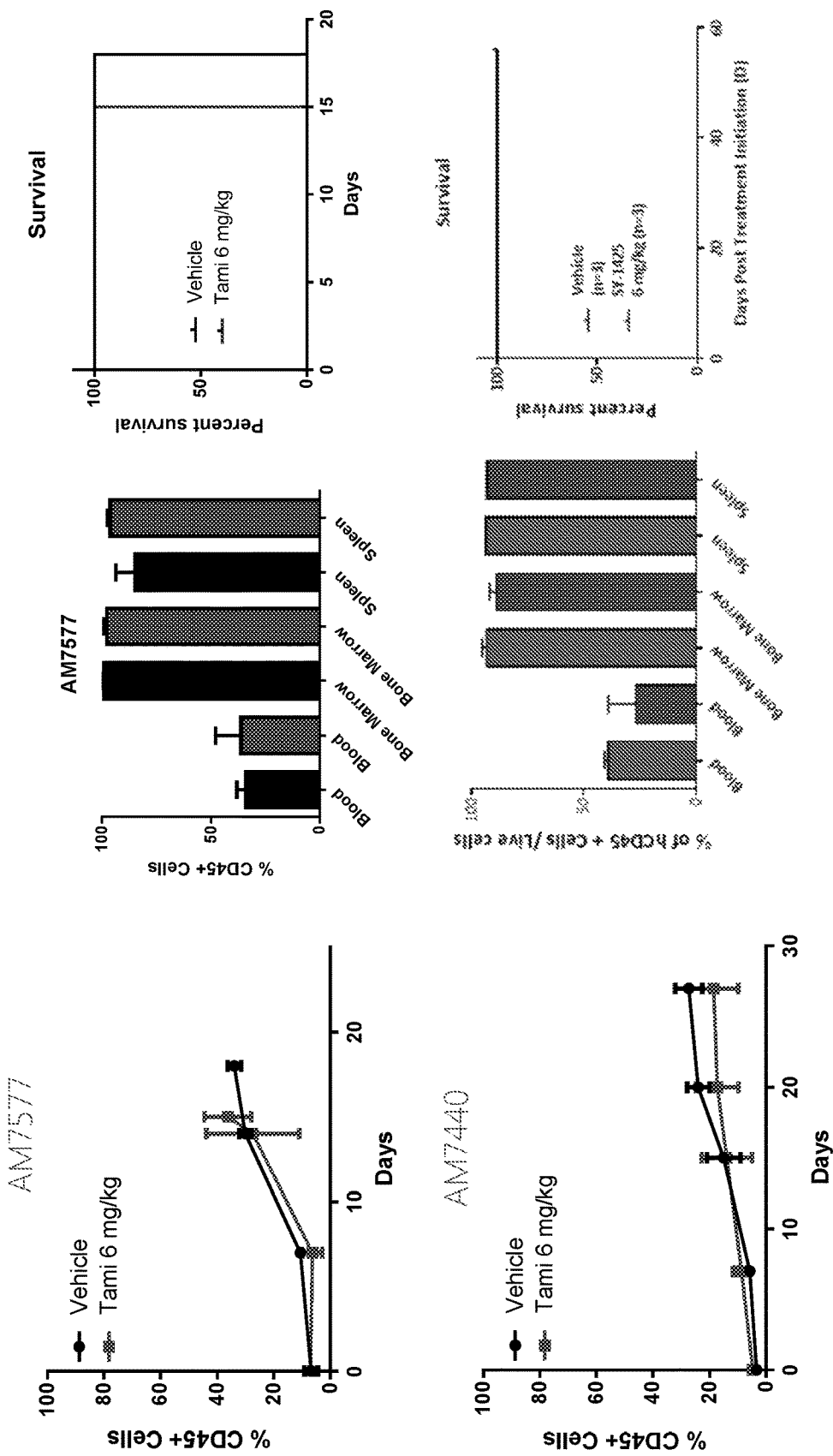
FIG. 12 depicts the response, as measured by % $CD45^+$ cells, to daily dosing of tamibarotene in two additional patient-derived mouse xenograft AML models.

AM5512 and AM8096 xenografts show a significant reduction in the total % of CD45$^+$ cells, as well as in the % of CD45$^+$ cells in blood, bone marrow and spleen, when treated with tamibarotene as compared to the vehicle control after 35 days of treatment (FIG. 11). On the other hand, AM7577 and AM7440 show no significant reduction in tumor volume between the tamibarotene treated and vehicle treated animals either overall or in any of blood, bone marrow or spleen (FIG. 12).

Figure 13:
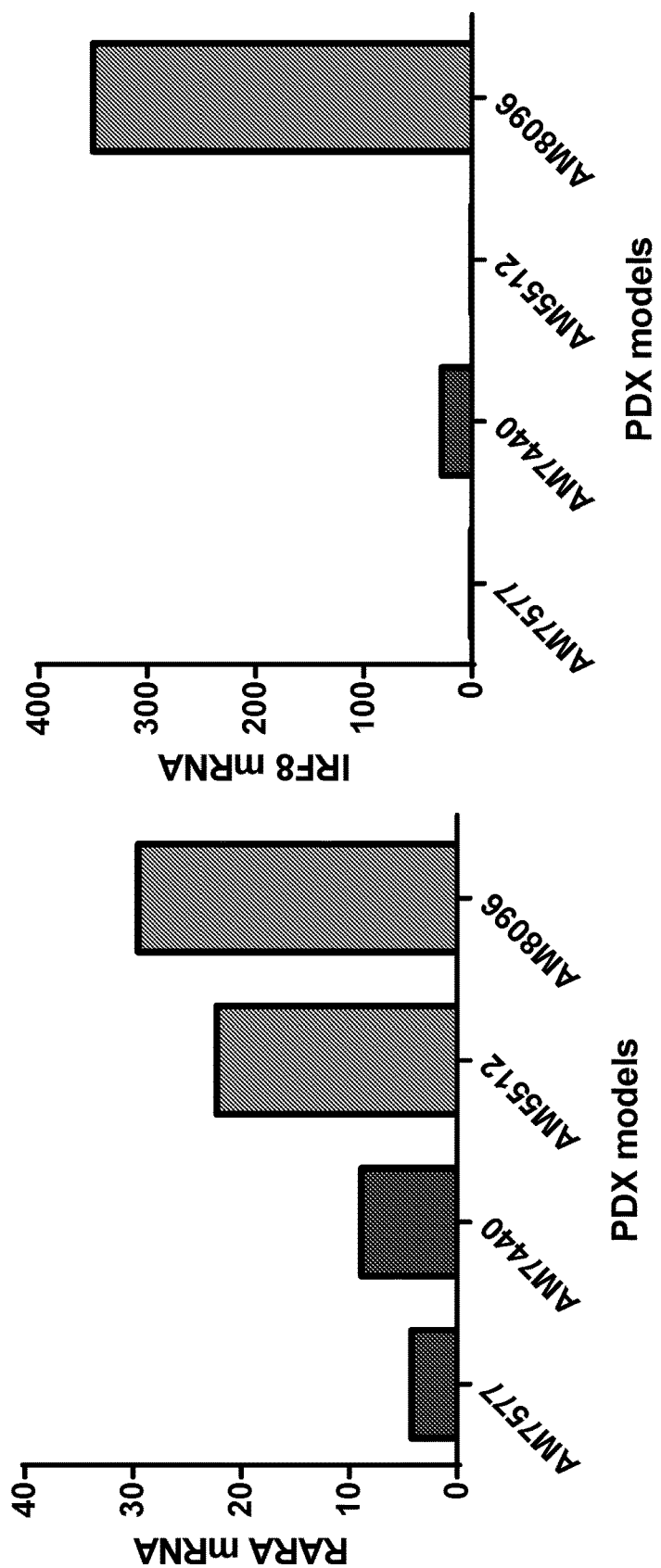
FIG. 13 depicts the IRF8 mRNA level and the RARA mRNA level in each of the four AML patient samples used in the xenograft experiments depicted in FIGS. 11 and 12. Only the tamibarotene-responsive AM8096, which produced a tamibarotene-responsive xenograft, demonstrated an IRF8 mRNA above a 100 TPM threshold. AM8096 and AM5512 (which demonstrated some responsiveness to tamibarotene) demonstrated a RARA mRNA level above a 10 TPM threshold.

We then measured both the IRF8 and RARA mRNA levels in each of the four patient samples used in the xenograft study (FIG. 13). The two non-responders in the xenograft study, AM7577 and AM7440, have IRF8 mRNA levels that fall well below 100 TPM in the assay. One of the responders, AM8096, has an IRF8 mRNA level that is above 350 TPM. The other responder, AM5512, has a very low level of IRF8 mRNA. Interestingly, these four samples showed a similar pattern of RARA mRNA level, with AM7577 and AM7440 having RARA mRNA levels below any determined prevalence cutoff (e.g., a 36% prevalence cutoff); AM8096 being significantly above that prevalence cutoff and AM5512 also being below the prevalence cutoff, but having significantly higher RARA mRNA than either of the AM7577 or AM7440 non-responders.

Example 7: Obtaining and Preparing Patient Samples for Determining IRF8 mRNA Levels and ChIP Sequencing Blood (8 mL) was drawn from non-APL AML patients and collected into an 8 mL BD Vacutainer CPT Sodium Citrate tube. Following blood collection, the tube was gently hand inverted 8-10 times to ensure adequate missing of the anticoagulant. The tube was stored upright at room temperature prior to centrifugation which was performed within two hours of collection. The blood sample was then centrifuged at room temperature (18-25° C.) for 20 minutes at 1500-1800 RCF (relative centrifugal force). After centrifugation, the blood separated into layers. The bottom layers below the gel plug were a red layer at the absolute bottom (red blood cells) and a thin gray layer above this (granulocytes and density solution). Directly above the gel plug was a clear layer of density solution, then a white layer (mononuclear cells and platelets) and a yellowish layer (plasma) on top. The white layer (up to 1 mL in volume) containing PBMCs was removed immediately after centrifugation with a Pasteur pipette. If necessary, the PBMCs can be stored in a cryovial containing 20% v/v BloodStor® freezing media (BioLife Solutions) which is added dropwise followed by gentle hand inversion to mix.

The PBMC fraction obtained in the previous step (thawed if previously frozen) was then treated simultaneously with human CD117 MicroBeads (Miltenyi Biotec) and human CD34 MicroBeads (Miltenyi Biotec), following manufacturer's directions for magnetic labeling and magnetic separation of labeled cells. Messenger RNA was then extracted from the isolated CD34$^+$/CD117$^+$ cells and quantitated using qPCR as described above.

Example 8: Synergy Between Tamibarotene and Other Agents Correlates with RARA mRNA Levels Using a Biotek EL406, 50 µL of cell media containing 20-60,000 cells/ml was distributed into white 384-well Nunc plates (Thermo). Suspension cells then received compound immediately while adherent cells lines were given one hour to reattach to the surface of the plate prior to compound addition. Tamibarotene and the second agents to be tested were dissolved in DMSO and arrayed on 384 well compound storage plates (Greiner). Each compound plate received tamibarotene and one second agent each in 5 different doses centered approximately on the EC$_{50}$ of the given compound for a given cell line, providing a total of 25 different dose combinations of the two agents.

Compound arrays were distributed to assay plates using a 20 nl 384-well pin transfer manifold on a Janus MDT workstation (Perkin Elmer). Each plate contained 8 replicates of all 5 by 5 compound concentrations in addition to five doses of each compound on its own in quadruplicate. After addition of compounds, cell plates were incubated for 5 days in a 37° C. incubator. Cell viability was evaluated using ATPlite (Perkin Elmer) following manufacturer protocols. Data was analyzed using commercially available CalcuSyn software and visualized using GraphPad Prism Software. Isobolograms plotting each of the 25 dose combination of tamibarotene and the second agents were generated and analyzed for the presence of synergy. In the isobolograms, the straight line connecting the abscissa and the ordinate values of 1.0 represents growth inhibitions that were additive for the combination of the two compounds. Plots that fall below the straight line represented synergistic growth inhibitions, with plots that fall below that line and one connecting the abscissa and the ordinate values of 0.75 represent mild synergy. Plots that fall between a line connecting the abscissa and the ordinate values of 0.75 and a line connecting the abscissa and the ordinate values of 0.25 represent moderate synergy. Plots that fall below a line connecting the abscissa and the ordinate values of 0.25 represent strong synergy. Data points that are outside the maxima in each isobologram are indicated by the number of asterisks in the upper right hand corner of the isobologram and represent data points of no synergy.

We tested azacytidine, arsenic trioxide, midostaurin, cytarabine, daunorubicin, methotrexate, idarubicin, sorafenib, decitabine, quizartinib, ABT199 (a BCL2 inhibitor), JQ1 (a BRD4 inhibitor), ATO, prednisone, SAHA, GSKJ4 (a JMID3/JARID1B inhibitor) and EPZ6438 (an EZH2 inhibitor) as second agents in these assays against various AML cell lines. FIGS. 15-21 depict isobolograms for various second agents in combination with tamibarotene in different cell lines.

Figure 15:
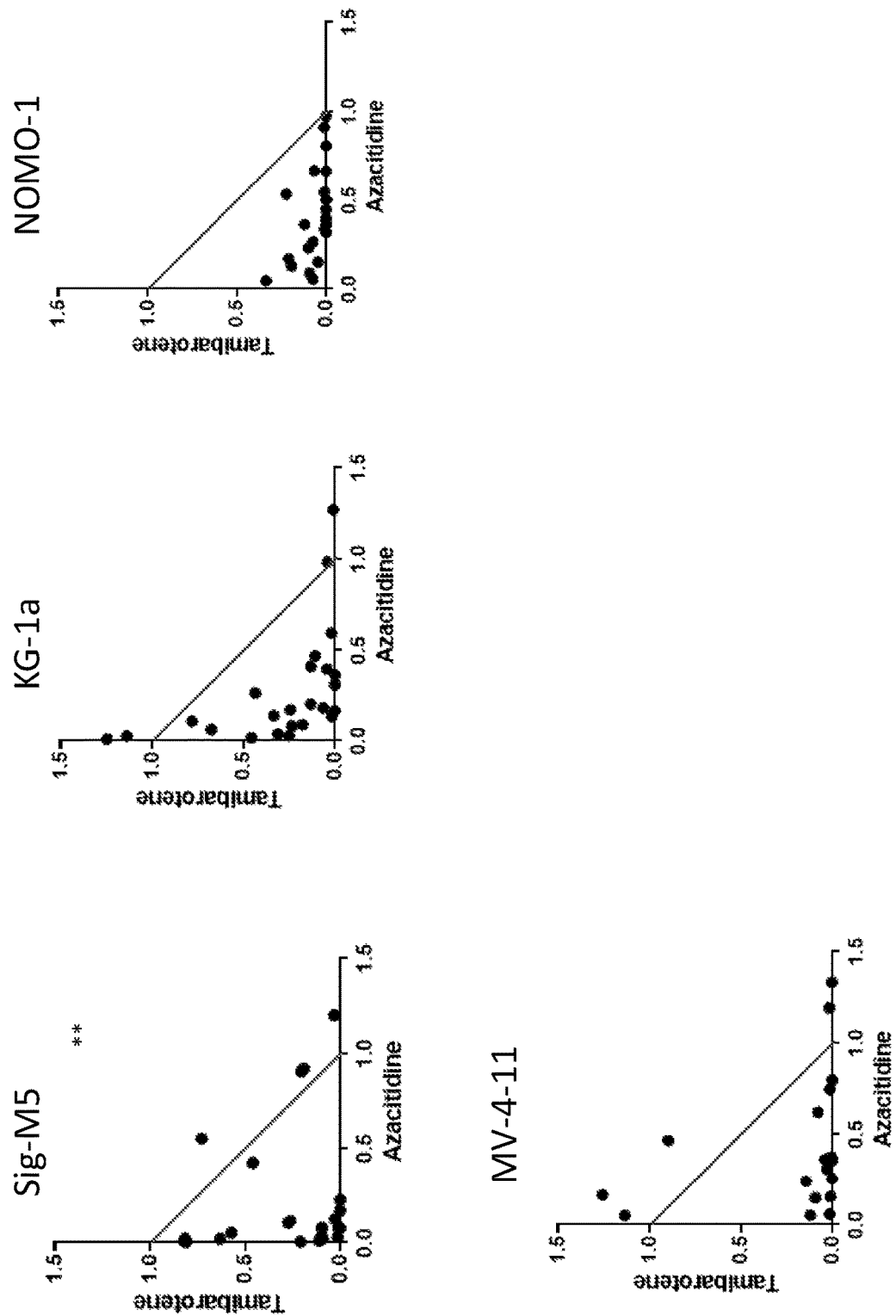
FIG. 15 depicts isobolograms for combinations of tamibarotene and azacitidine in various AML cell lines. Asterisks indicate data points outside the maxima of the isobologram.

For combinations of azacytidine and tamibarotene, moderate to strong synergy was observed for Sig-M5; moderate synergy was observed for KG-1a and NOMO-1; and mild-to-moderate synergy was observed for MV-4-11 (see FIG. 15). No synergy was observed for Kasumi-1 or OCI-M1 (data not shown).

Figure 16:
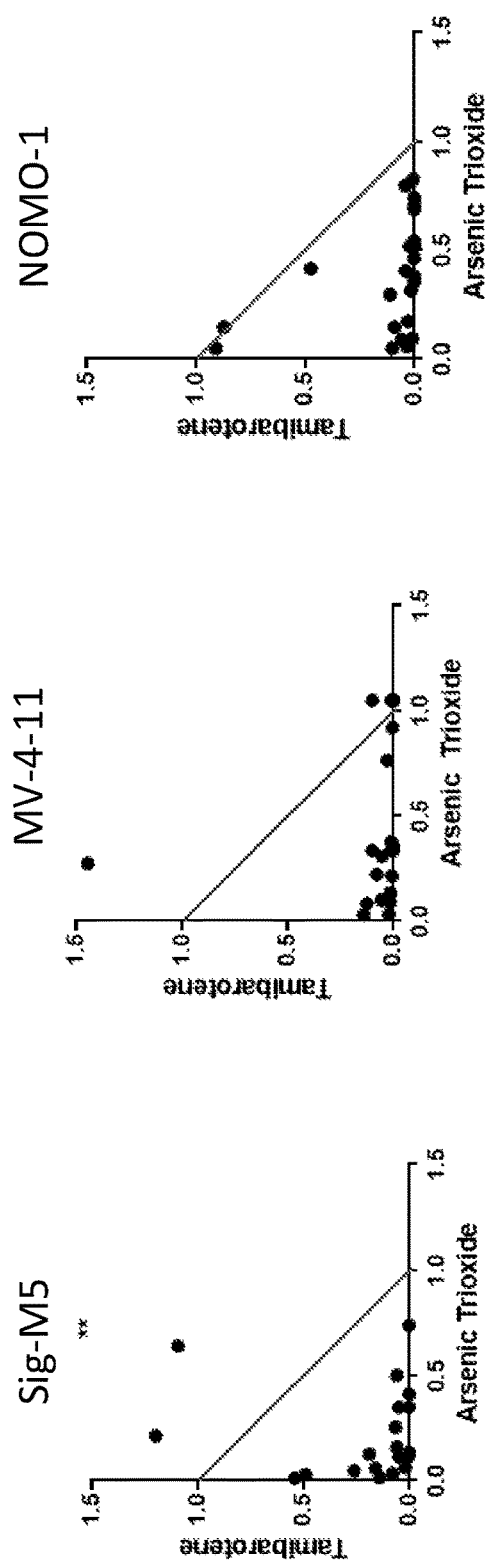
FIG. 16 depicts isobolograms for combinations of tamibarotene and arsenic trioxide in various AML cell lines. Asterisks indicate data points outside the maxima of the isobologram.

For combinations of arsenic trioxide and tamibarotene, strong synergy was observed for Sig-M5 and MV411; and moderate synergy was observed for NOMO-1 (see FIG. 16). None-to-mild synergy was observed for Kasumi-1, and no synergy was observed OCI-M1 (data not shown).

Figure 17:
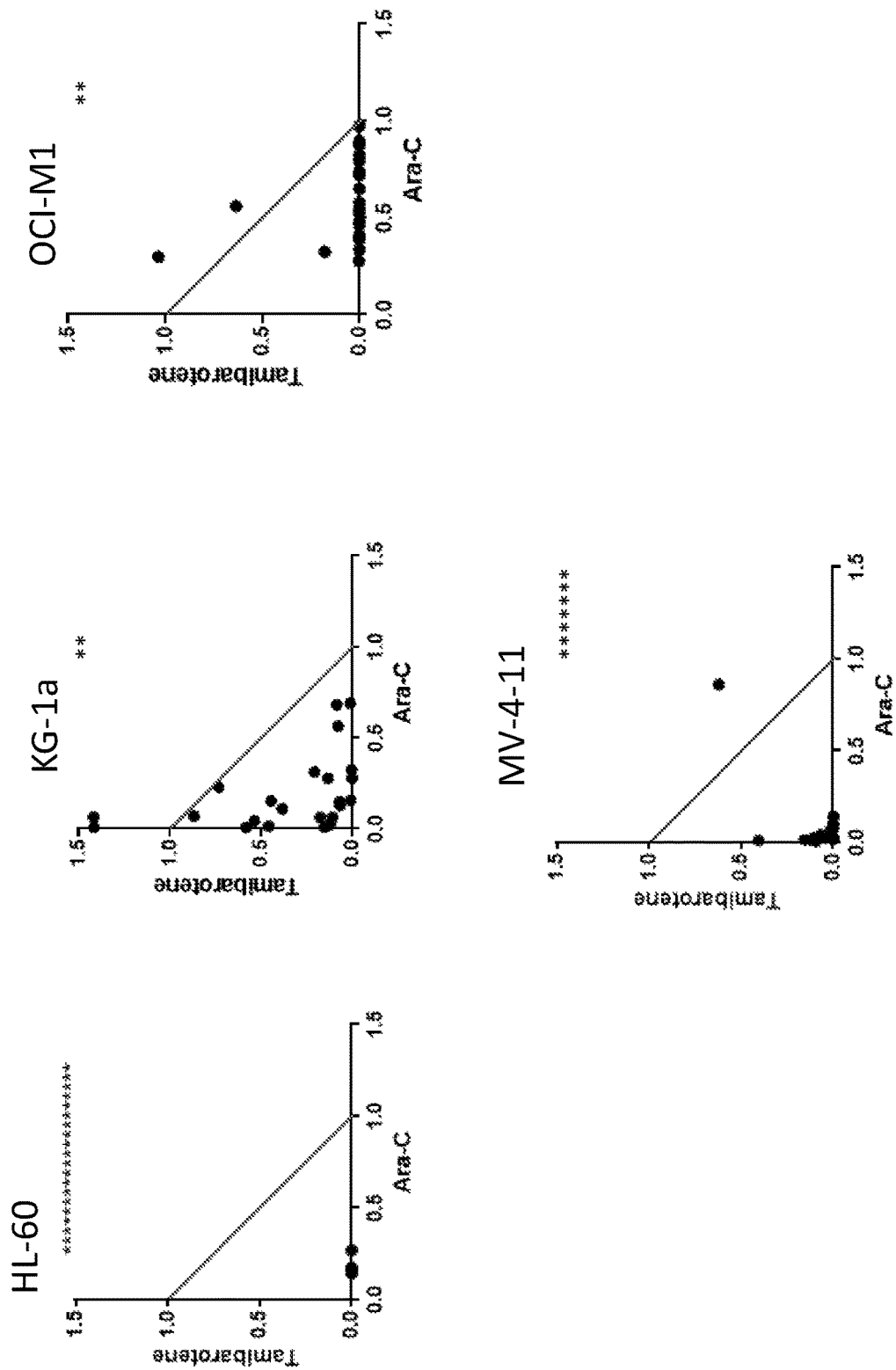
FIG. 17 depicts isobolograms for combinations of tamibarotene and Ara-C in various AML cell lines. Asterisks indicate data points outside the maxima of the isobologram.

For combinations of cytarabine (Ara-C) and tamibarotene, some moderate synergy was observed for KG-1a and OCI-M1, but no synergy was observed for HL-60 (see FIG. 17). For MV-411 the large number of data points outside the maxima (7 of 25) and the large number that showed strong synergy makes interpretation difficult.

Figure 18:
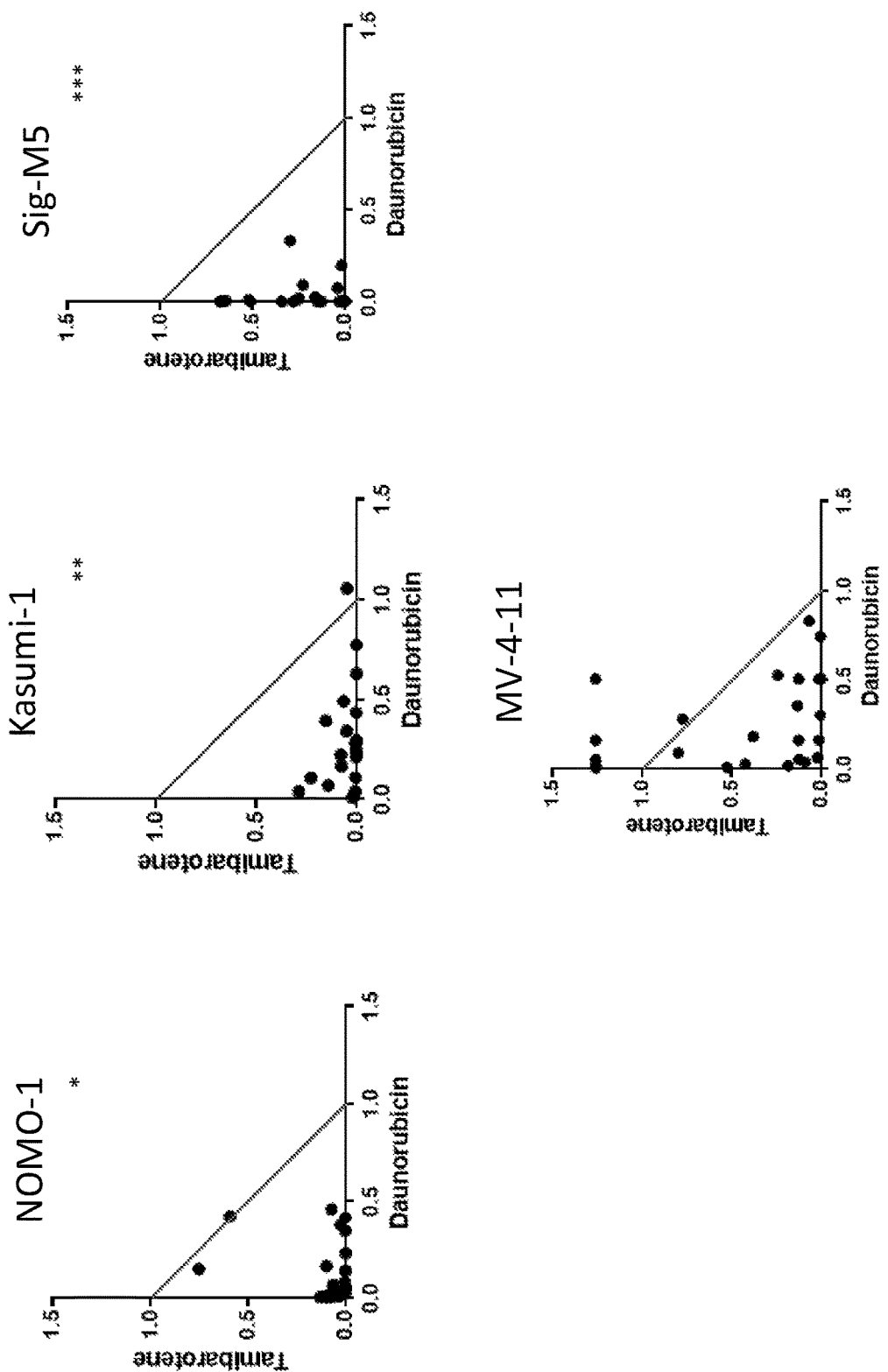
FIG. 18 depicts isobolograms for combinations of tamibarotene and daunorubicin in various AML cell lines. Asterisks indicate data points outside the maxima of the isobologram.

For combinations of daunorubicin and tamibarotene, strong synergy was observed for Kasumi-1 and NOMO-1; and moderate synergy was observed for Sig-M5 and MV-4-11 (see FIG. 18). No synergy was observed OCI-M1 (data not shown).

Figure 19:
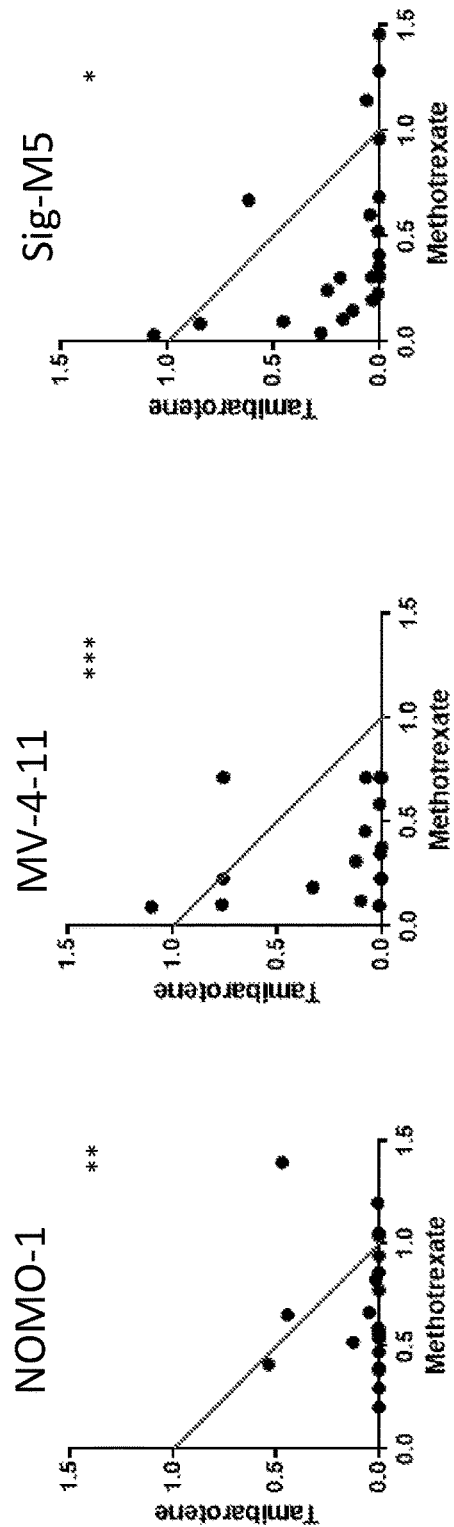
FIG. 19 depicts isobolograms for combinations of tamibarotene and methotrexate in various AML cell lines. Asterisks indicate data points outside the maxima of the isobologram.

For combinations of methotrexate and tamibarotene, moderate synergy was observed for NOMO-1, Sig-M5 and MV-4-11 (see FIG. 19). None-to-mild synergy was observed for Kasumi-1, and no synergy was observed for OCI-M1 (data not shown).

Figure 20:
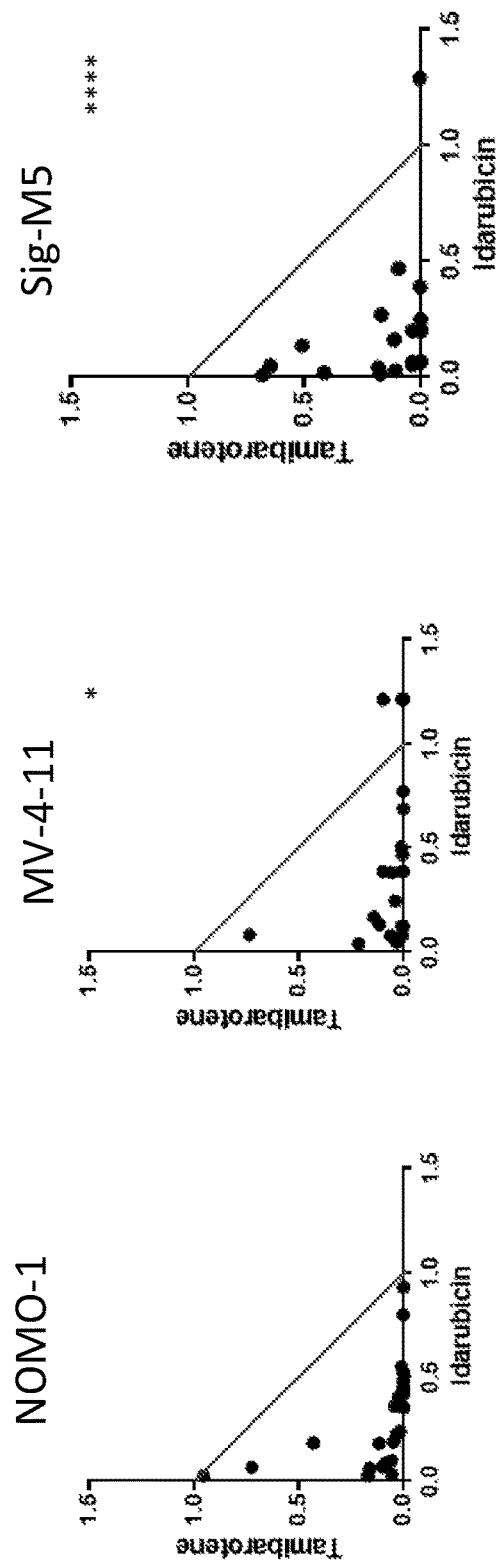
FIG. 20 depicts isobolograms for combinations of tamibarotene and idarubicin in various AML cell lines. Asterisks indicate data points outside the maxima of the isobologram.
Figure 21:
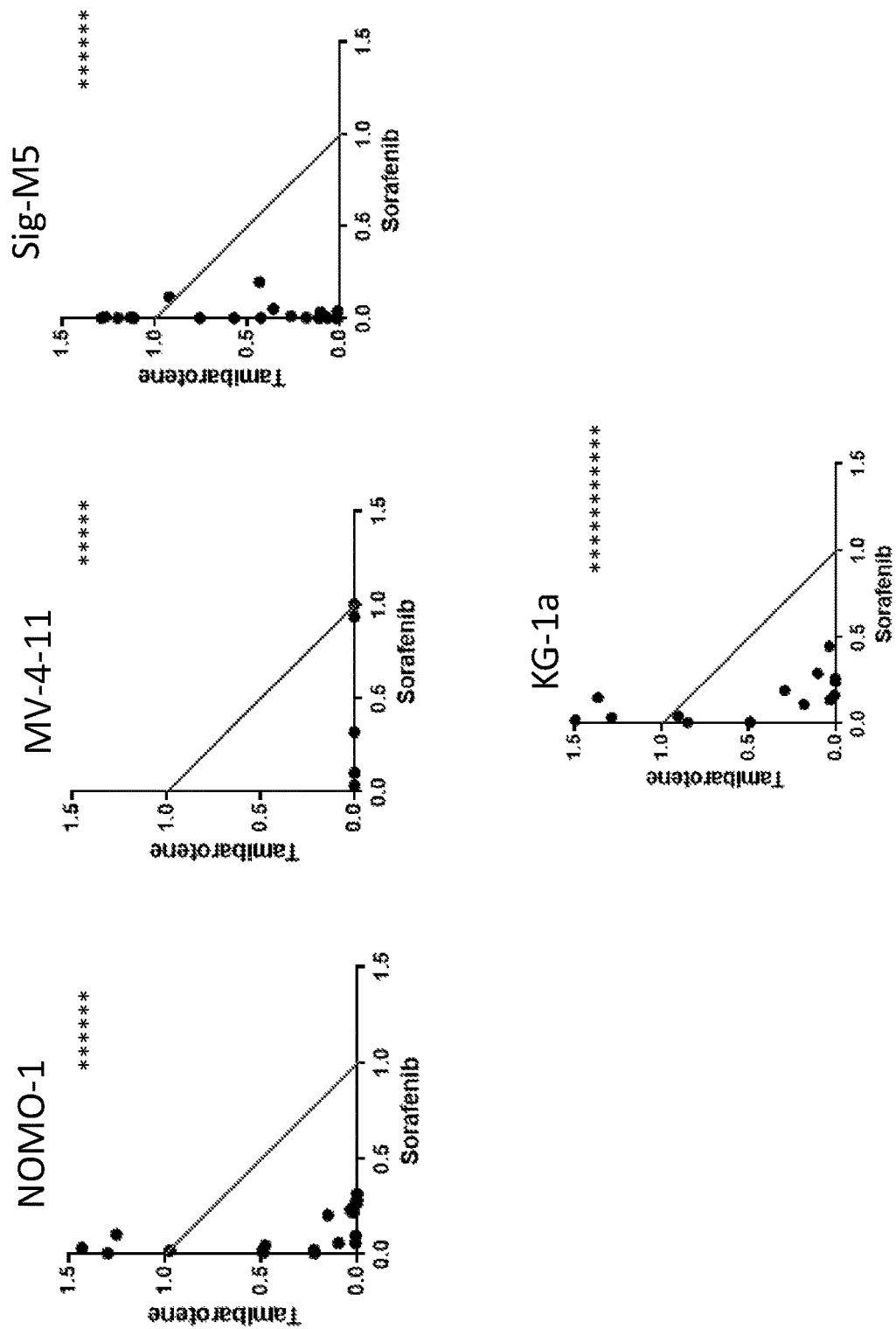
FIG. 21 depicts isobolograms for combinations of tamibarotene and sorafenib in various AML cell lines. Asterisks indicate data points outside the maxima of the isobologram.

For combinations of idarubicin and tamibarotene, moderate synergy was observed for NOMO-1, Sig-M5 and MV411 (see FIG. 20). No synergy was observed for Kasumi-1 or OCI-M1 (data not shown).

Inconclusive results were observed for a combination of sorafenib and tamibarotene in MV411, NOMO-1, KG-1a and Sig-M5 because of the large number of data points outside the maxima (see FIG. 21), but no synergy was observed for that combination in OCI-M1 (data not shown). Sorafenib is a FLT3 inhibitor and we also observed synergy for combinations of tamibarotene and other FLT3 inhibitors, such as midostaurin and quizartinib, in some of the cell lines. Without being bound by theory, we believe that synergy with FLT3 inhibitors requires both high RARA and/or high IRF8 mRNA levels, as well as high FLT3 mRNA levels. This "conditional" synergy was also seen with the GCR inhibitor prednisone, which seemed to require high GCR mRNA levels as well as high RARA and/or high IRF8 mRNA levels. It was also observed with the JMJD3/JARID1B inhibitor GSKJ4, which seemed to require high JMJD3/JARID1B mRNA levels as well as high RARA and/or high IRF8 mRNA levels to see synergy.

We observed no synergy in any cell lines tested for a combination of the BCL2 inhibitor ABT199 and tamibarotene. We also did not observe synergy with a combination of the EZH2 inhibitor EPZ6438 and tamibarotene.

We did, however observe synergy for a combination of the HDAC inhibitor SAHA and tamibarotene in high RARA and/or high IRF8 mRNA AML cell lines.

In addition, strong synergy was observed for a combination of decitabine and tamibarotene in HL-60 and KG-1a cells (data not shown).

We also observed synergy for a combination of the Zn finger transcription factor inhibitor ATO and tamibarotene.

Without being bound by any particular theory, it can be hypothesized that non-APL AML characterized by high RARA levels, high IRF8 level or a combination of both are likely to respond synergistically to combinations of tamibarotene and one or more of azacytidine, arsenic trioxide, midostaurin (in AML characterized by high FLT3 mRNA levels), cytarabine, daunorubicin, methotrexate, idarubicin, sorafenib (in AML characterized by high FLT3 mRNA levels), decitabine, quizartinib (in AML characterized by high FLT3 mRNA levels), JQ1 (a BRD4 inhibitor), ATO, prednisone (in AML characterized by high GCR mRNA levels), SAHA, and GSKJ4(in AML characterized by high JMJD3/JARID1B mRNA levels).

REFERENCES

1. Niederreither, K. & Dollé, P. Retinoic acid in development: towards an integrated view. *Nat. Rev. Genet.* 9, 541-553 (2008).
2. Chapuy, B. et al. Discovery and Characterization of Super-Enhancer-Associated Dependencies in Diffuse Large B Cell Lymphoma. *Cancer Cell* 24, 777-790 (2013).
3. Tamura, T., Kurotaki, D. & Koizumi, S. Regulation of myelopoiesis by the transcription factor IRF8. *Int. J. Hematol.* 101, 342-351 (2015).
4. Yang, J. et al. Cutting Edge: IRF8 Regulates Bax Transcription In Vivo in Primary Myeloid Cells. *J. Immunol.* 187, 4426-4430 (2011).
5. Pogosova-Agadjanyan, E. L. et al. The Prognostic Significance of IRF8 Transcripts in Adult Patients with Acute Myeloid Leukemia. *PLoS ONE* 8, e70812 (2013).
6. Sharma, A. et al. Constitutive IRF8 expression inhibits AML by activation of repressed immune response signaling. *Leukemia* 29, 157-168 (2015).
7. Smits, E. L. J. M., Anguille, S. & Berneman, Z. N. Interferon α may be back on track to treat acute myeloid leukemia. *Oncolmmunology* 2, e23619 (2013).
8. Chelbi-Alix, M. K. & Pelicano, L. Retinoic acid and interferon signaling cross talk in normal and RA-resistant APL cells. *Leuk.* 08876924 13, (1999).
9. Encode Project Consortium, An integrated encyclopedia of DNA elements in the human genome. *Nature* 489: 57-74 (2012).
10. SY-1425-P003: Effects of tamibarotene (SY-1425) on proliferation of Acute Myeloid Leukemia (AML) cell lines in comparison to all-trans retinoic acid (ATRA)
11. SY-1425-P006: Characterization of the RARA enhancer and RARα mRNA in AML patient samples and cell lines

The invention claimed is:

1. A method of treating a disease or condition selected from the group consisting of non-acute promyelocytic leukemia acute myelogenous leukemia (non-APL AML) and myelodysplastic syndrome (MDS) in a subject, the method comprising a step of:
    administering effective amounts of tamibarotene and azacitidine in combination to the subject, wherein, prior to administration, a PBMC sample or an enriched PBMC sample from the subject has been determined to have at least one of:
    (i) an elevated RARA mRNA level relative to a threshold level determined by RARA mRNA levels observed in comparable samples from a population of subjects having the same disease or condition as the subject, wherein the RARA mRNA is transcribed from a RARA gene that encodes a functional retinoic acid receptor-α and specifically excludes gene fusions that comprise all or a portion of the RARA gene; or
    (ii) an elevated IRF8 mRNA level relative to a threshold level determined by IRF8 mRNA levels observed in comparable samples from a population of subjects having the same disease or condition as the subject.

2. A method of treating a disease or condition selected from the group consisting of non-acute promyelocytic leukemia acute myelogenous leukemia (non-APL AML) and myelodysplastic syndrome (MDS) in a subject, the method comprising a step of:
    administering an effective amount of tamibarotene to a subject that is
        (i) suffering from non-APL AML or MDS; and
        (ii) receiving azacitidine;
    wherein, prior to administration of the tamibarotene, a PBMC sample or an enriched PBMC sample from the subject has been determined to have at least one of:
        (a) an elevated RARA mRNA level relative to a threshold level determined by RARA mRNA levels observed in comparable samples from a population of subjects having the same disease or condition as the subject, wherein the RARA mRNA is transcribed from a RARA gene that encodes a functional retinoic acid receptor-α and specifically excludes gene fusions that comprise all or a portion of the RARA gene; or (b) an elevated IRF8 mRNA level relative to a threshold level determined by IRF8 mRNA levels observed in comparable samples from a population of subjects having the same disease or condition as the subject.

3. A method of treating a disease or condition selected from the group consisting of non-acute promyelocytic leukemia acute myelogenous leukemia (non-APL AML) and myelodysplastic syndrome (MDS) in a subject, the method comprising a step of:

administering an effective amount of azacitidine to a subject that is
(i) suffering from non-APL AML or MDS; and
(ii) receiving tamibarotene;

wherein, prior to receiving tamibarotene, a PBMC sample or an enriched PBMC sample from the subject has been determined to have at least one of:

(a) an elevated RARA mRNA level relative to a threshold level determined by RARA mRNA levels observed in comparable samples from a population of subjects having the same disease or condition as the subject, wherein the RARA mRNA is transcribed from a RARA gene that encodes a functional retinoic acid receptor-α and specifically excludes gene fusions that comprise all or a portion of the RARA gene; or (b) an elevated IRF8 mRNA level relative to a threshold level determined by IRF8 mRNA levels observed in comparable samples from a population of subjects having the same disease or condition as the subject.

4. The method of claim 1, wherein the threshold level for RARA mRNA is a cutoff value and the threshold level for IRF8 mRNA is a cutoff value.

5. The method of claim 4, wherein the cutoff value for IRF8 mRNA is based on a pre-determined prevalence cutoff.

6. The method of claim 5, where the pre-determined prevalence cutoff is based on IRF8 enhancer strength.

7. The method of claim 1, wherein the subject is determined to have both an elevated RARA mRNA level and an elevated IRF8 mRNA level relative to their respective threshold levels.

8. The method of claim 1, wherein the disease or condition is non-APL AML.

9. The method of claim 1, wherein the disease or condition is MDS.

10. The method of claim 1, wherein each of the elevated RARA mRNA level and the elevated IRF8 mRNA level is independently determined using fluorescent hybridization, PCR, qPCR, qRT-PCR, RNA sequencing, RNA hybridization and signal amplification or northern blot.

11. The method of claim 10, wherein the elevated RARA mRNA level and the elevated IRF8 mRNA level are determined using qPCR.

12. The method of claim 2, wherein the threshold level for RARA mRNA is a cutoff value and the threshold level for IRF8 mRNA is a cutoff value.

13. The method of claim 12, wherein the cutoff value for IRF8 mRNA is based on a pre-determined prevalence cutoff.

14. The method of claim 13, where the pre-determined prevalence cutoff is based on IRF8 enhancer strength.

15. The method of claim 2, wherein the subject is determined to have both an elevated RARA mRNA level and an elevated IRF8 mRNA level relative to their respective threshold levels.

16. The method of claim 2, wherein the disease or condition is non-APL AML.

17. The method of claim 2, wherein the disease or condition is MDS.

18. The method of claim 2, wherein each of the elevated RARA mRNA level and the elevated IRF8 mRNA level is independently determined using fluorescent hybridization, PCR, qPCR, qRT-PCR, RNA sequencing, RNA hybridization and signal amplification or northern blot.

19. The method of claim 18, wherein the elevated RARA mRNA level and the elevated IRF8 mRNA level are determined using qPCR.

20. The method of claim 3, wherein the threshold level for RARA mRNA is a cutoff value and the threshold level for IRF8 mRNA is a cutoff value.

21. The method of claim 20, wherein the cutoff value for IRF8 mRNA is based on a pre-determined prevalence cutoff.

22. The method of claim 21, where the pre-determined prevalence cutoff is based on IRF8 enhancer strength.

23. The method of claim 3, wherein the subject is determined to have both an elevated RARA mRNA level and an elevated IRF8 mRNA level relative to their respective threshold levels.

24. The method of claim 3, wherein the disease or condition is non-APL AML.

25. The method of claim 3, wherein the disease or condition is MDS.

26. The method of claim 3, wherein each of the elevated RARA mRNA level and the elevated IRF8 mRNA level is independently determined using fluorescent hybridization, PCR, qPCR, qRT-PCR, RNA sequencing, RNA hybridization and signal amplification or northern blot.

27. The method of claim 26, wherein the elevated RARA mRNA level and the elevated IRF8 mRNA level are determined using qPCR.

* * * * *